United States Patent
Qu et al.

(10) Patent No.: US 10,206,980 B2
(45) Date of Patent: Feb. 19, 2019

(54) IL-15 HETERODIMERIC PROTEIN AND USES THEREOF

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Xiangdong Qu, Shanghai (CN); Xin Ye, Shanghai (CN); Jijun Yuan, Shanghai (CN); Lei Zhang, Shanghai (CN); Kan Chen, Shanghai (CN); Lianshan Zhang, Shanghai (CN); Guoqing Cao, Shanghai (CN); Zhibin Xu, Shanghai (CN); Weikang Tao, Shanghai (CN)

(73) Assignees: Shanghai Hengrui Pharmaceutical Co., Ltd., Shanghai (CN); Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/109,920

(22) PCT Filed: Dec. 25, 2014

(86) PCT No.: PCT/CN2014/094947
§ 371 (c)(1),
(2) Date: Jul. 6, 2016

(87) PCT Pub. No.: WO2015/103928
PCT Pub. Date: Jul. 16, 2015

(65) Prior Publication Data
US 2017/0020963 A1  Jan. 26, 2017

(30) Foreign Application Priority Data

Jan. 8, 2014 (CN) .......................... 2014 1 0007553

(51) Int. Cl.
| | |
|---|---|
| *A61K 38/20* | (2006.01) |
| *A61K 38/17* | (2006.01) |
| *A61K 47/68* | (2017.01) |
| *C07K 14/54* | (2006.01) |
| *C07K 14/705* | (2006.01) |
| *C07K 19/00* | (2006.01) |
| *A61K 45/06* | (2006.01) |
| *C07K 14/715* | (2006.01) |
| *A61K 38/00* | (2006.01) |

(52) U.S. Cl.
CPC ...... *A61K 38/2086* (2013.01); *A61K 38/1793* (2013.01); *A61K 45/06* (2013.01); *C07K 14/5443* (2013.01); *C07K 14/7155* (2013.01); *C07K 19/00* (2013.01); *A61K 38/00* (2013.01); *A61K 38/1774* (2013.01); *A61K 47/68* (2017.08); *C07K 2319/30* (2013.01)

(58) Field of Classification Search
CPC .............................. A61K 39/395; C07K 14/48
See application file for complete search history.

(56) References Cited

U.S. PATENT DOCUMENTS

| | | | |
|---|---|---|---|
| 2010/0286374 A1 | 11/2010 | Kannan et al. | |
| 2012/0177595 A1* | 7/2012 | Wong ................. | C07K 14/5443 424/85.2 |

FOREIGN PATENT DOCUMENTS

| | | |
|---|---|---|
| CN | 1760209 A | 4/2006 |
| CN | 1942481 A | 4/2007 |
| CN | 100334112 C | 8/2007 |
| CN | 101360827 A | 2/2009 |
| CN | 102558355 A | 7/2012 |
| EP | 1586585 A1 | 10/2005 |
| WO | 2012040323 A2 | 3/2012 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Ferrari-Lacraz et al, The Journal of Immunology, 2004, vol. 173, pp. 5818-5826.*
Seay et al, Journal of Virology, Jun. 2015; vol. 9, No. 12, pp. 6264-6274.*
Croce et al, Immunotherapy; 2012; vol. 4, No. 9, pp. 957-969.*

(Continued)

*Primary Examiner* — Bridget E Bunner
*Assistant Examiner* — Fozia Hamud
(74) *Attorney, Agent, or Firm* — Panitch Schwarze Belisario & Nadel LLP

(57) ABSTRACT

Provided is an IL-15 heterodimeric protein, such as an IL-15/IL-15Rα heterodimeric protein. The IL-15 heterodimeric protein contains protein (I) and protein (II). Protein (I) is recombinantly produced by combining IL-15 or a variant thereof with a first Fc variant, and protein (II) is a second Fc variant, or recombinantly produced by combining IL-15Rα or a variant thereof with a second Fc variant. The first Fc variant and the second Fc variant are preferably linked via a "Knob-into-Hole" mode. Also provided are methods of using the IL-15 heterodimeric proteins to modulate an immune response. The provided IL-15 heterodimeric proteins have significant anti-tumor activity, better biological activity and prolonged in vivo half-life compared to the IL-15 molecule alone.

19 Claims, 5 Drawing Sheets
Specification includes a Sequence Listing.

(56) References Cited

OTHER PUBLICATIONS

Stoklasek et al., "Combined IL-15/IL-15Ra Immunotherapy Maximizes IL-15 Activity In Vivo", J. Immunol., vol. 177, No. 9, pp. 6072-6080 (Nov. 2006).
Ridgway et al., "'Knobs-into-Holes' Engineering of Antibody CH3 Domains for Heavy Chain Heterodimerization", Protein Engineering, vol. 9, No. 7, pp. 617-621 (1996).
Davis et al., "SEEDbodies: Fusion Proteins Based on Strand-Exchange Engineered Domain (SEED) CH3 Hterodimers in an Fc Analogue Platform for Asymmetric Binders or Immunofusions and Bispeciic Antibodies", Protein Engineering Design & Selection, pp. 1-8 (2010).
Kolfschoten et al., "Anti-Inflammatory Activity of Human IgG4 Antibodies by Dynamic Fab Arm Exchange", Science, vol. 317, pp. 1554-1557 (2007).
Int'l Search Report dated Mar. 17, 2015 in Int'l Application No. PCT/CN2014/094947.

\* cited by examiner

SEQUENCE LISTING

```
<160> NUMBER OF SEQ ID NOS: 63

<210> SEQ ID NO 1
<211> LENGTH: 114
<212> TYPE: PRT
<213> ORGANISM: Homo sapiens

<400> SEQUENCE: 1

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 2
<211> LENGTH: 175
<212> TYPE: PRT
<213> ORGANISM: Artificial Sequence
<220> FEATURE:
<223> OTHER INFORMATION: IL-15R alpha-ECD

<400> SEQUENCE: 2

Ile Thr Cys Pro Pro Pro Met Ser Val Glu His Ala Asp Ile Trp Val
```

-continued

```
   1               5                  10                 15
Lys Ser Tyr Ser Leu Tyr Ser Arg Glu Arg Tyr Ile Cys Asn Ser Gly
            20                 25                 30

Phe Lys Arg Lys Ala Gly Thr Ser Ser Leu Thr Glu Cys Val Leu Asn
            35                 40                 45

Lys Ala Thr Asn Val Ala His Trp Thr Thr Pro Ser Leu Lys Cys Ile
            50                 55                 60

Arg Asp Pro Ala Leu Val His Gln Arg Pro Ala Pro Pro Ser Thr Val
 65                 70                 75                 80

Thr Thr Ala Gly Val Thr Pro Gln Pro Glu Ser Leu Ser Pro Ser Gly
                85                 90                 95

Lys Glu Pro Ala Ala Ser Ser Pro Ser Ser Asn Asn Thr Ala Ala Thr
                100                105                110

Thr Ala Ala Ile Val Pro Gly Ser Gln Leu Met Pro Ser Lys Ser Pro
                115                120                125

Ser Thr Gly Thr Thr Glu Ile Ser Ser His Glu Ser Ser His Gly Thr
                130                135                140

Pro Ser Gln Thr Thr Ala Lys Asn Trp Glu Leu Thr Ala Ser Ala Ser
145                 150                155                160

His Gln Pro Pro Gly Val Tyr Pro Gln Gly His Ser Asp Thr Thr
                165                170                175

<210> SEQ ID NO 3
<211> LENGTH: 77
<212> TYPE: PRT
<213> ORGANISM: Artificial Sequence
<220> FEATURE:
<223> OTHER INFORMATION: IL-15R alpha-sushi(77)

<400> SEQUENCE: 3

Ile Thr Cys Pro Pro Pro Met Ser Val Glu His Ala Asp Ile Trp Val
 1               5                  10                 15

Lys Ser Tyr Ser Leu Tyr Ser Arg Glu Arg Tyr Ile Cys Asn Ser Gly
            20                 25                 30

Phe Lys Arg Lys Ala Gly Thr Ser Ser Leu Thr Glu Cys Val Leu Asn
            35                 40                 45

Lys Ala Thr Asn Val Ala His Trp Thr Thr Pro Ser Leu Lys Cys Ile
            50                 55                 60

Arg Asp Pro Ala Leu Val His Gln Arg Pro Ala Pro Pro
 65                 70                 75

<210> SEQ ID NO 4
<211> LENGTH: 65
<212> TYPE: PRT
<213> ORGANISM: Artificial Sequence
<220> FEATURE:
<223> OTHER INFORMATION: IL-15R alpha-sushi(65)

<400> SEQUENCE: 4

Ile Thr Cys Pro Pro Pro Met Ser Val Glu His Ala Asp Ile Trp Val
 1               5                  10                 15

Lys Ser Tyr Ser Leu Tyr Ser Arg Glu Arg Tyr Ile Cys Asn Ser Gly
            20                 25                 30

Phe Lys Arg Lys Ala Gly Thr Ser Ser Leu Thr Glu Cys Val Leu Asn
            35                 40                 45

Lys Ala Thr Asn Val Ala His Trp Thr Thr Pro Ser Leu Lys Cys Ile
            50                 55                 60
```

Arg
65

<210> SEQ ID NO 5
<211> LENGTH: 73
<212> TYPE: PRT
<213> ORGANISM: Artificial Sequence
<220> FEATURE:
<223> OTHER INFORMATION: IL15Ra-sushi(73)

<400> SEQUENCE: 5

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg
65                  70

<210> SEQ ID NO 6
<211> LENGTH: 86
<212> TYPE: PRT
<213> ORGANISM: Artificial Sequence
<220> FEATURE:
<223> OTHER INFORMATION: IL15Ra-sushi(86)

<400> SEQUENCE: 6

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr
                85

<210> SEQ ID NO 7
<211> LENGTH: 102
<212> TYPE: PRT
<213> ORGANISM: Artificial Sequence
<220> FEATURE:
<223> OTHER INFORMATION: IL15Ra-sushi(102)

<400> SEQUENCE: 7

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val

```
              65                  70                  75                  80
Thr Thr Ala Gly Val Thr Pro Gln Pro Glu Ser Leu Ser Pro Ser Gly
                    85                  90                  95

Lys Glu Pro Ala Ala Ser
            100

<210> SEQ ID NO 8
<211> LENGTH: 356
<212> TYPE: PRT
<213> ORGANISM: Artificial Sequence
<220> FEATURE:
<223> OTHER INFORMATION: IL-15-Fc

<400> SEQUENCE: 8

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Glu Pro Lys Ser
        115                 120                 125

Ser Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
            290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
```

```
                    325                 330                 335
Met His Glu Ala Leu His Asn His Tyr Thr Gln Lys Ser Leu Ser Leu
                340                 345                 350

Ser Pro Gly Lys
        355

<210> SEQ ID NO 9
<211> LENGTH: 356
<212> TYPE: PRT
<213> ORGANISM: Artificial Sequence
<220> FEATURE:
<223> OTHER INFORMATION: Fc-IL-15

<400> SEQUENCE: 9

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Gly Gly Gly Ser Gly Gly Gly Gly
225                 230                 235                 240

Gly Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270

Val His Pro Ser Cys Lys Val Thr Ala Met Lys Cys Phe Leu Leu Glu
        275                 280                 285

Leu Gln Val Ile Ser Leu Glu Ser Gly Asp Ala Ser Ile His Asp Thr
290                 295                 300

Val Glu Asn Leu Ile Ile Leu Ala Asn Asn Ser Leu Ser Ser Asn Gly
305                 310                 315                 320

Asn Val Thr Glu Ser Gly Cys Lys Glu Cys Glu Glu Leu Glu Glu Lys
```

```
                    325                 330                 335
Asn Ile Lys Glu Phe Leu Gln Ser Phe Val His Ile Val Gln Met Phe
                340                 345                 350

Ile Asn Thr Ser
            355

<210> SEQ ID NO 10
<211> LENGTH: 417
<212> TYPE: PRT
<213> ORGANISM: Artificial Sequence
<220> FEATURE:
<223> OTHER INFORMATION: IL-15R alphaECD-Fc

<400> SEQUENCE: 10

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Gly
                165                 170                 175

Gly Gly Gly Ser Gly Gly Gly Gly Ser Glu Pro Lys Ser Ser Asp Lys
            180                 185                 190

Thr His Thr Cys Pro Pro Cys Pro Ala Pro Glu Leu Leu Gly Gly Pro
        195                 200                 205

Ser Val Phe Leu Phe Pro Pro Lys Pro Lys Asp Thr Leu Met Ile Ser
210                 215                 220

Arg Thr Pro Glu Val Thr Cys Val Val Val Asp Val Ser His Glu Asp
225                 230                 235                 240

Pro Glu Val Lys Phe Asn Trp Tyr Val Asp Gly Val Glu Val His Asn
                245                 250                 255

Ala Lys Thr Lys Pro Arg Glu Glu Gln Tyr Asn Ser Thr Tyr Arg Val
            260                 265                 270

Val Ser Val Leu Thr Val Leu His Gln Asp Trp Leu Asn Gly Lys Glu
        275                 280                 285

Tyr Lys Cys Lys Val Ser Asn Lys Ala Leu Pro Ala Pro Ile Glu Lys
290                 295                 300

Thr Ile Ser Lys Ala Lys Gly Gln Pro Arg Glu Pro Gln Val Tyr Thr
305                 310                 315                 320

Leu Pro Pro Ser Arg Glu Glu Met Thr Lys Asn Gln Val Ser Leu Thr
```

```
                      325                 330                 335
Cys Leu Val Lys Gly Phe Tyr Pro Ser Asp Ile Ala Val Glu Trp Glu
                340                 345                 350

Ser Asn Gly Gln Pro Glu Asn Asn Tyr Lys Thr Thr Pro Pro Val Leu
            355                 360                 365

Asp Ser Asp Gly Ser Phe Phe Leu Tyr Ser Lys Leu Thr Val Asp Lys
        370                 375                 380

Ser Arg Trp Gln Gln Gly Asn Val Phe Ser Cys Ser Val Met His Glu
385                 390                 395                 400

Ala Leu His Asn His Tyr Thr Gln Lys Ser Leu Ser Leu Ser Pro Gly
                405                 410                 415

Lys

<210> SEQ ID NO 11
<211> LENGTH: 417
<212> TYPE: PRT
<213> ORGANISM: Artificial Sequence
<220> FEATURE:
<223> OTHER INFORMATION: Fc-IL-15R alphaECD

<400> SEQUENCE: 11

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Ser Gly Gly Gly Gly
225                 230                 235                 240

Gly Ser Ile Thr Cys Pro Pro Pro Met Ser Val Glu His Ala Asp Ile
                245                 250                 255

Trp Val Lys Ser Tyr Ser Leu Tyr Ser Arg Glu Arg Tyr Ile Cys Asn
            260                 265                 270
```

```
Ser Gly Phe Lys Arg Lys Ala Gly Thr Ser Ser Leu Thr Glu Cys Val
            275                 280                 285

Leu Asn Lys Ala Thr Asn Val Ala His Trp Thr Thr Pro Ser Leu Lys
            290                 295                 300

Cys Ile Arg Asp Pro Ala Leu Val His Gln Arg Pro Ala Pro Pro Ser
305                 310                 315                 320

Thr Val Thr Thr Ala Gly Val Thr Pro Gln Pro Glu Ser Leu Ser Pro
                325                 330                 335

Ser Gly Lys Glu Pro Ala Ala Ser Ser Pro Ser Ser Asn Asn Thr Ala
                340                 345                 350

Ala Thr Thr Ala Ala Ile Val Pro Gly Ser Gln Leu Met Pro Ser Lys
                355                 360                 365

Ser Pro Ser Thr Gly Thr Thr Glu Ile Ser Ser His Glu Ser Ser His
            370                 375                 380

Gly Thr Pro Ser Gln Thr Thr Ala Lys Asn Trp Glu Leu Thr Ala Ser
385                 390                 395                 400

Ala Ser His Gln Pro Pro Gly Val Tyr Pro Gln Gly His Ser Asp Thr
                405                 410                 415

Thr

<210> SEQ ID NO 12
<211> LENGTH: 329
<212> TYPE: PRT
<213> ORGANISM: Artificial Sequence
<220> FEATURE:
<223> OTHER INFORMATION: IL-15R alpha-sushi(77)-Fc

<400> SEQUENCE: 12

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Gly Gly
65                  70                  75                  80

Ser Gly Gly Gly Gly Ser Gly Gly Ser Gly Gly Gly Gly Ser Gly Leu
                85                  90                  95

Gln Glu Pro Lys Ser Ser Asp Lys Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205
```

Ala Leu Pro Ala Pro Ile Glu Lys Thr Ile Ser Lys Ala Lys Gly Gln
            210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 13
<211> LENGTH: 329
<212> TYPE: PRT
<213> ORGANISM: Artificial Sequence
<220> FEATURE:
<223> OTHER INFORMATION: Fc-IL-15R alpha-sushi(77)

<400> SEQUENCE: 13

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Ser Gly Gly Ser Gly Gly Gly Gly
225                 230                 235                 240

```
Ser Gly Gly Gly Ser Gly Gly Gly Ser Leu Gln Ile Thr Cys Pro
             245                 250                 255

Pro Pro Met Ser Val Glu His Ala Asp Ile Trp Val Lys Ser Tyr Ser
        260                 265                 270

Leu Tyr Ser Arg Glu Arg Tyr Ile Cys Asn Ser Gly Phe Lys Arg Lys
        275                 280                 285

Ala Gly Thr Ser Ser Leu Thr Glu Cys Val Leu Asn Lys Ala Thr Asn
        290                 295                 300

Val Ala His Trp Thr Thr Pro Ser Leu Lys Cys Ile Arg Asp Pro Ala
305                 310                 315                 320

Leu Val His Gln Arg Pro Ala Pro Pro
                325

<210> SEQ ID NO 14
<211> LENGTH: 356
<212> TYPE: PRT
<213> ORGANISM: Artificial Sequence
<220> FEATURE:
<223> OTHER INFORMATION: IL-15-Fc -Knob

<400> SEQUENCE: 14

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Ser Glu Pro Lys Ser
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270
```

```
Ser Leu Tyr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
            325                 330                 335

Met His Glu Ala Leu His Asn His Tyr Thr Gln Lys Ser Leu Ser Leu
            340                 345                 350

Ser Pro Gly Lys
            355

<210> SEQ ID NO 15
<211> LENGTH: 356
<212> TYPE: PRT
<213> ORGANISM: Artificial Sequence
<220> FEATURE:
<223> OTHER INFORMATION: IL-15-Fc-Hole

<400> SEQUENCE: 15

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Gly Gly Gly Gly Ser Gly Pro Lys Ser
        115                 120                 125

Ser Asp Lys Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270
```

```
Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Thr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
            355

<210> SEQ ID NO 16
<211> LENGTH: 356
<212> TYPE: PRT
<213> ORGANISM: Artificial Sequence
<220> FEATURE:
<223> OTHER INFORMATION: Fc-Knob-IL-15

<400> SEQUENCE: 16

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Gly Gly Gly Gly Ser Gly Gly Gly
225                 230                 235                 240

Gly Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270
```

```
Val His Pro Ser Cys Lys Val Thr Ala Met Lys Cys Phe Leu Leu Glu
            275                 280                 285

Leu Gln Val Ile Ser Leu Glu Ser Gly Asp Ala Ser Ile His Asp Thr
        290                 295                 300

Val Glu Asn Leu Ile Ile Leu Ala Asn Asn Ser Leu Ser Ser Asn Gly
305                 310                 315                 320

Asn Val Thr Glu Ser Gly Cys Lys Glu Cys Glu Glu Leu Glu Glu Lys
                325                 330                 335

Asn Ile Lys Glu Phe Leu Gln Ser Phe Val His Ile Val Gln Met Phe
            340                 345                 350

Ile Asn Thr Ser
            355

<210> SEQ ID NO 17
<211> LENGTH: 356
<212> TYPE: PRT
<213> ORGANISM: Artificial Sequence
<220> FEATURE:
<223> OTHER INFORMATION: Fc-Hole-IL-15

<400> SEQUENCE: 17

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Gly Gly Gly Ser Gly Gly Gly
225                 230                 235                 240

Gly Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270
```

```
Val His Pro Ser Cys Lys Val Thr Ala Met Lys Cys Phe Leu Leu Glu
            275                 280                 285

Leu Gln Val Ile Ser Leu Glu Ser Gly Asp Ala Ser Ile His Asp Thr
    290                 295                 300

Val Glu Asn Leu Ile Ile Leu Ala Asn Asn Ser Leu Ser Ser Asn Gly
305                 310                 315                 320

Asn Val Thr Glu Ser Gly Cys Lys Glu Cys Glu Glu Leu Glu Glu Lys
                325                 330                 335

Asn Ile Lys Glu Phe Leu Gln Ser Phe Val His Ile Val Gln Met Phe
            340                 345                 350

Ile Asn Thr Ser
        355

<210> SEQ ID NO 18
<211> LENGTH: 417
<212> TYPE: PRT
<213> ORGANISM: Artificial Sequence
<220> FEATURE:
<223> OTHER INFORMATION: IL-15R alpha-ECD-Fc-Knob

<400> SEQUENCE: 18

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Gly
                165                 170                 175

Gly Gly Gly Ser Gly Gly Gly Gly Ser Glu Pro Lys Ser Ser Asp Lys
            180                 185                 190

Thr His Thr Cys Pro Pro Cys Pro Ala Pro Glu Leu Leu Gly Gly Pro
        195                 200                 205

Ser Val Phe Leu Phe Pro Pro Lys Pro Lys Asp Thr Leu Met Ile Ser
210                 215                 220

Arg Thr Pro Glu Val Thr Cys Val Val Val Asp Val Ser His Glu Asp
225                 230                 235                 240

Pro Glu Val Lys Phe Asn Trp Tyr Val Asp Gly Val Glu Val His Asn
                245                 250                 255

Ala Lys Thr Lys Pro Arg Glu Glu Gln Tyr Asn Ser Thr Tyr Arg Val
            260                 265                 270
```

```
Val Ser Val Leu Thr Val Leu His Gln Asp Trp Leu Asn Gly Lys Glu
            275                 280                 285

Tyr Lys Cys Lys Val Ser Asn Lys Ala Leu Pro Ala Pro Ile Glu Lys
        290                 295                 300

Thr Ile Ser Lys Ala Lys Gly Gln Pro Arg Glu Pro Gln Val Tyr Thr
305                 310                 315                 320

Leu Pro Pro Ser Arg Glu Glu Met Thr Lys Asn Gln Val Ser Leu Tyr
                325                 330                 335

Cys Leu Val Lys Gly Phe Tyr Pro Ser Asp Ile Ala Val Glu Trp Glu
            340                 345                 350

Ser Asn Gly Gln Pro Glu Asn Asn Tyr Lys Thr Thr Pro Pro Val Leu
        355                 360                 365

Asp Ser Asp Gly Ser Phe Phe Leu Tyr Ser Lys Leu Thr Val Asp Lys
370                 375                 380

Ser Arg Trp Gln Gln Gly Asn Val Phe Ser Cys Ser Val Met His Glu
385                 390                 395                 400

Ala Leu His Asn His Tyr Thr Gln Lys Ser Leu Ser Leu Ser Pro Gly
                405                 410                 415

Lys

<210> SEQ ID NO 19
<211> LENGTH: 417
<212> TYPE: PRT
<213> ORGANISM: Artificial Sequence
<220> FEATURE:
<223> OTHER INFORMATION: IL-15R alpha-ECD-Fc-Hole

<400> SEQUENCE: 19

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr Gly
                165                 170                 175

Gly Gly Gly Ser Gly Gly Gly Gly Ser Glu Pro Lys Ser Ser Asp Lys
            180                 185                 190

Thr His Thr Cys Pro Pro Cys Pro Ala Pro Glu Leu Leu Gly Gly Pro
        195                 200                 205

Ser Val Phe Leu Phe Pro Pro Lys Pro Lys Asp Thr Leu Met Ile Ser
```

-continued

```
                210                 215                 220
Arg Thr Pro Glu Val Thr Cys Val Val Val Asp Val Ser His Glu Asp
225                 230                 235                 240

Pro Glu Val Lys Phe Asn Trp Tyr Val Asp Gly Val Glu Val His Asn
                245                 250                 255

Ala Lys Thr Lys Pro Arg Glu Glu Gln Tyr Asn Ser Thr Tyr Arg Val
                260                 265                 270

Val Ser Val Leu Thr Val Leu His Gln Asp Trp Leu Asn Gly Lys Glu
                275                 280                 285

Tyr Lys Cys Lys Val Ser Asn Lys Ala Leu Pro Ala Pro Ile Glu Lys
                290                 295                 300

Thr Ile Ser Lys Ala Lys Gly Gln Pro Arg Glu Pro Gln Val Tyr Thr
305                 310                 315                 320

Leu Pro Pro Ser Arg Glu Glu Met Thr Lys Asn Gln Val Ser Leu Thr
                325                 330                 335

Cys Leu Val Lys Gly Phe Tyr Pro Ser Asp Ile Ala Val Glu Trp Glu
                340                 345                 350

Ser Asn Gly Gln Pro Glu Asn Asn Tyr Lys Thr Thr Pro Pro Val Leu
                355                 360                 365

Asp Ser Asp Gly Ser Phe Phe Leu Thr Ser Lys Leu Thr Val Asp Lys
                370                 375                 380

Ser Arg Trp Gln Gln Gly Asn Val Phe Ser Cys Ser Val Met His Glu
385                 390                 395                 400

Ala Leu His Asn His Tyr Thr Gln Lys Ser Leu Ser Leu Ser Pro Gly
                405                 410                 415

Lys

<210> SEQ ID NO 20
<211> LENGTH: 417
<212> TYPE: PRT
<213> ORGANISM: Artificial Sequence
<220> FEATURE:
<223> OTHER INFORMATION: Fc-Knob-IL-15R alphaECD

<400> SEQUENCE: 20

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
                35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr
                130                 135                 140

Lys Asn Gln Val Ser Leu Tyr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Ser Gly Gly Gly
225                 230                 235                 240

Gly Ser Ile Thr Cys Pro Pro Pro Met Ser Val Glu His Ala Asp Ile
                245                 250                 255

Trp Val Lys Ser Tyr Ser Leu Tyr Ser Arg Glu Arg Tyr Ile Cys Asn
            260                 265                 270

Ser Gly Phe Lys Arg Lys Ala Gly Thr Ser Ser Leu Thr Glu Cys Val
        275                 280                 285

Leu Asn Lys Ala Thr Asn Val Ala His Trp Thr Thr Pro Ser Leu Lys
    290                 295                 300

Cys Ile Arg Asp Pro Ala Leu Val His Gln Arg Pro Ala Pro Pro Ser
305                 310                 315                 320

Thr Val Thr Thr Ala Gly Val Thr Pro Gln Pro Glu Ser Leu Ser Pro
                325                 330                 335

Ser Gly Lys Glu Pro Ala Ala Ser Ser Pro Ser Ser Asn Asn Thr Ala
            340                 345                 350

Ala Thr Thr Ala Ala Ile Val Pro Gly Ser Gln Leu Met Pro Ser Lys
        355                 360                 365

Ser Pro Ser Thr Gly Thr Thr Glu Ile Ser Ser His Glu Ser Ser His
    370                 375                 380

Gly Thr Pro Ser Gln Thr Thr Ala Lys Asn Trp Glu Leu Thr Ala Ser
385                 390                 395                 400

Ala Ser His Gln Pro Pro Gly Val Tyr Pro Gln Gly His Ser Asp Thr
                405                 410                 415

Thr

<210> SEQ ID NO 21
<211> LENGTH: 417
<212> TYPE: PRT
<213> ORGANISM: Artificial Sequence
<220> FEATURE:
<223> OTHER INFORMATION: Fc-Hole-IL-15R alphaECD

<400> SEQUENCE: 21

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Ser Gly Gly Gly
225                 230                 235                 240

Gly Ser Ile Thr Cys Pro Pro Met Ser Val Glu His Ala Asp Ile
                245                 250                 255

Trp Val Lys Ser Tyr Ser Leu Tyr Ser Arg Glu Arg Tyr Ile Cys Asn
            260                 265                 270

Ser Gly Phe Lys Arg Lys Ala Gly Thr Ser Ser Leu Thr Glu Cys Val
        275                 280                 285

Leu Asn Lys Ala Thr Asn Val Ala His Trp Thr Thr Pro Ser Leu Lys
    290                 295                 300

Cys Ile Arg Asp Pro Ala Leu Val His Gln Arg Pro Ala Pro Pro Ser
305                 310                 315                 320

Thr Val Thr Thr Ala Gly Val Thr Pro Gln Pro Glu Ser Leu Ser Pro
                325                 330                 335

Ser Gly Lys Glu Pro Ala Ala Ser Ser Pro Ser Ser Asn Asn Thr Ala
            340                 345                 350

Ala Thr Thr Ala Ala Ile Val Pro Gly Ser Gln Leu Met Pro Ser Lys
        355                 360                 365

Ser Pro Ser Thr Gly Thr Thr Glu Ile Ser Ser His Glu Ser Ser His
    370                 375                 380

Gly Thr Pro Ser Gln Thr Thr Ala Lys Asn Trp Glu Leu Thr Ala Ser
385                 390                 395                 400

Ala Ser His Gln Pro Pro Gly Val Tyr Pro Gln Gly His Ser Asp Thr
                405                 410                 415

Thr

<210> SEQ ID NO 22
<211> LENGTH: 329
<212> TYPE: PRT
<213> ORGANISM: Artificial Sequence
<220> FEATURE:
<223> OTHER INFORMATION: IL-15R alpha-sushi(77)-Fc-Knob

<400> SEQUENCE: 22

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
```

```
                    35                  40                  45
Lys Ala Thr Asn Val Ala His Trp Thr Thr Pro Ser Leu Lys Cys Ile
 50                  55                  60

Arg Asp Pro Ala Leu Val His Gln Arg Pro Ala Pro Pro Ser Gly Gly
 65                  70                  75                  80

Ser Gly Gly Gly Gly Ser Gly Gly Gly Ser Gly Gly Gly Gly Ser Leu
                 85                  90                  95

Gln Glu Pro Lys Ser Ser Asp Lys Thr His Thr Cys Pro Pro Cys Pro
                100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Tyr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 23
<211> LENGTH: 329
<212> TYPE: PRT
<213> ORGANISM: Artificial Sequence
<220> FEATURE:
<223> OTHER INFORMATION: IL-15R alpha-sushi(77)-Fc-Hole

<400> SEQUENCE: 23

Ile Thr Cys Pro Pro Pro Met Ser Val Glu His Ala Asp Ile Trp Val
 1               5                  10                  15

Lys Ser Tyr Ser Leu Tyr Ser Arg Glu Arg Tyr Ile Cys Asn Ser Gly
                 20                  25                  30

Phe Lys Arg Lys Ala Gly Thr Ser Ser Leu Thr Glu Cys Val Leu Asn
             35                  40                  45

Lys Ala Thr Asn Val Ala His Trp Thr Thr Pro Ser Leu Lys Cys Ile
 50                  55                  60

Arg Asp Pro Ala Leu Val His Gln Arg Pro Ala Pro Pro Ser Gly Gly
```

```
                65                  70                  75                  80
        Ser Gly Gly Gly Ser Gly Gly Ser Gly Gly Gly Ser Leu
                        85                  90                  95

Gln Glu Pro Lys Ser Ser Asp Lys Thr His Thr Cys Pro Cys Pro
                    100                 105                 110

Ala Pro Glu Leu Leu Gly Gly Pro Ser Val Phe Leu Phe Pro Pro Lys
                    115                 120                 125

Pro Lys Asp Thr Leu Met Ile Ser Arg Thr Pro Glu Val Thr Cys Val
                130                 135                 140

Val Val Asp Val Ser His Glu Asp Pro Glu Val Lys Phe Asn Trp Tyr
        145                 150                 155                 160

Val Asp Gly Val Glu Val His Asn Ala Lys Thr Lys Pro Arg Glu Glu
                        165                 170                 175

Gln Tyr Asn Ser Thr Tyr Arg Val Val Ser Val Leu Thr Val Leu His
                    180                 185                 190

Gln Asp Trp Leu Asn Gly Lys Glu Tyr Lys Cys Lys Val Ser Asn Lys
                    195                 200                 205

Ala Leu Pro Ala Pro Ile Glu Lys Thr Ile Ser Lys Ala Lys Gly Gln
                210                 215                 220

Pro Arg Glu Pro Gln Val Tyr Thr Leu Pro Pro Ser Arg Glu Glu Met
        225                 230                 235                 240

Thr Lys Asn Gln Val Ser Leu Thr Cys Leu Val Lys Gly Phe Tyr Pro
                        245                 250                 255

Ser Asp Ile Ala Val Glu Trp Glu Ser Asn Gly Gln Pro Glu Asn Asn
                    260                 265                 270

Tyr Lys Thr Thr Pro Pro Val Leu Asp Ser Asp Gly Ser Phe Phe Leu
                    275                 280                 285

Thr Ser Lys Leu Thr Val Asp Lys Ser Arg Trp Gln Gln Gly Asn Val
                290                 295                 300

Phe Ser Cys Ser Val Met His Glu Ala Leu His Asn His Tyr Thr Gln
        305                 310                 315                 320

Lys Ser Leu Ser Leu Ser Pro Gly Lys
                        325

<210> SEQ ID NO 24
<211> LENGTH: 329
<212> TYPE: PRT
<213> ORGANISM: Artificial Sequence
<220> FEATURE:
<223> OTHER INFORMATION: Fc-Knob-IL-15R alpha-sushi(77)

<400> SEQUENCE: 24

Glu Pro Lys Ser Ser Asp Lys Thr His Thr Cys Pro Pro Cys Pro Ala
        1               5                   10                  15

Pro Glu Leu Leu Gly Gly Pro Ser Val Phe Leu Phe Pro Pro Lys Pro
                        20                  25                  30

Lys Asp Thr Leu Met Ile Ser Arg Thr Pro Glu Val Thr Cys Val Val
                    35                  40                  45

Val Asp Val Ser His Glu Asp Pro Glu Val Lys Phe Asn Trp Tyr Val
                50                  55                  60

Asp Gly Val Glu Val His Asn Ala Lys Thr Lys Pro Arg Glu Glu Gln
        65                  70                  75                  80

Tyr Asn Ser Thr Tyr Arg Val Val Ser Val Leu Thr Val Leu His Gln
                        85                  90                  95

Asp Trp Leu Asn Gly Lys Glu Tyr Lys Cys Lys Val Ser Asn Lys Ala
```

```
                    100                 105                 110
Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr
            130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys Ser Gly Gly Ser Gly Gly Gly Gly
225                 230                 235                 240

Ser Gly Gly Gly Ser Gly Gly Gly Ser Leu Gln Ile Thr Cys Pro
                245                 250                 255

Pro Pro Met Ser Val Glu His Ala Asp Ile Trp Val Lys Ser Tyr Ser
            260                 265                 270

Leu Tyr Ser Arg Glu Arg Tyr Ile Cys Asn Ser Gly Phe Lys Arg Lys
            275                 280                 285

Ala Gly Thr Ser Ser Leu Thr Glu Cys Val Leu Asn Lys Ala Thr Asn
            290                 295                 300

Val Ala His Trp Thr Thr Pro Ser Leu Lys Cys Ile Arg Asp Pro Ala
305                 310                 315                 320

Leu Val His Gln Arg Pro Ala Pro Pro
                325

<210> SEQ ID NO 25
<211> LENGTH: 329
<212> TYPE: PRT
<213> ORGANISM: Artificial Sequence
<220> FEATURE:
<223> OTHER INFORMATION: Fc-Hole-IL-15R alpha-sushi(77)

<400> SEQUENCE: 25

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Glu Glu Met Thr
```

```
            130                 135                 140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys Ser Gly Gly Ser Gly Gly Gly Gly
225                 230                 235                 240

Ser Gly Gly Gly Ser Gly Gly Gly Ser Leu Gln Ile Thr Cys Pro
                245                 250                 255

Pro Pro Met Ser Val Glu His Ala Asp Ile Trp Val Lys Ser Tyr Ser
            260                 265                 270

Leu Tyr Ser Arg Glu Arg Tyr Ile Cys Asn Ser Gly Phe Lys Arg Lys
        275                 280                 285

Ala Gly Thr Ser Ser Leu Thr Glu Cys Val Leu Asn Lys Ala Thr Asn
    290                 295                 300

Val Ala His Trp Thr Thr Pro Ser Leu Lys Cys Ile Arg Asp Pro Ala
305                 310                 315                 320

Leu Val His Gln Arg Pro Ala Pro Pro
                325
```

<210> SEQ ID NO 26
<211> LENGTH: 232
<212> TYPE: PRT
<213> ORGANISM: Artificial Sequence
<220> FEATURE:
<223> OTHER INFORMATION: Fc-Knob

<400> SEQUENCE: 26

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Tyr Cys Leu Val Lys Gly Phe Tyr Pro Ser
145                 150                 155                 160

Asp Ile Ala Val Glu Trp Glu Ser Asn Gly Gln Pro Glu Asn Asn Tyr
```

165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 27
<211> LENGTH: 232
<212> TYPE: PRT
<213> ORGANISM: Artificial Sequence
<220> FEATURE:
<223> OTHER INFORMATION: Fc-Hole

<400> SEQUENCE: 27

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Thr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 28
<211> LENGTH: 232
<212> TYPE: PRT
<213> ORGANISM: Artificial Sequence
<220> FEATURE:
<223> OTHER INFORMATION: Fc-Knob(M): Another form of Fc
      mutation that can pair with Fc-Hole M to form a heterodimer

<400> SEQUENCE: 28

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Cys Arg Asp Glu Leu Thr
130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 29
<211> LENGTH: 232
<212> TYPE: PRT
<213> ORGANISM: Artificial Sequence
<220> FEATURE:
<223> OTHER INFORMATION: Fc-Hole(M): Another form of Fc
      mutation that can pair with Fc-Knob M to form a heterodimer

<400> SEQUENCE: 29

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro

```
                115                 120                 125
Arg Glu Pro Gln Val Cys Thr Leu Pro Pro Ser Arg Asp Glu Leu Thr
        130                 135                 140
Lys Asn Gln Val Ser Leu Ser Cys Ala Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Val
        180                 185                 190
Ser Lys Leu Thr Val Asp Lys Ser Arg Trp Gln Gln Gly Asn Val Phe
                195                 200                 205
Ser Cys Ser Val Met His Glu Ala Leu His Asn His Tyr Thr Gln Lys
        210                 215                 220
Ser Leu Ser Leu Ser Pro Gly Lys
225                 230

<210> SEQ ID NO 30
<211> LENGTH: 366
<212> TYPE: PRT
<213> ORGANISM: Artificial Sequence
<220> FEATURE:
<223> OTHER INFORMATION: Fc-Knob(M)-IL-15: different mutation site
      compared to Knob, another heterodimer mutation

<400> SEQUENCE: 30

Glu Pro Lys Ser Ser Asp Lys Thr His Thr Ser Pro Pro Ser Pro Ala
1               5                   10                  15
Pro Glu Leu Leu Gly Gly Pro Ser Val Phe Leu Phe Pro Pro Lys Pro
                20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
50                  55                  60
Asp Gly Val Glu Val His Asn Ala Lys Thr Lys Pro Arg Glu Glu Gln
65                  70                  75                  80
Tyr Asn Ser Thr Tyr Arg Val Val Ser Val Leu Thr Val Leu His Gln
                85                  90                  95
Asp Trp Leu Asn Gly Lys Glu Tyr Lys Cys Lys Val Ser Asn Lys Ala
                100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Cys Arg Asp Glu Leu Thr
        130                 135                 140
Lys Asn Gln Val Ser Leu Trp Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
        180                 185                 190
Ser Lys Leu Thr Val Asp Lys Ser Arg Trp Gln Gln Gly Asn Val Phe
                195                 200                 205
Ser Cys Ser Val Met His Glu Ala Leu His Asn His Tyr Thr Gln Lys
        210                 215                 220
Ser Leu Ser Leu Ser Pro Gly Lys Gly Gly Gly Gly Ser Gly Gly Gly
225                 230                 235                 240
```

```
Gly Ser Gly Gly Gly Ser Gly Gly Gly Ser Asn Trp Val Asn
            245                 250                 255

Val Ile Ser Asp Leu Lys Lys Ile Glu Asp Leu Ile Gln Ser Met His
    260                 265                 270

Ile Asp Ala Thr Leu Tyr Thr Glu Ser Asp Val His Pro Ser Cys Lys
        275                 280                 285

Val Thr Ala Met Lys Cys Phe Leu Leu Glu Leu Gln Val Ile Ser Leu
    290                 295                 300

Glu Ser Gly Asp Ala Ser Ile His Asp Thr Val Glu Asn Leu Ile Ile
305                 310                 315                 320

Leu Ala Asn Asn Ser Leu Ser Ser Asn Gly Asn Val Thr Glu Ser Gly
                325                 330                 335

Cys Lys Glu Cys Glu Glu Leu Glu Glu Lys Asn Ile Lys Glu Phe Leu
                340                 345                 350

Gln Ser Phe Val His Ile Val Gln Met Phe Ile Asn Thr Ser
                355                 360                 365

<210> SEQ ID NO 31
<211> LENGTH: 356
<212> TYPE: PRT
<213> ORGANISM: Artificial Sequence
<220> FEATURE:
<223> OTHER INFORMATION: IL-15-Fc-Knob(M): different mutation site
      compared to Knob, another heterodimer mutation

<400> SEQUENCE: 31

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Gly Gly Gly Ser Glu Pro Lys Ser
        115                 120                 125

Ser Asp Lys Thr His Thr Ser Pro Pro Ser Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240
```

```
Ile Glu Lys Thr Ile Ser Lys Ala Lys Gly Gln Pro Arg Glu Pro Gln
                245                 250                 255

Val Tyr Thr Leu Pro Pro Cys Arg Asp Glu Leu Thr Lys Asn Gln Val
            260                 265                 270

Ser Leu Trp Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 32
<211> LENGTH: 317
<212> TYPE: PRT
<213> ORGANISM: Artificial Sequence
<220> FEATURE:
<223> OTHER INFORMATION: c-Hole(M)-IL-15Ra-sushi(65): different
      mutation site compared to Hole, another heterodimer
      mutation

<400> SEQUENCE: 32

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Cys Thr Leu Pro Pro Ser Arg Asp Glu Leu Thr
130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

```
Ser Leu Ser Leu Ser Pro Gly Lys Gly Gly Gly Ser Gly Gly Gly
225                 230                 235                 240

Gly Ser Gly Gly Gly Ser Gly Gly Gly Ser Ile Thr Cys Pro
            245                 250                 255

Pro Pro Met Ser Val Glu His Ala Asp Ile Trp Val Lys Ser Tyr Ser
        260                 265                 270

Leu Tyr Ser Arg Glu Arg Tyr Ile Cys Asn Ser Gly Phe Lys Arg Lys
            275                 280                 285

Ala Gly Thr Ser Ser Leu Thr Glu Cys Val Leu Asn Lys Ala Thr Asn
    290                 295                 300

Val Ala His Trp Thr Thr Pro Ser Leu Lys Cys Ile Arg
305                 310                 315
```

<210> SEQ ID NO 33
<211> LENGTH: 317
<212> TYPE: PRT
<213> ORGANISM: Artificial Sequence
<220> FEATURE:
<223> OTHER INFORMATION: IL-15Ra-sushi(65)-Hole(M): different
      mutation site compared to Hole, another heterodimer
      mutation

<400> SEQUENCE: 33

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Gly Gly Gly Gly Ser Gly Gly Gly Gly Ser Gly Gly Gly Gly Ser
65                  70                  75                  80

Gly Gly Gly Gly Ser Glu Pro Lys Ser Ser Asp Lys Thr His Thr Ser
                85                  90                  95

Pro Pro Ser Pro Ala Pro Glu Leu Leu Gly Gly Pro Ser Val Phe Leu
            100                 105                 110

Phe Pro Pro Lys Pro Lys Asp Thr Leu Met Ile Ser Arg Thr Pro Glu
        115                 120                 125

Val Thr Cys Val Val Val Asp Val Ser His Glu Asp Pro Glu Val Lys
    130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
                165                 170                 175

Thr Val Leu His Gln Asp Trp Leu Asn Gly Lys Glu Tyr Lys Cys Lys
            180                 185                 190

Val Ser Asn Lys Ala Leu Pro Ala Pro Ile Glu Lys Thr Ile Ser Lys
        195                 200                 205

Ala Lys Gly Gln Pro Arg Glu Pro Gln Val Cys Thr Leu Pro Pro Ser
    210                 215                 220

Arg Asp Glu Leu Thr Lys Asn Gln Val Ser Leu Ser Cys Ala Val Lys
225                 230                 235                 240

Gly Phe Tyr Pro Ser Asp Ile Ala Val Glu Trp Glu Ser Asn Gly Gln
                245                 250                 255

Pro Glu Asn Asn Tyr Lys Thr Thr Pro Pro Val Leu Asp Ser Asp Gly
```

```
                    260                 265                 270
Ser Phe Phe Leu Val Ser Lys Leu Thr Val Asp Lys Ser Arg Trp Gln
            275                 280                 285

Gln Gly Asn Val Phe Ser Cys Ser Val Met His Glu Ala Leu His Asn
            290                 295                 300

His Tyr Thr Gln Lys Ser Leu Ser Leu Ser Pro Gly Lys
305                 310                 315
```

<210> SEQ ID NO 34
<211> LENGTH: 325
<212> TYPE: PRT
<213> ORGANISM: Artificial Sequence
<220> FEATURE:
<223> OTHER INFORMATION: IL-15Ra-sushi 73 -Fc-Hole: sushi 73
      refers to a shortened form IL15R alpha containing the sushi
      domain with 73 amino acids in length

<400> SEQUENCE: 34

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Pro Ala Leu Val His Gln Arg Ser Gly Ser Gly Gly Gly Gly
65                  70                  75                  80

Gly Ser Gly Gly Gly Ser Gly Gly Gly Ser Leu Gln Glu Pro Lys
            85                  90                  95

Ser Ser Asp Lys Thr His Thr Cys Pro Pro Cys Pro Ala Pro Glu Leu
            100                 105                 110

Leu Gly Gly Pro Ser Val Phe Leu Phe Pro Pro Lys Pro Lys Asp Thr
            115                 120                 125

Leu Met Ile Ser Arg Thr Pro Glu Val Thr Cys Val Val Val Asp Val
130                 135                 140

Ser His Glu Asp Pro Glu Val Lys Phe Asn Trp Tyr Val Asp Gly Val
145                 150                 155                 160

Glu Val His Asn Ala Lys Thr Lys Pro Arg Glu Glu Gln Tyr Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Ala Leu Pro Ala
        195                 200                 205

Pro Ile Glu Lys Thr Ile Ser Lys Ala Lys Gly Gln Pro Arg Glu Pro
210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Thr Ser Lys Leu
        275                 280                 285

Thr Val Asp Lys Ser Arg Trp Gln Gln Gly Asn Val Phe Ser Cys Ser
290                 295                 300
```

Val Met His Glu Ala Leu His Asn His Tyr Thr Gln Lys Ser Leu Ser
305                 310                 315                 320

Leu Ser Pro Gly Lys
            325

<210> SEQ ID NO 35
<211> LENGTH: 317
<212> TYPE: PRT
<213> ORGANISM: Artificial Sequence
<220> FEATURE:
<223> OTHER INFORMATION: IL-15Ra-sushi 65 -Fc-Hole: sushi 65
      refers to the sushi domain with 65 amino acids in length

<400> SEQUENCE: 35

Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Ser Gly Gly Ser Gly Gly Gly Gly Ser Gly Gly Gly Ser Gly Gly
65                  70                  75                  80

Gly Gly Ser Leu Gln Glu Pro Lys Ser Ser Asp Lys Thr His Thr Cys
            85                  90                  95

Pro Pro Cys Pro Ala Pro Glu Leu Leu Gly Gly Pro Ser Val Phe Leu
        100                 105                 110

Phe Pro Pro Lys Pro Lys Asp Thr Leu Met Ile Ser Arg Thr Pro Glu
    115                 120                 125

Val Thr Cys Val Val Val Asp Val Ser His Glu Asp Pro Glu Val Lys
130                 135                 140

Phe Asn Trp Tyr Val Asp Gly Val Glu Val His Asn Ala Lys Thr Lys
145                 150                 155                 160

Pro Arg Glu Glu Gln Tyr Asn Ser Thr Tyr Arg Val Val Ser Val Leu
            165                 170                 175

Thr Val Leu His Gln Asp Trp Leu Asn Gly Lys Glu Tyr Lys Cys Lys
        180                 185                 190

Val Ser Asn Lys Ala Leu Pro Ala Pro Ile Glu Lys Thr Ile Ser Lys
    195                 200                 205

Ala Lys Gly Gln Pro Arg Glu Pro Gln Val Tyr Thr Leu Pro Pro Ser
210                 215                 220

Arg Glu Glu Met Thr Lys Asn Gln Val Ser Leu Thr Cys Leu Val Lys
225                 230                 235                 240

Gly Phe Tyr Pro Ser Asp Ile Ala Val Glu Trp Glu Ser Asn Gly Gln
            245                 250                 255

Pro Glu Asn Asn Tyr Lys Thr Thr Pro Pro Val Leu Asp Ser Asp Gly
        260                 265                 270

Ser Phe Phe Leu Thr Ser Lys Leu Thr Val Asp Lys Ser Arg Trp Gln
    275                 280                 285

Gln Gly Asn Val Phe Ser Cys Ser Val Met His Glu Ala Leu His Asn
290                 295                 300

His Tyr Thr Gln Lys Ser Leu Ser Leu Ser Pro Gly Lys
305                 310                 315

```
<210> SEQ ID NO 36
<211> LENGTH: 338
<212> TYPE: PRT
<213> ORGANISM: Artificial Sequence
<220> FEATURE:
<223> OTHER INFORMATION: IL-15Ra-sushi 86 -Fc-Hole: sushi 86
      refers to a shortened form IL15R alpha containing the sushi
      domain with 86 amino acids in length

<400> SEQUENCE: 36

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Ser Gly Gly Ser Gly Gly Gly Ser Gly
                85                  90                  95

Gly Gly Ser Gly Gly Gly Ser Leu Gln Glu Pro Lys Ser Ser Asp
            100                 105                 110

Lys Thr His Thr Cys Pro Pro Cys Pro Ala Pro Glu Leu Leu Gly Gly
            115                 120                 125

Pro Ser Val Phe Leu Phe Pro Pro Lys Pro Lys Asp Thr Leu Met Ile
        130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
    210                 215                 220

Lys Thr Ile Ser Lys Ala Lys Gly Gln Pro Arg Glu Pro Gln Val Tyr
225                 230                 235                 240

Thr Leu Pro Pro Ser Arg Glu Glu Met Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Thr Ser Lys Leu Thr Val Asp
    290                 295                 300

Lys Ser Arg Trp Gln Gln Gly Asn Val Phe Ser Cys Ser Val Met His
305                 310                 315                 320

Glu Ala Leu His Asn His Tyr Thr Gln Lys Ser Leu Ser Leu Ser Pro
                325                 330                 335

Gly Lys

<210> SEQ ID NO 37
<211> LENGTH: 354
```

<212> TYPE: PRT
<213> ORGANISM: Artificial Sequence
<220> FEATURE:
<223> OTHER INFORMATION: IL-15Ra-sushi 102 -Fc-Hole: sushi 102
    refers to the sushi domain with 102 amino acids in length

<400> SEQUENCE: 37

```
Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Gly Gly Ser Gly Gly Gly Gly Ser Gly
            100                 105                 110

Gly Gly Ser Gly Gly Gly Ser Leu Gln Glu Pro Lys Ser Ser Asp
        115                 120                 125

Lys Thr His Thr Cys Pro Pro Cys Pro Ala Pro Glu Leu Leu Gly Gly
130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
290                 295                 300

Leu Asp Ser Asp Gly Ser Phe Phe Leu Thr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys
```

<210> SEQ ID NO 38
<211> LENGTH: 81

```
<212> TYPE: DNA
<213> ORGANISM: Artificial Sequence
<220> FEATURE:
<223> OTHER INFORMATION: Vector construction sequences include
      restriction endonuclease KpnI site sequence, Kozak sequence,
      signal peptide sequence

<400> SEQUENCE: 38
ggtaccttgt gcccgggcgc caccatggag tttgggctga gctggctttt tcttgtcgcg    60
attcttaagg gtgtccagtg c                                              81

<210> SEQ ID NO 39
<211> LENGTH: 408
<212> TYPE: DNA
<213> ORGANISM: Homo sapiens

<400> SEQUENCE: 39
atggacatgc gggtgccagc ccagctgctg ggcctgttgc tgctgtggtt ccccggctct    60
cggtgcaact gggtgaatgt aattagtgat ttgaaaaaaa ttgaagatct tattcaatct   120
atgcatattg atgctacttt atatacggaa agtgatgttc acccgagttg caaagtaaca   180
gcaatgaagt gctttctctt ggagttacaa gttatttcac ttgagtccgg cgatgcaagt   240
attcatgata cagtagaaaa tctgatcatc ttagcaaaca acagtttgtc ttctaatggg   300
aatgtaacag aatctggatg caaagaatgt gaggaactgg aggaaaaaaa tattaaagaa   360
tttttgcaga gttttgtaca tattgtccaa atgttcatca acacttct                408

<210> SEQ ID NO 40
<211> LENGTH: 591
<212> TYPE: DNA
<213> ORGANISM: Artificial Sequence
<220> FEATURE:
<223> OTHER INFORMATION: IL-15R alpha

<400> SEQUENCE: 40
atggacatgc gggtgccagc ccagctgctg ggcctgttgc tgctgtggtt ccccggctct    60
cggtgcatca cctgccctcc acctatgtcc gtggaacacg cagacatctg ggtcaagagc   120
tacagcttgt actcccgcga gcgctacatt tgtaactctg gtttcaagcg taaagccggc   180
acctccagcc tgaccgagtg cgtgttgaac aaggccacca atgtcgccca ctggacaacc   240
ccaagtctca aatgcattcg cgaccctgcc ctggttcacc aacgcccagc gccaccatcc   300
acagtaacca ctgcaggcgt gaccccacag ccagagagcc tctccccttc tggcaaagag   360
ccagcagctt catctccaag ctcaaacaac acagcggcca acagcagc tattgtcccg    420 ggctcccagc tgatgccttc aaaatcacct tccacaggca ccacagagat cagcagtcat   480
gagtcctccc acggcacccc atctcagaca acagccaaga ctgggaact cacagcatcc   540 gcctcccacc agccgccagg tgtgtatcca cagggccaca gcgacaccac t            591

<210> SEQ ID NO 41
<211> LENGTH: 762
<212> TYPE: DNA
<213> ORGANISM: Artificial Sequence
<220> FEATURE:
<223> OTHER INFORMATION: FC

<400> SEQUENCE: 41
atggacatgc gggtgccagc ccagctgctg ggcctgttgc tgctgtggtt ccccggctct    60
cggtgcgaac ctaagtcctc tgataagacc cacacatgtc cccctgcccc agctcctgag   120
```

```
ctcttgggcg gaccttccgt gtttctgttc cccccaaagc ccaaggatac ccttatgatc      180
agcagaacac ccgaagttac ttgcgtggtc gtggacgttt ctcacgaaga tcctgaagtg      240
aaattcaact ggtacgtgga tggcgtggag gtgcacaatg ctaagactaa gccccgtgaa      300
gagcagtaca actctaccta ccgggtcgtt tcagtgctga ctgttctcca tcaggactgg      360
ctcaacggga aggagtataa gtgcaaggtg tctaacaagg cactgcccgc acccatcgag      420
aagaccattt ctaaggccaa gggtcaacca cgggagccac aggtttacac attgcctccc      480
agtcgggagg agatgacaaa gaatcaagtg tcacttacat gtcttgtgaa gggcttctac      540
ccctcagaca tcgccgtgga gtgggagagc aacggacaac agaaaacaa ctacaagacc       600 acacctcctg tgctcgattc agatggttcc tttttcttgt acagcaaact caccgttgac      660
aagagtcggt ggcagcaagg aaatgtgttc agctgttctg tgatgcacga ggccctgcac      720
aaccattata cccaaaaatc tctcagcctt tctcccggca ag                        762

<210> SEQ ID NO 42
<211> LENGTH: 1134
<212> TYPE: DNA
<213> ORGANISM: Artificial Sequence
<220> FEATURE:
<223> OTHER INFORMATION: IL-15-Fc

<400> SEQUENCE: 42
atggacatgc gggtgccagc ccagctgctg ggcctgttgc tgctgtggtt ccccggctct       60
cggtgcaact gggtgaatgt aattagtgat ttgaaaaaaa ttgaagatct tattcaatct      120
atgcatattg atgctacttt atatacggaa agtgatgttc acccgagttg caaagtaaca      180
gcaatgaagt gctttctctt ggagttacaa gttatttcac ttgagtccgg cgatgcaagt      240
attcatgata cagtagaaaa tctgatcatc ttagcaaaca acagtttgtc ttctaatggg      300
aatgtaacag aatctggatg caaagaatgt gaggaactgg aggaaaaaaa tattaaagaa      360 ttttttgcaga gttttgtaca tattgtccaa atgttcatca acacttctgg cggaggaggc      420 tctggggggcg aggaagcga acctaagtcc tctgataaga cccacacatg tccccctgc       480 ccagctcctg agctcttggg cggaccttcc gtgtttctgt tccccccaaa gcccaaggat      540
acccttatga tcagcagaac acccgaagtt acttgcgtgg tcgtggacgt ttctcacgaa      600
gatcctgaag tgaaattcaa ctggtacgtg gatggcgtgg aggtgcacaa tgctaagact      660
aagccccgtg aagagcagta caactctacc taccgggtcg tttcagtgct gactgttctc      720
catcaggact ggctcaacgg gaaggagtat aagtgcaagg tgtctaacaa ggcactgccc      780
gcacccatcg agaagaccat ttctaaggcc aagggtcaac cacgggagcc acaggtttac      840
acattgcctc ccagtcggga ggagatgaca aagaatcaag tgtcacttac atgtcttgtg      900
aagggcttct accctcaga catcgccgtg gagtgggaga gcaacggaca accagaaaac      960
aactacaaga ccacacctcc tgtgctcgat tcagatggtt ccttttttctt gtacagcaaa     1020 ctcaccgttg acaagagtcg gtggcagcaa ggaaatgtgt tcagctgttc tgtgatgcac     1080
gaggccctgc acaaccatta tacccaaaaa tctctcagcc tttctcccgg caag            1134

<210> SEQ ID NO 43
<211> LENGTH: 1317
<212> TYPE: DNA
<213> ORGANISM: Artificial Sequence
<220> FEATURE:
<223> OTHER INFORMATION: IL-15Ra-Fc

<400> SEQUENCE: 43
```

| | | |
|---|---|---|
| atggacatgc gggtgccagc ccagctgctg ggcctgttgc tgctgtggtt ccccggctct | 60 |
| cggtgcatca cctgccctcc acctatgtcc gtggaacacg cagacatctg ggtcaagagc | 120 |
| tacagcttgt actcccgcga gcgctacatt tgtaactctg gtttcaagcg taaagccggc | 180 |
| acctccagcc tgaccgagtg cgtgttgaac aaggccacca atgtcgccca ctggacaacc | 240 |
| ccaagtctca aatgcattcg cgaccctgcc ctggttcacc aacgcccagc gccaccatcc | 300 |
| acagtaacca ctgcaggcgt gaccccacag ccagagagcc tctccccttc tgcaaagag | 360 |
| ccagcagctt catctccaag ctcaaacaac acagcggcca acagcagc tattgtcccg | 420 |
| ggctcccagc tgatgccttc aaaatcacct tccacaggca ccacagagat cagcagtcat | 480 |
| gagtcctccc acggcacccc atctcagaca acagccaaga actgggaact cacagcatcc | 540 |
| gcctcccacc agccgccagg tgtgtatcca cagggccaca cgacaccac tggcggagga | 600 |
| ggctctgggg gcggaggaag cgaacctaag tcctctgata gacccacac atgtcccccc | 660 |
| tgcccagctc ctgagctctt gggcggacct tccgtgtttc tgttcccccc aaagcccaag | 720 |
| gataccctta tgatcagcag aacacccgaa gttacttgcg tggtcgtgga cgtttctcac | 780 |
| gaagatcctg aagtgaaatt caactggtac gtggatggcg tggaggtgca caatgctaag | 840 |
| actaagcccc gtgaagagca gtacaactct acctaccggg tcgtttcagt gctgactgtt | 900 |
| ctccatcagg actggctcaa cgggaaggag tataagtgca aggtgtctaa caaggcactg | 960 |
| cccgcaccca tcgagaagac catttctaag gccaagggtc aaccacggga gccacaggtt | 1020 |
| tacacattgc ctcccagtcg ggaggagatg acaaagaatc aagtgtcact acatgtctt | 1080 |
| gtgaagggct ctaccctc agacatcgcc gtggagtggg agagcaacgg acaaccagaa | 1140 |
| aacaactaca agaccacacc tcctgtgctc gattcagatg gttccttttt cttgtacagc | 1200 |
| aaactcaccg ttgacaagag tcggtggcag caaggaaatg tgttcagctg ttctgtgatg | 1260 |
| cacgaggccc tgcacaacca ttatacccaa aaatctctca gccttctcc cggcaag | 1317 |

<210> SEQ ID NO 44
<211> LENGTH: 1134
<212> TYPE: DNA
<213> ORGANISM: Artificial Sequence
<220> FEATURE:
<223> OTHER INFORMATION: Fc-IL-15

<400> SEQUENCE: 44

| | | |
|---|---|---|
| atggacatgc gggtgccagc ccagctgctg ggcctgttgc tgctgtggtt ccccggctct | 60 |
| cggtgcgaac ctaagtcctc tgataagacc cacacatgtc cccctgccc agctcctgag | 120 |
| ctcttgggcg gaccttccgt gtttctgttc ccccaaagc caaggatac ccttatgatc | 180 |
| agcagaacac ccgaagttac ttgcgtggtc gtggacgttt ctcacgaaga tcctgaagtg | 240 |
| aaattcaact ggtacgtgga tggcgtggag gtgcacaatg ctaagactaa gccccgtgaa | 300 |
| gagcagtaca actctaccta ccgggtcgtt tcagtgctga ctgttctcca tcaggactgg | 360 |
| ctcaacggga aggagtataa gtgcaaggtg tctaacaagg cactgcccgc acccatcgag | 420 |
| aagaccattt ctaaggccaa gggtcaacca cgggagccac aggtttacac attgcctccc | 480 |
| agtcgggagg agatgacaaa gaatcaagtg tcacttacat gtcttgtgaa gggcttctac | 540 |
| ccctcagaca tcgccgtgga gtgggagagc aacggacaac cagaaaacaa ctacaagacc | 600 |
| acacctcctg tgctcgattc agatggtccc ttttcttgt acagcaaaact caccgttgac | 660 |
| aagagtcggt ggcagcaagg aaatgtgttc agctgttctg tgatgcacga ggccctgcac | 720 |

```
aaccattata cccaaaaatc tctcagcctt tctcccggca agggcggagg aggctctggg        780
ggcggaggaa gcaactgggt gaatgtaatt agtgatttga aaaaaattga agatcttatt        840
caatctatgc atattgatgc tactttatat acggaaagtg atgttcaccc gagttgcaaa        900
gtaacagcaa tgaagtgctt tctcttggag ttacaagtta tttcacttga gtccggcgat        960
gcaagtattc atgatacagt agaaaatctg atcatcttag caaacaacag tttgtcttct       1020
aatgggaatg taacagaatc tggatgcaaa gaatgtgagg aactggagga aaaaaatatt       1080 aaagaattt tgcagagttt tgtacatatt gtccaaatgt tcatcaacac ttct              1134
```

<210> SEQ ID NO 45
<211> LENGTH: 1317
<212> TYPE: DNA
<213> ORGANISM: Artificial Sequence
<220> FEATURE:
<223> OTHER INFORMATION: Fc-IL15R alpha

<400> SEQUENCE: 45

```
atggacatgc gggtgccagc ccagctgctg ggcctgttgc tgctgtggtt ccccggctct         60
cggtgcgaac ctaagtcctc tgataagacc cacacatgtc cccctgccc agctcctgag        120 ctcttgggcg gaccttccgt gtttctgttc ccccaaagc caaggatac ccttatgatc         180 agcagaacac ccgaagttac ttgcgtggtc gtggacgttt ctcacgaaga tcctgaagtg        240
aaattcaact ggtacgtgga tggcgtgag gtgcacaatg ctaagactaa gccccgtgaa        300
gagcagtaca actctaccta ccgggtcgtt tcagtgctga ctgttctcca tcaggactgg        360
ctcaacggga aggagtataa gtgcaaggtg tctaacaagg cactgcccgc acccatcgag        420
aagaccattt ctaaggccaa gggtcaacca cgggagccac aggtttacac attgcctccc        480
agtcgggagg agatgacaaa gaatcaagtg tcacttacat gtcttgtgaa gggcttctac        540
ccctcagaca tcgccgtgga gtgggagagc aacggacaac agaaaacaa ctacaagacc         600 acacctcctg tgctcgattc agatggttcc ttttcttgt acagcaaact caccgttgac         660
aagagtcggt ggcagcaagg aaatgtgttc agctgttctg tgatgcacga ggccctgcac        720
aaccattata cccaaaaatc tctcagcctt tctcccggca agggcggagg aggctctggg        780
ggcggaggaa gcatcacctg ccctccacct atgtccgtgg aacacgcaga catctgggtc        840
aagagctaca gcttgtactc ccgcgagcgc tacatttgta actctggttt caagcgtaaa        900
gccggcacct ccagcctgac cgagtgcgtg ttgaacaagg ccaccaatgt cgcccactgg        960 acaacccaa gtctcaaatg cattcgcgac cctgccctgg ttcaccaacg cccagcgcca       1020
ccatccacag taaccactgc aggcgtgacc ccacagccag agagcctctc cccttctggc       1080
aaagagccag cagcttcatc tccaagctca acaacacag cggccacaac agcagctatt       1140
gtcccgggct cccagctgat gccttcaaaa tcaccttcca caggcaccac agagatcagc       1200
agtcatgagt cctcccacgg caccccatct cagacaacag ccaagaactg ggaactcaca       1260
gcatccgcct cccaccagcc gccaggtgtg tatccacagg gccacagcga caccact         1317
```

<210> SEQ ID NO 46
<211> LENGTH: 1134
<212> TYPE: DNA
<213> ORGANISM: Artificial Sequence
<220> FEATURE:
<223> OTHER INFORMATION: IL15-Fc-Knob

<400> SEQUENCE: 46

```
atggacatgc gggtgccagc ccagctgctg ggcctgttgc tgctgtggtt ccccggctct         60
```

```
cggtgcaact gggtgaatgt aattagtgat ttgaaaaaaa ttgaagatct tattcaatct    120
atgcatattg atgctacttt atatacggaa agtgatgttc acccgagttg caaagtaaca    180
gcaatgaagt gctttctctt ggagttacaa gttatttcac ttgagtccgg cgatgcaagt    240
attcatgata cagtagaaaa tctgatcatc ttagcaaaca acagtttgtc ttctaatggg    300
aatgtaacag aatctggatg caaagaatgt gaggaactgg aggaaaaaaa tattaaagaa    360
tttttgcaga gttttgtaca tattgtccaa atgttcatca acacttctgg cggaggaggc    420
tctgggggcg gaggaagcga acctaagtcc tctgataaga cccacacatg tcccccctgc    480
ccagctcctg agctcttggg cggaccttcc gtgtttctgt tccccccaaa gcccaaggat    540
acccttatga tcagcagaac acccgaagtt acttgcgtgg tcgtggacgt ttctcacgaa    600
gatcctgaag tgaaattcaa ctggtacgtg atggcgtgg aggtgcacaa tgctaagact    660
aagccccgtg aagagcagta caactctacc taccgggtcg tttcagtgct gactgttctc    720
catcaggact ggctcaacgg gaaggagtat aagtgcaagg tgtctaacaa ggcactgccc    780
gcacccatcg agaagaccat ttctaaggcc aagggtcaac cacgggagcc acaggtttac    840
acattgcctc ccagtcggga ggagatgaca aagaatcaag tgtcacttta ctgtcttgtg    900
aagggcttct accctcaga catcgccgtg gagtgggaga gcaacggaca accagaaaac    960
aactacaaga ccacacctcc tgtgctcgat tcagatggtt ccttttctt gtacagcaaa    1020 ctcaccgttg acaagagtcg gtggcagcaa ggaaatgtgt tcagctgttc tgtgatgcac    1080
gaggccctgc acaaccatta tacccaaaaa tctctcagcc tttctcccgg caag          1134
```

<210> SEQ ID NO 47
<211> LENGTH: 1134
<212> TYPE: DNA
<213> ORGANISM: Artificial Sequence
<220> FEATURE:
<223> OTHER INFORMATION: IL15-Fc-Hole

<400> SEQUENCE: 47

```
atggacatgc gggtgccagc ccagctgctg ggcctgttgc tgctgtggtt ccccggctct     60
cggtgcaact gggtgaatgt aattagtgat ttgaaaaaaa ttgaagatct tattcaatct    120
atgcatattg atgctacttt atatacggaa agtgatgttc acccgagttg caaagtaaca    180
gcaatgaagt gctttctctt ggagttacaa gttatttcac ttgagtccgg cgatgcaagt    240
attcatgata cagtagaaaa tctgatcatc ttagcaaaca acagtttgtc ttctaatggg    300
aatgtaacag aatctggatg caaagaatgt gaggaactgg aggaaaaaaa tattaaagaa    360
tttttgcaga gttttgtaca tattgtccaa atgttcatca acacttctgg cggaggaggc    420
tctgggggcg gaggaagcga acctaagtcc tctgataaga cccacacatg tcccccctgc    480
ccagctcctg agctcttggg cggaccttcc gtgtttctgt tccccccaaa gcccaaggat    540
acccttatga tcagcagaac acccgaagtt acttgcgtgg tcgtggacgt ttctcacgaa    600
gatcctgaag tgaaattcaa ctggtacgtg atggcgtgg aggtgcacaa tgctaagact    660
aagccccgtg aagagcagta caactctacc taccgggtcg tttcagtgct gactgttctc    720
catcaggact ggctcaacgg gaaggagtat aagtgcaagg tgtctaacaa ggcactgccc    780
gcacccatcg agaagaccat ttctaaggcc aagggtcaac cacgggagcc acaggtttac    840
acattgcctc ccagtcggga ggagatgaca aagaatcaag tgtcactta catgtcttgtg    900 aagggcttct accctcaga catcgccgtg gagtgggaga gcaacggaca accagaaaac    960
```

```
aactacaaga ccacacctcc tgtgctcgat tcagatggtt cctttttctt gaccagcaaa    1020
ctcaccgttg acaagagtcg gtggcagcaa ggaaatgtgt tcagctgttc tgtgatgcac    1080
gaggccctgc acaaccatta tacccaaaaa tctctcagcc tttctcccgg caag          1134
```

<210> SEQ ID NO 48
<211> LENGTH: 1104
<212> TYPE: DNA
<213> ORGANISM: Artificial Sequence
<220> FEATURE:
<223> OTHER INFORMATION: Fc-IL15-Knob

<400> SEQUENCE: 48

```
atggacatgc gggtgccagc ccagctgctg ggcctgttgc tgctgtggtt ccccggctct      60
cggtgcgaac ctaagtcctc tgataagacc cacacatgtc cccctgccc agctcctgag     120 ctcttgggcg gaccttccgt gtttctgttc cccccaaagc ccaaggatac ccttatgatc     180
agcagaacac ccgaagttac ttgcgtggtc gtggacgttt ctcacgaaga tcctgaagtg     240
aaattcaact ggtacgtgga tggcgtggag gtgcacaatg ctaagactaa gccccgtgaa     300
gagcagtaca actctaccta ccgggtcgtt tcagtgctga ctgttctcca tcaggactgg     360
ctcaacggga aggagtataa gtgcaaggtg tctaacaagg cactgccgc acccatcgag      420 aagaccattt ctaaggccaa gggtcaacca cgggagccac aggtttacac attgcctccc     480
agtcgggagg agatgacaaa gaatcaagtg tcactttact gtcttgtgaa gggcttctac     540
ccctcagaca tcgccgtgga gtgggagagc aacggacaac agaaaacaa ctacaagacc      600 acacctcctg tgctcgattc agatggtcc tttttcttgt acagcaaact caccgttgac      660
aagagtcggt ggcagcaagg aaatgtgttc agctgttctg tgatgcacga ggccctgcac     720
aaccattata cccaaaaatc tctcagcctt tctcccggca agaactgggt gaatgtaatt     780
agtgatttga aaaaattga agatctttat caatctatgc atattgatgc tactttatat     840
acggaaagtg atgttcaccc gagttgcaaa gtaacagcaa tgaagtgctt tctcttggag     900
ttacaagtta tttcacttga gtccggcgat gcaagtattc atgatacagt agaaaatctg     960
atcatcttag caaacaacag tttgtcttct aatgggaatg taacagaatc tggatgcaaa     1020
gaatgtgagg aactggagga aaaaaatatt aaagaatttt tgcagagttt tgtacatatt    1080
gtccaaatgt tcatcaacac ttct                                           1104
```

<210> SEQ ID NO 49
<211> LENGTH: 1104
<212> TYPE: DNA
<213> ORGANISM: Artificial Sequence
<220> FEATURE:
<223> OTHER INFORMATION: Fc-IL15-Hole

<400> SEQUENCE: 49

```
atggacatgc gggtgccagc ccagctgctg ggcctgttgc tgctgtggtt ccccggctct      60
cggtgcgaac ctaagtcctc tgataagacc cacacatgtc cccctgccc agctcctgag     120 ctcttgggcg gaccttccgt gtttctgttc cccccaaagc ccaaggatac ccttatgatc     180
agcagaacac ccgaagttac ttgcgtggtc gtggacgttt ctcacgaaga tcctgaagtg     240
aaattcaact ggtacgtgga tggcgtggag gtgcacaatg ctaagactaa gccccgtgaa     300
gagcagtaca actctaccta ccgggtcgtt tcagtgctga ctgttctcca tcaggactgg     360
ctcaacggga aggagtataa gtgcaaggtg tctaacaagg cactgccgc acccatcgag      420 aagaccattt ctaaggccaa gggtcaacca cgggagccac aggtttacac attgcctccc     480
```

```
agtcgggagg agatgacaaa gaatcaagtg tcacttacat gtcttgtgaa gggcttctac      540
ccctcagaca tcgccgtgga gtgggagagc aacggacaac cagaaaacaa ctacaagacc      600
acacctcctg tgctcgattc agatggttcc ttttcttga ccagcaaact caccgttgac       660
aagagtcggt ggcagcaagg aaatgtgttc agctgttctg tgatgcacga ggccctgcac      720
aaccattata cccaaaaatc tctcagcctt ctcccggca agaactgggt gaatgtaatt       780
agtgatttga aaaaaattga agatcttatt caatctatgc atattgatgc tactttatat     840
acggaaagtg atgttcaccc gagttgcaaa gtaacagcaa tgaagtgctt tctcttggag      900
ttacaagtta tttcacttga gtccggcgat gcaagtattc atgatacagt agaaaatctg      960
atcatcttag caaacaacag tttgtcttct aatgggaatg taacagaatc tggatgcaaa    1020
gaatgtgagg aactggagga aaaaaatatt aagaattttt gcagagtttt tgtacatatt    1080
gtccaaatgt tcatcaacac ttct                                           1104

<210> SEQ ID NO 50
<211> LENGTH: 1317
<212> TYPE: DNA
<213> ORGANISM: Artificial Sequence
<220> FEATURE:
<223> OTHER INFORMATION: IL15Ra-Fc-Knob

<400> SEQUENCE: 50
atggacatgc gggtgccagc ccagctgctg ggcctgttgc tgctgtggtt ccccggctct       60
cggtgcatca cctgccctcc acctatgtcc gtggaacacg cagacatctg ggtcaagagc      120
tacagcttgt actcccgcga gcgctacatt tgtaactctg gtttcaagcg taaagccggc      180
acctccagcc tgaccgagtg cgtgttgaac aaggccacca atgtcgccca ctggacaacc      240
ccaagtctca aatgcattcg cgaccctgcc ctggttcacc aacgcccagc gccaccatcc      300
acagtaacca ctgcaggcgt gaccccacag ccagagagcc tctcccttc tggcaaagag       360 ccagcagctt catctccaag ctcaaacaac acagcggcca acagcagc tattgtcccg        420 ggctcccagc tgatgccttc aaaatcacct tccacaggca ccacagagat cagcagtcat      480
gagtcctccc acggcacccc atctcagaca acagccaaga actgggaact cacagcatcc      540
gcctcccacc agccgccagg tgtgtatcca caggccaca gcgacaccac tggcggagga      600
ggctctgggg gcgaggaag cgaacctaag tcctctgata gacccacac atgtccccc         660 tgcccagctc ctgagctctt gggcggacct tccgtgttc tgttccccc aaagcccaag        720 gataccctta tgatcagcag aacacccgaa gttacttgcg tggtcgtgga cgtttctcac      780
gaagatcctg aagtgaaatt caactggtac gtggatggcg tggaggtgca caatgctaag      840
actaagcccc gtgaagagca gtacaactct acctaccggg tcgtttcagt gctgactgtt       900
ctccatcagg actggctcaa cggaaggag tataagtgca aggtgtctaa caaggcactg       960
cccgcaccca tcgagaagac catttctaag gccaagggtc aaccacggga gccacaggtt     1020
tacacattgc ctcccagtcg ggaggagatg acaaagaatc aagtgtcact ttactgtctt     1080
gtgaagggct tctaccctc agacatcgcc gtggagtggg agagcaacgg acaaccagaa      1140
aacaactaca gaccacacc tcctgtgctc gattcagatg gttccttttt cttgtacagc      1200
aaactcaccg ttgacaagag tcggtggcag caaggaaatg tgttcagctg ttctgtgatg     1260
cacgaggccc tgcacaacca ttatacccaa aaatctctca gcctttctcc cggcaag        1317

<210> SEQ ID NO 51
```

<211> LENGTH: 1317
<212> TYPE: DNA
<213> ORGANISM: Artificial Sequence
<220> FEATURE:
<223> OTHER INFORMATION: IL15Ra-Fc-Hole

<400> SEQUENCE: 51

| | |
|---|---|
| atggacatgc gggtgccagc ccagctgctg ggcctgttgc tgctgtggtt ccccggctct | 60 |
| cggtgcatca cctgccctcc acctatgtcc gtggaacacg cagacatctg ggtcaagagc | 120 |
| tacagcttgt actcccgcga gcgctacatt tgtaactctg gtttcaagcg taaagccggc | 180 |
| acctccagcc tgaccgagtg cgtgttgaac aaggccacca tgtcgccca ctggacaacc | 240 |
| ccaagtctca atgcattcg cgaccctgcc ctggttcacc aacgcccagc gccaccatcc | 300 |
| acagtaacca ctgcaggcgt gaccccacag ccagagagcc tctcccttc tggcaaagag | 360 |
| ccagcagctt catctccaag ctcaaacaac acagcggcca acagcagc tattgtcccg | 420 |
| ggctcccagc tgatgccttc aaaatcacct tccacaggca ccacagagat cagcagtcat | 480 |
| gagtcctccc acggcacccc atctcagaca acagccaaga ctgggaact cacagcatcc | 540 |
| gcctcccacc agccgccagg tgtgtatcca cagggccaca gcgacaccac tggcggagga | 600 |
| ggctctgggg gcgaggaag cgaacctaag tcctctgata gacccacac atgtccccc | 660 |
| tgcccagctc ctgagctctt gggcggacct tccgtgtttc tgttcccccc aaagcccaag | 720 |
| gataccctta tgatcagcag aacacccgaa gttacttgcg tggtcgtgga cgtttctcac | 780 |
| gaagatcctg aagtgaaatt caactggtac gtggatggcg tggaggtgca caatgctaag | 840 |
| actaagcccc gtgaagagca gtacaactct acctaccggg tcgtttcagt gctgactgtt | 900 |
| ctccatcagg actggctcaa cgggaaggag tataagtgca aggtgtctaa caaggcactg | 960 |
| cccgcaccca tcgagaagac catttctaag gccaagggtc aaccacggga gccacaggtt | 1020 |
| tacacattgc ctcccagtcg ggaggagatg acaaagaatc aagtgtcact tacatgtctt | 1080 |
| gtgaagggct ctaccccctc agacatcgcc gtggagtggg agagcaacgg acaaccagaa | 1140 |
| aacaactaca agaccacacc tcctgtgctc gattcagatg gttccttttt cttgaccagc | 1200 |
| aaactcaccg ttgacaagag tcggtggcag caaggaaatg tgttcagctg ttctgtgatg | 1260 |
| cacgaggccc tgcacaacca ttatacccaa aaatctctca gcctttctcc cggcaag | 1317 |

<210> SEQ ID NO 52
<211> LENGTH: 1287
<212> TYPE: DNA
<213> ORGANISM: Artificial Sequence
<220> FEATURE:
<223> OTHER INFORMATION: Fc-IL15R alpha-Knob

<400> SEQUENCE: 52

| | |
|---|---|
| atggacatgc gggtgccagc ccagctgctg ggcctgttgc tgctgtggtt ccccggctct | 60 |
| cggtgcgaac ctaagtcctc tgataagacc cacacatgtc cccctgccc agctcctgag | 120 |
| ctcttgggcg gaccttccgt gtttctgttc cccccaaagc caaggatac ccttatgatc | 180 |
| agcagaacac ccgaagttac ttgcgtggtc gtggacgttt ctcacgaaga tcctgaagtg | 240 |
| aaattcaact ggtacgtgga tggcgtggag gtgcacaatg ctaagactaa gcccgtgaa | 300 |
| gagcagtaca actctaccta ccgggtcgtt tcagtgctga ctgttctcca tcaggactgg | 360 |
| ctcaacggga aggagtataa gtgcaaggtg tctaacaagg cactgccgc acccatcgag | 420 |
| aagaccattt ctaaggccaa gggtcaacca cgggagccac aggtttacac attgcctccc | 480 |
| agtcgggagg agatgacaaa gaatcaagtg tcactttact gtcttgtgaa gggcttctac | 540 |

```
ccctcagaca tcgccgtgga gtgggagagc aacggacaac cagaaaacaa ctacaagacc    600
acacctcctg tgctcgattc agatggttcc ttttcttgt acagcaaact caccgttgac     660
aagagtcggt ggcagcaagg aaatgtgttc agctgttctg tgatgcacga ggccctgcac    720
aaccattata cccaaaaatc tctcagcctt tctcccggca agatcacctg ccctccacct    780
atgtccgtgg aacacgcaga catctgggtc aagagctaca gcttgtactc ccgcgagcgc    840
tacatttgta actctggttt caagcgtaaa gccggcacct ccagcctgac cgagtgcgtg    900
ttgaacaagg ccaccaatgt cgcccactgg acaaccccaa gtctcaaatg cattcgcgac    960
cctgccctgg ttcaccaacg cccagcgcca ccatccacag taaccactgc aggcgtgacc   1020
ccacagccag agagcctctc cccttctggc aaagagccag cagcttcatc tccaagctca   1080
aacaacacag cggccacaac agcagctatt gtcccgggct cccagctgat gccttcaaaa   1140
tcaccttcca caggcaccac agagatcagc agtcatgagt cctcccacgg cacccc atct   1200 cagacaacag ccaagaactg gaactcaca gcatccgcct cccaccagcc gccaggtgtg    1260
tatccacagg gccacagcga caccact                                       1287

<210> SEQ ID NO 53
<211> LENGTH: 1287
<212> TYPE: DNA
<213> ORGANISM: Artificial Sequence
<220> FEATURE:
<223> OTHER INFORMATION: Fc-IL15R alpha-Hole

<400> SEQUENCE: 53
atggacatgc gggtgccagc ccagctgctg ggcctgttgc tgctgtggtt ccccggctct     60
cggtgcgaac ctaagtcctc tgataagacc cacacatgtc cccctgccc agctcctgag    120 ctcttgggcg gaccttccgt gtttctgttc cccccaaagc ccaaggatac ccttatgatc    180
agcagaacac ccgaagttac ttgcgtggtc gtggacgttt ctcacgaaga tcctgaagtg    240
aaattcaact ggtacgtgga tggcgtggag gtgcacaatg ctaagactaa gccccgtgaa    300
gagcagtaca actctaccta ccgggtcgtt tcagtgctga ctgttctcca tcaggactgg    360
ctcaacggga aggagtataa gtgcaaggtg tctaacaagg cactgcccgc acccatcgag    420
aagaccattt ctaaggccaa gggtcaacca cgggagccac aggtttacac attgcctccc    480
agtcgggagg agatgacaaa gaatcaagtg tcacttacat gtcttgtgaa gggcttctac    540
ccctcagaca tcgccgtgga gtgggagagc aacggacaac cagaaaacaa ctacaagacc    600
acacctcctg tgctcgattc agatggttcc ttttcttga ccagcaaact caccgttgac     660
aagagtcggt ggcagcaagg aaatgtgttc agctgttctg tgatgcacga ggccctgcac    720
aaccattata cccaaaaatc tctcagcctt tctcccggca agatcacctg ccctccacct    780
atgtccgtgg aacacgcaga catctgggtc aagagctaca gcttgtactc ccgcgagcgc    840
tacatttgta actctggttt caagcgtaaa gccggcacct ccagcctgac cgagtgcgtg    900
ttgaacaagg ccaccaatgt cgcccactgg acaaccccaa gtctcaaatg cattcgcgac    960
cctgccctgg ttcaccaacg cccagcgcca ccatccacag taaccactgc aggcgtgacc   1020
ccacagccag agagcctctc cccttctggc aaagagccag cagcttcatc tccaagctca   1080
aacaacacag cggccacaac agcagctatt gtcccgggct cccagctgat gccttcaaaa   1140
tcaccttcca caggcaccac agagatcagc agtcatgagt cctcccacgg cacccc atct   1200 cagacaacag ccaagaactg gaactcaca gcatccgcct cccaccagcc gccaggtgtg    1260
```

```
<210> SEQ ID NO 54
<211> LENGTH: 762
<212> TYPE: DNA
<213> ORGANISM: Artificial Sequence
<220> FEATURE:
<223> OTHER INFORMATION: Fc-Knob

<400> SEQUENCE: 54
atggacatgc gggtgccagc ccagctgctg ggcctgttgc tgctgtggtt ccccggctct    60
cggtgcgaac ctaagtcctc tgataagacc cacacatgtc cccctgccc agctcctgag   120
ctcttgggcg gaccttccgt gtttctgttc ccccaaagc ccaaggatac ccttatgatc   180
agcagaacac ccgaagttac ttgcgtggtc gtggacgttt ctcacgaaga tcctgaagtg   240
aaattcaact ggtacgtgga tggcgtggag gtgcacaatg ctaagactaa gccccgtgaa   300
gagcagtaca actctaccta ccgggtcgtt tcagtgctga ctgttctcca tcaggactgg   360
ctcaacggga aggagtataa gtgcaaggtg tctaacaagg cactgcccgc acccatcgag   420
aagaccattt ctaaggccaa gggtcaacca cgggagccac aggtttacac attgcctccc   480
agtcgggagg agatgacaaa gaatcaagtg tcactttact gtcttgtgaa gggcttctac   540
ccctcagaca tcgccgtgga gtgggagagc aacggacaac agaaaacaa ctacaagacc   600
acacctcctg tgctcgattc agatggttcc ttttcttgt acagcaaact caccgttgac   660
aagagtcggt ggcagcaagg aaatgtgttc agctgttctg tgatgcacga ggccctgcac   720
aaccattata cccaaaaatc tctcagcctt tctcccggca ag                      762

<210> SEQ ID NO 55
<211> LENGTH: 762
<212> TYPE: DNA
<213> ORGANISM: Artificial Sequence
<220> FEATURE:
<223> OTHER INFORMATION: Fc-Hole

<400> SEQUENCE: 55
atggacatgc gggtgccagc ccagctgctg ggcctgttgc tgctgtggtt ccccggctct    60
cggtgcgaac ctaagtcctc tgataagacc cacacatgtc cccctgccc agctcctgag   120
ctcttgggcg gaccttccgt gtttctgttc ccccaaagc ccaaggatac ccttatgatc   180
agcagaacac ccgaagttac ttgcgtggtc gtggacgttt ctcacgaaga tcctgaagtg   240
aaattcaact ggtacgtgga tggcgtggag gtgcacaatg ctaagactaa gccccgtgaa   300
gagcagtaca actctaccta ccgggtcgtt tcagtgctga ctgttctcca tcaggactgg   360
ctcaacggga aggagtataa gtgcaaggtg tctaacaagg cactgcccgc acccatcgag   420
aagaccattt ctaaggccaa gggtcaacca cgggagccac aggtttacac attgcctccc   480
agtcgggagg agatgacaaa gaatcaagtg tcacttacat gtcttgtgaa gggcttctac   540
ccctcagaca tcgccgtgga gtgggagagc aacggacaac agaaaacaa ctacaagacc   600
acacctcctg tgctcgattc agatggttcc ttttcttga ccagcaaact caccgttgac   660
aagagtcggt ggcagcaagg aaatgtgttc agctgttctg tgatgcacga ggccctgcac   720
aaccattata cccaaaaatc tctcagcctt tctcccggca ag                      762

<210> SEQ ID NO 56
<211> LENGTH: 1155
<212> TYPE: DNA
<213> ORGANISM: Artificial Sequence
```
tatccacagg gccacagcga caccact                                       1287

<220> FEATURE:
<223> OTHER INFORMATION: Fc-Knob(M)-IL-15Ra-nucleotide sequence encoding the precursor of protein sequence 45

<400> SEQUENCE: 56

| | | |
|---|---|---|
| atggagtttg ggctgagctg gcttttctt gtcgcgattc ttaagggtgt ccagtgcgag | 60 |
| cccaaatcta gtgacaaaac tcacacgtcc ccaccgtccc cagcacctga actcctgggg | 120 |
| ggaccgtcag tcttcctctt cccccccaaaa cccaaggaca ccctcatgat ctcccggacc | 180 |
| cctgaggtca catgcgtggt ggtggacgtg agccacgaag accctgaggt caagttcaac | 240 |
| tggtacgtgg acggcgtgga ggtgcataat gccaagacaa agccgcggga agagcagtac | 300 |
| aacagcacgt accgtgtggt cagcgtcctc accgtcctgc accaggactg gctgaatggc | 360 |
| aaggagtaca agtgcaaggt ctccaacaaa gccctcccag cccccatcga aaaaccatc | 420 |
| tccaaagcca agggcagcc cgagaaccca caggtgtaca ccctgccccc atgcgggat | 480 |
| gagctgacca gaaccaggt cagcctgtgg tgcctggtca aaggcttcta tcccagcgac | 540 |
| atcgccgtgg agtgggagag caatgggcag ccggagaaca actacaagac cacgcctccc | 600 |
| gtgctggact ccgacggctc cttcttcctc tacagcaagc tcaccgtgga caagagcagg | 660 |
| tggcagcagg ggaacgtctt ctcatgctcc gtgatgcatg aggctctgca caaccactac | 720 |
| acgcagaaga gcctctccct gtctccgggt aaaggcggag gaggctctgg cggtggtggc | 780 |
| agtggtggcg gagggtcagg aggtggtgga agcaactggg tgaatgtaat tagtgatttg | 840 |
| aaaaaaattg aagatcttat tcaatctatg catattgatg ctactttata tacggaaagt | 900 |
| gatgttcacc cgagttgcaa agtaacagca atgaagtgct ttctcttgga gttacaagtt | 960 |
| atttcacttg agtccggcga tgcaagtatt catgatacag tagaaaatct gatcatctta | 1020 |
| gcaaacaaca gtttgtcttc taatgggaat gtaacagaat ctggatgcaa agaatgtgag | 1080 |
| gaactggagg aaaaaaatat taagaatttt tgcagagtt ttgtacatat tgtccaaatg | 1140 |
| ttcatcaaca cttct | 1155 |

<210> SEQ ID NO 57
<211> LENGTH: 1134
<212> TYPE: DNA
<213> ORGANISM: Artificial Sequence
<220> FEATURE:
<223> OTHER INFORMATION: IL-15-Fc-Knob(M), nucleotide sequence encoding the precursor of protein sequence 46

<400> SEQUENCE: 57

| | | |
|---|---|---|
| atggacatgc gggtgccagc ccagctgctg ggcctgttgc tgctgtggtt ccccggctct | 60 |
| cggtgcaact gggtgaatgt aattagtgat ttgaaaaaaa ttgaagatct tattcaatct | 120 |
| atgcatattg atgctacttt atatacggaa agtgatgttc acccgagttg caaagtaaca | 180 |
| gcaatgaagt gctttctctt ggagttacaa gttatttcac ttgagtccgg cgatgcaagt | 240 |
| attcatgata cagtagaaaa tctgatcatc ttagcaaaca acagtttgtc ttctaatggg | 300 |
| aatgtaacag aatctggatg caaagaatgt gaggaactgg aggaaaaaaa tattaaagaa | 360 |
| tttttgcaga gttttgtaca tattgtccaa atgttcatca cacttctgg cggaggaggc | 420 |
| tctgggggcg gaggatccga gcccaaatct agtgacaaaa ctcacacgag cccaccgagc | 480 |
| ccagcacctg aactcctggg gggaccgtca gtcttcctct tccccccaaa acccaaggac | 540 |
| accctcatga tctcccggac ccctgaggtc acatgcgtgg tggtggacgt gagccacgaa | 600 |
| gaccctgagg tcaagttcaa ctggtacgtg gacggcgtgg aggtgcataa tgccaagaca | 660 |

| | |
|---|---|
| aagccgcggg aagagcagta caacagcacg taccgtgtgg tcagcgtcct caccgtcctg | 720 |
| caccaggact ggctgaatgg caaggagtac aagtgcaagg tctccaacaa agccctccca | 780 |
| gcccccatcg agaaaaccat ctccaaagcc aagggcagc cccgagaacc acaggtgtac | 840 |
| accctgcccc catgccggga tgagctgacc aagaaccagg tcagcctgtg gtgcctggtc | 900 |
| aaaggcttct atcccagcga catcgccgtg gagtgggaga gcaatgggca gccggagaac | 960 |
| aactacaaga ccacgcctcc cgtgctggac tccgacggct ccttcttcct ctacagcaag | 1020 |
| ctcaccgtgg acaagagcag gtggcagcag gggaacgtct tctcatgctc cgtgatgcat | 1080 |
| gaggctctgc acaaccacta cacgcagaag agcctctccc tgtctccggg taaa | 1134 |

<210> SEQ ID NO 58
<211> LENGTH: 1008
<212> TYPE: DNA
<213> ORGANISM: Artificial Sequence
<220> FEATURE:
<223> OTHER INFORMATION: Fc-Hole(M)-IL-15Ra-sushi 65, nucleotide
      sequence encoding the precursor of protein sequence 47

<400> SEQUENCE: 58

| | |
|---|---|
| atggagtttg ggctgagctg gctttttctt gtcgcgattc ttaagggtgt ccagtgcgag | 60 |
| cccaaatcta gtgacaaaac tcacacgtcc ccaccgtccc cagcacctga actcctgggg | 120 |
| ggaccgtcag tcttcctctt ccccccaaaa cccaaggaca ccctcatgat ctcccggacc | 180 |
| cctgaggtca catgcgtggt ggtggacgtg agccacgaag accctgaggt caagttcaac | 240 |
| tggtacgtgg acggcgtgga ggtgcataat gccaagacaa agccgcggga agagcagtac | 300 |
| aacagcacgt accgtgtggt cagcgtcctc accgtcctgc accaggactg gctgaatggc | 360 |
| aaggagtaca agtgcaaggt ctccaacaaa gccctcccag cccccatcga gaaaaccatc | 420 |
| tccaaagcca agggcagccc cgagaaccag gtgtgcaccc tgcccccatc ccgggat | 480 |
| gagctgacca agaaccaggt cagcctgagc tgcgccgtca aaggcttcta tcccagcgac | 540 |
| atcgccgtgg agtgggagag caatgggcag ccggagaaca actacaagac cacgcctccc | 600 |
| gtgctggact ccgacggctc cttcttcctc gtgagcaagc tcaccgtgga caagagcagg | 660 |
| tggcagcagg ggaacgtctt ctcatgctcc gtgatgcatg aggctctgca caaccactac | 720 |
| acgcagaaga gcctctccct gtctccgggt aaaggcggag gaggctctgg cggtggtggc | 780 |
| agtggtggcg gagggtcagg aggtggtgga agcatcacct gccctccacc tatgtccgtg | 840 |
| gaacacgcag acatctgggt caagagctac agcttgtact cccgcgagcg ctacatttgt | 900 |
| aactctggtt tcaagcgtaa agccggcacc tccagcctga ccgagtgcgt gttgaacaag | 960 |
| gccaccaatg tcgcccactg gacaacccca gtctcaaat gcattcgc | 1008 |

<210> SEQ ID NO 59
<211> LENGTH: 1017
<212> TYPE: DNA
<213> ORGANISM: Artificial Sequence
<220> FEATURE:
<223> OTHER INFORMATION: IL15Ra-sushi(65)-Fc-Hole(M), nucleotide
      sequence encoding the precursor of protein sequence 48

<400> SEQUENCE: 59

| | |
|---|---|
| atggacatgc gggtgccagc ccagctgctg ggcctgttgc tgctgtggtt ccccggctct | 60 |
| cggtgcatca cctgccctcc acctatgtcc gtggaacacg cagacatctg gtcaagagc | 120 |
| tacagcttgt actcccgcga gcgctacatt tgtaactctg gtttcaagcg taaagccggc | 180 |
| acctccagcc tgaccgagtg cgtgttgaac aaggccacca atgtcgccca ctggacaacc | 240 |

```
ccaagtctca aatgcattcg cggaggggggt ggcagcggcg ggggaggttc aggcggaggt      300
gggtctggag gcggtggatc cgagcccaaa tctagtgaca aaactcacac gtccccaccg      360
tccccagcac ctgaactcct ggggggaccg tcagtcttcc tcttcccccc aaaacccaag      420
gacaccctca tgatctcccg gacccctgag gtcacatgcg tggtggtgga cgtgagccac      480
gaagaccctg aggtcaagtt caactggtac gtggacggcg tggaggtgca taatgccaag      540
acaaagccgc gggaagagca gtacaacagc acgtaccgtg tggtcagcgt cctcaccgtc      600
ctgcaccagg actggctgaa tggcaaggag tacaagtgca aggtctccaa caaagccctc      660
ccagccccca tcgagaaaac catctccaaa gccaaagggc agccccgaga accacaggtg      720
tgcaccctgc cccatcccg gatgagctg accaagaacc aggtcagcct gagctgcgcc      780
gtcaaaggct tctatcccag cgacatcgcc gtggagtggg agagcaatgg gcagccggag      840
aacaactaca agaccacgcc tcccgtgctg gactccgacg gctccttctt cctcgtgagc      900
aagctcaccg tggacaagag caggtggcag caggggaacg tcttctcatg ctccgtgatg      960
catgaggctc tgcacaacca ctacacgcag aagagcctct ccctgtctcc gggtaaa        1017
```

<210> SEQ ID NO 60
<211> LENGTH: 1041
<212> TYPE: DNA
<213> ORGANISM: Artificial Sequence
<220> FEATURE:
<223> OTHER INFORMATION: IL-15Ra-sushi 73 -Fc-Hole, nucleotide sequence
      encoding the precursor of protein sequence 49

<400> SEQUENCE: 60

```
atggacatgc gggtgccagc ccagctgctg ggcctgttgc tgctgtggtt ccccggctct       60
cggtgcatca ccctgccctc acctatgtcc gtggaacacg cagacatctg ggtcaagagc      120
tacagcttgt actcccgcga gcgctacatt tgtaactctg gtttcaagcg taaagccggc      180
acctccagcc tgaccgagtg cgtgttgaac aaggccacca tgtcgcccca ctggacaacc      240
ccaagtctca aatgcattcg cgaccctgcc ctggttcacc aacgctccgg cggatcagga      300
ggtggtggca gcgggggtgg ttccggtgga gggggctcct gcaggaacc taagtcctct      360 gataagaccc acacatgtcc ccctgcccca gctcctgagc tcttgggcgg accttccgtg      420
tttctgttcc ccccaaagcc caaggatacc cttatgatca gcagaacacc cgaagttact      480
tgcgtggtcg tggacgtttc tcacgaagat cctgaagtga attcaactg gtacgtggat      540 ggcgtggagg tgcacaatgc taagactaag ccccgtgaag agcagtacaa ctctacctac      600
cgggtcgttt cagtgctgac tgttctccat caggactggc tcaacgggaa ggagtataag      660
tgcaaggtgt ctaacaaggc actgcccgca cccatcgaga agaccatttc taaggccaag      720
ggtcaaccac gggagccaca ggtttacaca ttgcctccca gtcgggagga gatgacaaag      780
aatcaagtgt cacttacatg tcttgtgaag ggcttctacc cctcagacat cgccgtggag      840
tgggagagca acggacaacc agaaaacaac tacaagacca cacctcctgt gctcgattca      900
gatggttcct ttttcttgac cagcaaactc accgttgaca gagtcggtg gcagcaagga      960 aatgtgttca gctgttctgt gatgcacgag gccctgcaca accattatac ccaaaaatct     1020
ctcagccttt ctcccggcaa g                                                 1041
```

<210> SEQ ID NO 61
<211> LENGTH: 1017
<212> TYPE: DNA
<213> ORGANISM: Artificial Sequence
<220> FEATURE:
<223> OTHER INFORMATION: IL-15Ra-sushi 65 -Fc-Hole, nucleotide sequence
      encoding the precursor of protein sequence 50

<400> SEQUENCE: 61

| | | |
|---|---|---|
| atggacatgc gggtgccagc ccagctgctg ggcctgttgc tgctgtggtt ccccggctct | 60 |
| cggtgcatca cctgccctcc acctatgtcc gtggaacacg cagacatctg ggtcaagagc | 120 |
| tacagcttgt actcccgcga gcgctacatt tgtaactctg gtttcaagcg taaagccggc | 180 |
| acctccagcc tgaccgagtg cgtgttgaac aaggccacca atgtcgccca ctggacaacc | 240 |
| ccaagtctca aatgcattcg ctccggcgga tcaggaggtg gtggcagcgg gggtggttcc | 300 |
| ggtggagggg gctccttgca ggaacctaag tcctctgata gacccacac atgtccccc | 360 |
| tgcccagctc ctgagctctt gggcggacct tccgtgtttc tgttcccccc aaagcccaag | 420 |
| gataccctta tgatcagcag aacacccgaa gttacttgcg tggtcgtgga cgtttctcac | 480 |
| gaagatcctg aagtgaaatt caactggtac gtggatggcg tggaggtgca caatgctaag | 540 |
| actaagcccc gtgaagagca gtacaactct acctaccggg tcgtttcagt gctgactgtt | 600 |
| ctccatcagg actggctcaa cgggaaggag tataagtgca aggtgtctaa caaggcactg | 660 |
| cccgcaccca tcgagaagac catttctaag gccaagggtc aaccacggga gccacaggtt | 720 |
| tacacattgc ctcccagtcg ggaggagatg acaaagaatc aagtgtcact tacatgtctt | 780 |
| gtgaagggct ctaccccctc agacatcgcc gtggagtggg agagcaacgg acaaccagaa | 840 |
| aacaactaca agaccacacc tcctgtgctc gattcagatg gttcctttt cttgaccagc | 900 |
| aaactcaccg ttgacaagag tcggtggcag caaggaaatg tgttcagctg ttctgtgatg | 960 |
| cacgaggccc tgcacaacca ttatacccaa aaatctctca gcctttctcc cggcaag | 1017 |

<210> SEQ ID NO 62
<211> LENGTH: 1080
<212> TYPE: DNA
<213> ORGANISM: Artificial Sequence
<220> FEATURE:
<223> OTHER INFORMATION: IL-15Ra-sushi 86 -Fc-Hole, nucleotide sequence
      encoding the precursor of protein sequence 51

<400> SEQUENCE: 62

| | | |
|---|---|---|
| atggacatgc gggtgccagc ccagctgctg ggcctgttgc tgctgtggtt ccccggctct | 60 |
| cggtgcatca cctgccctcc acctatgtcc gtggaacacg cagacatctg ggtcaagagc | 120 |
| tacagcttgt actcccgcga gcgctacatt tgtaactctg gtttcaagcg taaagccggc | 180 |
| acctccagcc tgaccgagtg cgtgttgaac aaggccacca atgtcgccca ctggacaacc | 240 |
| ccaagtctca aatgcattcg cgaccctgcc ctggttcacc aacgcccagc gccaccatcc | 300 |
| acagtaacca ctgcaggcgt gacctccggc ggatcaggag tggtggcag cggggggtggt | 360 |
| tccggtggag ggggctcctt gcaggaacct aagtcctctg ataagaccca cacatgtccc | 420 |
| ccctgcccag ctcctgagct cttgggcgga ccttccgtgt ttctgttccc cccaaagccc | 480 |
| aaggataccc ttatgatcag cagaacaccc gaagttactt gcgtggtcgt ggacgtttct | 540 |
| cacgaagatc ctgaagtgaa attcaactgg tacgtggatg gcgtggaggt gcacaatgct | 600 |
| aagactaagc cccgtgaaga gcagtacaac tctacctacc gggtcgtttc agtgctgact | 660 |
| gttctccatc aggactggct caacgggaag gagtataagt gcaaggtgtc taacaaggca | 720 |
| ctgcccgcac ccatcgagaa gaccatttct aaggccaagg gtcaaccacg ggagccacag | 780 |
| gtttacacat tgcctcccag tcgggaggag atgacaaaga atcaagtgtc acttacatgt | 840 |

-continued

```
cttgtgaagg gcttctaccc ctcagacatc gccgtggagt gggagagcaa cggacaacca    900
gaaaacaact acaagaccac acctcctgtg ctcgattcag atggttcctt tttcttgacc    960
agcaaactca ccgttgacaa gagtcggtgg cagcaaggaa atgtgttcag ctgttctgtg   1020
atgcacgagg ccctgcacaa ccattatacc caaaaatctc tcagcctttc tcccggcaag   1080
```

<210> SEQ ID NO 63
<211> LENGTH: 1098
<212> TYPE: DNA
<213> ORGANISM: Artificial Sequence
<220> FEATURE:
<223> OTHER INFORMATION: IL-15Ra-sushi 102 -Fc-Hole nucleotide sequence encoding the precursor of protein sequence 52

<400> SEQUENCE: 63

```
atggacatgc gggtgccagc ccagctgctg ggcctgttgc tgctgtggtt ccccggctct    60
cggtgcatca cctgccctcc acctatgtcc gtggaacacg cagacatctg ggtcaagagc   120
tacagcttgt actcccgcga gcgctacatt tgtaactctg gtttcaagcg taaagccggc   180
acctccagcc tgaccgagtg cgtgttgaac aaggccacca atgtcgccca ctggacaacc   240
ccaagtctca aatgcattcg cgaccctgcc ctggttcacc aacgccagc gccaccatcc   300 acagtaacca ctgcaggcgt gaccccacag ccagagagcc tctccccttc tggcaaagag   360
ccagcagctt caggcggagg aggctctggg ggcggaggaa gcgaacctaa gtcctctgat   420
aagacccaca catgtccccc ctgcccagct cctgagctct gggcggaccc ttccgtgttt   480
ctgttccccc caaagcccaa ggataccctt atgatcagca gaacacccga agttacttgc   540
gtggtcgtgg acgtttctca cgaagatcct gaagtgaaat tcaactggta cgtggatggc   600
gtggaggtgc acaatgctaa gactaagccc gtgaagagc agtacaactc tacctaccgg   660
gtcgtttcag tgctgactgt tctccatcag gactggctca cgggaagga gtataagtgc   720 aaggtgtcta acaaggcact gcccgcaccc atcgagaaga ccatttctaa ggccaagggt   780
caaccacggg agccacaggt ttacacattg cctcccagtc gggaggagat gacaaagaat   840
caagtgtcac ttacatgtct tgtgaagggc ttctacccct cagacatcgc cgtggagtgg   900
gagagcaacg gacaaccaga aaacaactac aagaccacac tcctgtgct cgattcagat   960 ggttcctttt tcttgaccag caaactcacc gttgacaaga gtcggtggca gcaaggaaat  1020
gtgttcagct gttctgtgat gcacgaggcc ctgcacaacc attataccca aaaatctctc  1080
agcctttctc ccggcaag                                                1098
```

IL-15 HETERODIMERIC PROTEIN AND USES THEREOF

CROSS-REFERENCE TO RELATED APPLICATION

This application is a Section 371 of International Application No. PCT/CN2014/094947, filed Dec. 25, 2014, which was published in the Chinese language on Jul. 16, 2015, under International Publication No. WO 2015/103928 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "688452_30US_Sequence_Listing," creation date of Jun. 30, 2016, and having a size of 133 kB. The sequence listing submitted via EFS-Web is part of the specification and is herein incorporated by reference in its entirety.

FIELD OF THE INVENTION

The present invention relates to an IL-15 heterodimeric protein and uses thereof, and further relates to an IL-15/IL-15Rα heterodimeric protein complex, and its use as a therapeutic agent, particularly as a therapeutic agent for cancer and autoimmune disease.

BACKGROUND

Interleukin 15 (IL-15), discovered by Grabstein et al. in 1994, is a cytokine of about 12-14 kD, which plays a role in the normal immune response in organisms, such as promoting the proliferation of T cells, B cells and natural killer (NK) cells.

IL-15 is a member of the small four α-helix bundle family of cytokines. IL-15 needs to bind with its receptor to exert its biological activity. IL-15 receptor consists of three receptor subunits: IL-15 receptor α (IL-15Rα), IL-2 receptor β (IL-2Rβ, also known as IL-15Rβ or CD122) and γc (also known as CD132). IL-15Rα contains a Sushi domain which is capable of binding with IL-15, and is essential for biological functions of IL-15 after binding.

Recently, it was found that the complex formed by IL-15 and its receptor IL-15Rα can significantly enhance the biological activity of IL-15. Studies indicated that the complex formed by IL-15 and soluble IL-15Rα receptor is significantly superior to IL-15 alone in stimulating the proliferation of memory CD8+ T lymphocytes and NT/NKT cells. IL-15/IL-15Rα complex is more than 10 times stronger than IL-15 alone in stimulating proliferation of memory CD8+ T cells and in maintaining their survival. The mechanism may be related to cis presentation.

Since it has been demonstrated that IL-15 is expected to be useful in the field of tumor immunotherapy, the National Institutes of Health (NIH) first began investigating IL-15 treatment in the tumor area, and tried to push it into Phase I clinicals. However, IL-15 has the disadvantages of small molecular weight, short in vivo half-life, hardly-controlled repeated dosage, and is likely to cause systemic immune side effects. There is an urgent need to find an approach which can increase the in vivo half-life, and promote or enhance the biological activity of IL-15 in vivo. There are many domestic and foreign companies or research institutions engaging in research related to IL-15 immunotherapy. For example, Chinese Patent CN100334112C (Shanghai Haixin Biotechnology Co., Ltd.) relates to IL-15-hIgG4Fc homodimeric protein in anti-microbial infection treatment; Chines Patent Application CN1942481A (Switzerland F. Hoffmann-LaRoche AG) relates to IL-15-Fc fusion expression system and its use; and Chinese Patent CN101360827B (French Institute of Health and Medical Research) relates to IL-15Rα (sushi+domain)-IL-15 fusion protein and its application in cancer treatment. Heterodimeric molecules of the present application show better stability, prolonged in vivo half-life and improved biological activity by increasing intramolecular interactions. On the basis of the molecular design in the present application, targeting immune cytokines can be generated by fusing and inserting functional polypeptides via methods well known in the field. The present disclosure also relates to the application of targeting immune cytokines in cancer and autoimmune disease therapy.

SUMMARY OF THE INVENTION

The present invention provides a protein molecule having prolonged in vivo half-life, increased in vitro activity and significant anti-tumor activity designed and prepared via genetic engineering methods.

The present invention provides an IL-15 heterodimeric protein comprising:

protein (I) and protein (II);

wherein the protein (I) is recombinantly produced by combining IL-15 or a variant thereof with a first Fc variant;

protein (II) is a second Fc variant, or protein (II) is recombinantly produced by combining IL-15Rα or a variant thereof with a second Fc variant; and protein (I) and protein (II) form a stable heterodimeric protein by an interaction between the first Fc variant and the second Fc variant.

As described above, the term "recombinantly produced" means obtained by expressing recombinants of different proteins produced by genetic engineering methods.

In a preferred embodiment of the present invention, the first Fc variant and the second Fc variant are linked to the C-terminus of IL-15 and IL-15Rα.

In one embodiment of the present invention, provided is an IL-15 heterodimeric protein, wherein the sequence of IL-15 is SEQ ID NO: 1.

In a preferred embodiment of the present invention, provided is an IL-15 heterodimeric protein, wherein the protein (II) is the second Fc variant.

In one embodiment of the present invention, provided is an IL-15 heterodimeric protein, wherein the protein (II) is recombinantly produced by combining IL-15Rα or its variant with a second Fc variant.

In one embodiment of the present invention, provided is an IL-15 heterodimeric protein, wherein the IL-15Rα variant is an extracellular domain portion of IL-15Rα or a functional fragment thereof, the functional fragment is preferably a truncated form of the IL-15Rα extracellular domain portion with 65 to 120 amino acids, more preferably a truncated form with 65 to 102 amino acids.

In one embodiment of the present invention, provided is an IL-15 heterodimeric protein, wherein the sequence of the IL-15Rα variant is selected from the group consisting of SEQ ID NOs: 2-7.

In one embodiment of the present invention, provided is an IL-15 heterodimeric protein, wherein the sequence of the IL-15Rα variant is selected from the group consisting of SEQ ID NOs: 3-7.

In one embodiment of the present invention, provided is an IL-15 heterodimeric protein, wherein the first Fc variant and the second Fc variant are respectively selected from Knob modified Fc and Hole modified Fc; or the first Fc variant and the second Fc variant are respectively selected from Hole modified Fc and Knob modified Fc. "Knob/Hole" mode helps the first Fc variant and the second Fc variant to form a heterodimeric protein after modification. When the first Fc variant is a Knob modified Fc, the second Fc variant is a Hole modified Fc; or when the second Fc variant is a Knob modified Fc, the first Fc variant is a Hole modified Fc.

In one embodiment of the present invention, provided is an IL-15 heterodimeric protein, wherein the sequence of the first Fc variant is selected from the group consisting of SEQ ID NO: 26, SEQ ID NO: 27, SEQ ID NO: 28 and SEQ ID NO: 29; and the sequence of the second Fc variant is selected from the group consisting of SEQ ID NO: 26, SEQ ID NO: 27, SEQ ID NO: 28 and SEQ ID NO: 29. The protein (I) and the protein (II) form a heterodimer in "Knob/Hole" mode via the Fc variants set forth in SEQ ID NO: 26 and SEQ ID NO: 27, or in SEQ ID NO: 28 and SEQ ID NO: 29. For example, when the sequence of the first Fc variant is SEQ ID NO: 26, the sequence of the second Fc variant is SEQ ID NO: 27; or when the sequence of the second Fc variant is SEQ ID NO: 26, the sequence of the first Fc variant is SEQ ID NO: 27.

In one embodiment of the present invention, provided is an IL-15 heterodimeric protein, wherein the sequence of the protein (I) is selected from the group consisting of SEQ ID NOs: 14-17, preferably SEQ ID NO: 14.

In one embodiment of the present invention, provided is an IL-15 heterodimeric protein, wherein the sequence of the protein (II) is selected from the group consisting of SEQ ID NOs: 18-25 and 34-37, preferably SEQ ID NOs: 23 and 34-37, more preferably SEQ ID NOs: 34-37.

In one embodiment of the present invention, provided is an IL-15 heterodimeric protein, wherein the sequence of the protein (I) is selected from the group consisting of SEQ ID NOs: 30-31; the sequence of the protein (II) is selected from the group consisting of SEQ ID NOs: 32-33.

The IL-15 heterodimeric protein of the present invention is selected from the following dimeric protein Nos. 3-17, wherein the dimeric proteins 3-17 are recombinantly produced by the corresponding protein (I) and protein (II) as shown below:

The present invention also relates to a nucleic acid encoding the IL-15 heterodimeric protein mentioned above.

The present invention also relates to a DNA vector comprising the nucleic acid mentioned above.

The present invention also relates to a host cell transformed with the DNA vector mentioned in the present invention.

The present invention also relates to a method for preparing the IL-15 heterodimeric protein as described above. The method comprises: culturing the host cell of the present invention under a condition sufficient for expression of the IL-15 heterodimeric protein as described above; expressing and purifying the IL-15 heterodimeric protein.

The present invention also relates to a pharmaceutical composition comprising the IL-15 heterodimeric protein of the present invention, and a pharmaceutically acceptable excipient, diluent or carrier The present invention also relates to a targeting protein molecule comprising the IL-15 heterodimeric protein structure according to the present invention.

The present invention also relates to a method for stimulating or inhibiting an immune response in a mammal, comprising: administering to the mammal a therapeutically effective amount of the IL-15 heterodimeric protein according to the present invention, or the pharmaceutical composition according to the present invention, or the targeting protein molecule according to the present invention.

The present invention also relates to use of the IL-15 heterodimeric protein according to the present invention, or the pharmaceutical composition according to the present invention, or the targeting protein molecule according to the present invention, in the preparation of a medicament for treatment of an IL-15-mediated disease or a symptom thereof, wherein the disease is selected from the group consisting of infectious disease, cancer, blood disease and autoimmune disease. The cancer is selected from the group consisting of melanoma, colorectal cancer, skin cancer, lymphoma, renal cell carcinoma, solid tumor, liver cancer, lung cancer, stomach cancer, and breast cancer; the infectious disease is selected from the group consisting of variola virus infection, HIV infection, bacterial infection, fungal infection, and HBV infection; the blood disease is selected from the group consisting of anemia, acute myeloid leukemia, myelodysplastic syndrome, and T-cell large granular lymphocytic leukemia; the autoimmune disease is selected from the group consisting of multiple sclerosis disease, psoriasis, rheumatoid arthritis, inflammatory diseases, gastritis and mucosal inflammation. The drugs are the IL-15 heterodimeric protein according to the present invention, or

| No | Protein (I) | Protein (II) |
|---|---|---|
| 3 | IL-15-Fc-Knob (SEQ ID No: 14) | Fc-Hole (SEQ ID No: 27) |
| 4 | IL-15-Fc-Hole (SEQ ID No: 15) | Fc-Knob (SEQ ID No: 26) |
| 5 | Fc-Knob-IL-15 (SEQ ID No: 16) | Fc-Hole (SEQ ID No: 27) |
| 6 | Fc-Hole-IL-15 (SEQ ID No: 17) | Fc-Knob (SEQ ID No: 26) |
| 7 | IL-15-Fc-Knob (SEQ ID No: 14) | IL-15Rα ECD-Fc-Hole (SEQ ID No: 19) |
| 8 | IL-15-Fc-Hole (SEQ ID No: 15) | IL-15Rα ECD-Fc-Knob (SEQ ID No: 18) |
| 9 | Fc-Knob-IL-15 (SEQ ID No: 16) | Fc-Hole-IL-15Rα ECD (SEQ ID No: 21) |
| 10 | Fc-Hole-IL-15 (SEQ ID No: 17) | Fc-Knob-IL-15Rα ECD (SEQ ID No: 20) |
| 11 | IL-15-Fc-Knob (SEQ ID No: 14) | IL-15Rα-sushi(77)-Fc-Hole (SEQ ID No: 23) |
| 12 | Fc-Knob(M)-IL-15 (SEQ ID No: 30) | Fc-Hole(M)-IL-15Rα-sushi(65) (SEQ ID No: 32) |
| 13 | IL-15-Fc-Knob(M) (SEQ ID No: 31) | IL-15Rα-sushi (65)-Fc-Hole(M) (SEQ ID No: 33) |
| 14 | IL-15-Fc-Knob (SEQ ID No: 14) | IL-15Rα-sushi(73)-Fc-Hole (SEQ ID No: 34) |
| 15 | IL-15-Fc-Knob (SEQ ID No: 14) | IL-15Rα-sushi(65)-Fc-Hole (SEQ ID No: 35) |
| 16 | IL-15-Fc-Knob (SEQ ID No: 14) | IL-15Rα-sushi(86)-Fc-Hole (SEQ ID No: 36) |
| 17 | IL-15-Fc-Knob (SEQ ID No: 14) | IL-15Rα-sushi(102)-Fc-Hole (SEQ ID No: 37) | the pharmaceutical composition according to the present invention administered in combination with small molecule inhibitor(s) or antibody(ies); the small molecule inhibitor(s) is/are preferably selected from alkylating agent(s); the antibody(ies) is/are preferably selected from monoclonal antibody(ies), more preferably anti-CD20, anti-PD1, anti-PDL1, or anti-Her2 antibody(ies). Further, the drug according to the present invention is administered in combination with a therapeutically effective dose of drugs selected from the group consisting of temozolomide, doxorubicin, paclitaxel, cisplatin, carboplatin, dacarbazine, topotecan, irinotecan, gemcitabine and bevacizumab.

The present invention also relates to use of the IL-15 heterodimeric protein according to the present invention, or the pharmaceutical composition according to the present invention, or the targeting protein molecule according to the present invention, for cell immunotherapy, especially for tumor immunotherapy of DC, CIK, DC-CIK, ECIK, NK, CAS-T, BiAb-T, TCR-T, and CAR-T.

Tumor immunotherapy is a hotspot of cancer therapy, which is considered the fourth cancer treatment modality following surgery, chemotherapy and radiotherapy. The objective of tumor immunology therapy is to initiate or mobilize the body's immune system, enhance anti-tumor immunity in the tumor microenvironment, and consequently control and kill tumor cells. It may be the most effective and safest approach for cancer treatment.

The mechanism underlying tumor immune escape is based on the inhibitory effect of the tumor per se on the immune system to maintain or promote tumor growth. Tumor immunotherapy is to ultimately enhance the patient's own immune system response to the tumor. It not only needs to activate the existing immune system response in vivo, but it also needs to maintain the duration and intensity of the immune system response, which is the key of tumor immunotherapy.

Cytokine immunotherapy is developed along with the production of highly pure or recombinant cytokines. The principle is that after injection into the body, certain cytokines can regulate and enhance one or more functions of immune cells, and play a stronger anti-tumor immunity.

The present invention also relates to a method for treating or preventing a disease, wherein cells express a disease-associated antigen of the disease, the method comprises: administering to a patient the IL-15 heterodimeric protein according to the present invention, or the pharmaceutical composition according to the invention, or the targeting protein molecule described in the invention; forming a specific binding complex between cells expressing the disease-associated antigen and immune cells expressing IL-15Rα sufficient for activating the immune cells; and killing the cells expressing the disease-associated antigen via the immune cells. The cells expressing the disease-associated antigen are preferably tumor cells or virus-infected cells. The immune cells are preferably T-cells, LAK cells or NK cells. The disease is selected from the group consisting of an infectious disease, cancer, blood disease and autoimmune disease. The cancer is selected from the group consisting of melanoma, colorectal cancer, skin cancer, lymphoma, renal cell carcinoma, and solid tumor; the infectious disease is selected from the group consisting of variola virus infection, HIV infection, bacterial infection, and fungal infection; the blood disease is selected from the group consisting of anemia, acute myeloid leukemia, myelodysplastic syndrome, and T-cell large granular lymphocytic leukemia; and the autoimmune disease is selected from the group consisting of multiple sclerosis, psoriasis, rheumatoid arthritis, inflammation disease, gastritis, and mucosal inflammation.

The present invention also relates to a method for treating or preventing a disease, the method comprising a step of administering to a patient the IL-15 heterodimeric protein of the invention, or the pharmaceutical composition according to the invention, or the targeting protein described in the present invention, and co-administering with other drugs, such as small molecule inhibitor(s) or antibody(ies); wherein the small molecule inhibitor(s) is/are selected from alkylating agent(s); and the antibody(ies) is/are selected from monoclonal antibody(ies), more preferably anti-CD20, anti-PD1, anti-PDL1, or anti-Her2 antibody(ies).

For a better understanding of the present disclosure, certain technical and scientific terms are specifically defined below. Unless specifically defined elsewhere in this document, all other technical and scientific terms used herein have the meaning commonly understood by one of ordinary skill in the field to which this disclosure belongs.

Terms

As used herein, the single-letter code and the three-letter code for amino acids are as described in *J. Biol. Chem,* 243, (1968) p 3558.

As used herein, "Heterodimeric protein" refers to a protein formed from the combination of two different monomeric proteins. In the present invention, two different monomeric proteins respectively contain an Fc fragment or Fc variant fragment, and form a heterodimeric protein via the interaction of the Fc fragments or Fc variant fragments.

In the present invention, "interaction" between the first Fc variant and the second Fc variant refers to the interaction between Fc variants. "Fc variant" refers to an Fc region having one or more amino acid substitutions, insertions or deletions in appropriate site(s), causing changes in the structure or function of the Fc region. "Interaction between Fc variants" refers to space-filling effects, electrostatic steering, hydrogen bonding, hydrophobic interactions and the like formed by mutated Fc variants. The interaction between Fc variants contributes to the formation of a stable heterodimeric protein. A preferred mutation is designed as the "Knob-into-Hole" mutant form.

In the present invention, a heterodimeric protein is composed of "monomeric protein" (i.e., protein (I), protein (II)), which can be a fusion protein or non-fusion protein.

As used herein, "fusion protein" refers to a protein product obtained by linking the coding regions of two or more genes using recombinant genetic methods, chemical methods or other suitable methods; and expressing the recombinant gene under control of an identical regulatory sequence. In some embodiments of the present invention, the protein (I) is a fusion protein obtained by expressing the recombinant gene of IL-15 or a variant thereof with an Fc variant; and protein (II) can be a fusion protein obtained by expressing the recombinant gene of IL-15Rα with an Fc variant. In the fusion proteins of the invention, the coding regions of two or more genes can be fused by sequence(s) encoding peptide linker(s) in one or several location(s). Peptide linkers can also be used to construct the fusion protein of the invention.

As used herein, "IL-15" or "IL-15 peptide" can be any IL-15 (interleukin-15) or a mutant thereof, such as human or non-human mammalian IL-15 or non-mammalian IL-15. Exemplary non-human mammals include pigs, rabbits, monkeys, chimpanzees, mice, and the like; and non-mammals include chickens and the like. Preferably, human interleukin-15 mature molecule is found in the Database UniProtKB, Accession Number P40933, amino acids 49-162. The term "IL-15 variant" refers to a variant molecule with increased or decreased affinity to its receptor, or increased or decreased activity in stimulating T cells or NK cells, due to one or more amino acid substitutions, additions or deletions.

The "IL-15Rα" according to the present invention can be any species of IL-15Rα or a functional fragment thereof, such as human IL-15Rα or non-human mammalian IL-15Rα or non-mammalian IL-15Rα. Exemplary non-human mammals include pigs, rabbits, monkeys, chimpanzees, mice and the like; non-mammals include chickens. Preferably, it is human IL-15Rα, and more preferably an extracellular domain fragment of human interleukin-15 receptor α, called IL-15Rα ECD (SEQ ID NO: 2), see the Database UniProtKB, Accession Number Q13261, amino acids 31-205. The term "IL-15Rα variant" refers to a functional mutant with one or more amino acid deletions, insertions or replacement mutations, which is capable of binding to its ligand molecule, such as IL-15, preferably, human IL-15Rα molecule, and more preferably a truncated form of human IL-15Rα extracellular domain fragment, which is a molecule having the activity of human interleukin-15 receptor α, and obtained by one or more amino acid deletions starting from the C-terminal fragment of the extracellular domain, preferably a deletion mutant form retaining 65 to 120 amino acids, more preferably a truncated deletion mutant form retaining 65 to 102 amino acids, such as IL-15Rα-sushi (77) (SEQ ID NO: 3) or IL-15Rα-sushi (65) (SEQ ID NO: 4).

The term "immunoglobulin Fc region" refers to an immunoglobulin chain constant region, especially the C-terminus or a part of the immunoglobulin heavy chain constant region, having no antigen-binding activity, which is a site for the interaction of the antibody molecule with effector molecules and cells. For example, an immunoglobulin Fc region can comprise two or more of the heavy chain CH1, CH2, CH3, and CH4 domains in combination with an immunoglobulin hinge region. The Fc region can be derived from different species, preferably human immunoglobulins. According to the amino acid sequence of the heavy chain constant region, immunoglobulins can be divided into different categories, mainly comprising five classes of immunoglobulins: IgA, IgD, IgE, IgG and IgM. Some of them can be further divided into subclasses (isotypes), e.g. IgG-1, IgG-2, IgG-3, IgG-4; and IgA-1 and IgA-2.

An "Fc region" preferably comprises at least one immunoglobulin hinge region, and CH2 and CH3 regions of IgG, and more preferably comprises a CH2 domain, a CH3 domain and an immunoglobulin hinge region of IgG1. The initial amino acid position of the hinge region can be varied.

Mutation design in Fc variants has been widely applied in the art for preparing bispecific antibodies or heterologous dimeric Fc fusion proteins. Representative examples comprise the "Knob-into-Hole" form proposed by Cater et al. (*Protein Engineering* vol. 9 no. 7 pp. 617-621, 1996); the Fc-containing heterodimeric form generated by Amgen technical personnel using electrostatic steering (US Patent Application Publication No. 20100286374 A1); the heterodimeric form via IgG/IgA strand exchange (SEEDbodies) proposed by Jonathan H. Davis et al. (*Protein Engineering, Design & Selection* pp. 1-8, 2010); bispecific molecules formed by DuoBody platform technology of Genmab Company (*Science*, 2007, 317 (5844)); heterodimeric proteins formed by Xencor company's technical staff via comprehensive analysis of structural calculations and Fc amino acid mutations, and different modes of action (mAbs 3: 6, 546-557; November/December 2011); heterodimeric protein forms obtained by Suzhou Corning Jerry company using Fc engineering methods on the basis of charge networks (Chinese Patent Application CN201110459100.7); and other genetic engineering methods to form heterologous dimeric functional proteins on the basis of Fc amino acid changes or functional alterations. The Knob/Hole structure on the Fc variant of the present invention refers to two Fc fragments respectively mutated, and then bound in the form of "Knob-into-Hole". Preferably, the "knob-into-hole" model proposed by Cater et al. is used to perform site mutations in the Fc region, so that the resulting first Fc variant and second Fc variant are able to be bound together in the form of "knob-into-hole" to form a heterodimer. It is within the scope of those skilled in the art to select a specific immunoglobulin Fc region from particular immunoglobulin classes and subclasses. Preferably, the Fc region of human IgG1, IgG2, IgG3, and IgG4 antibodies is selected, and more preferably the Fc region of human IgG1 antibody is selected. One of the first Fc variant and the second Fc variant is randomly selected for the knob mutation, and the other for hole mutation. In one embodiment, the first Fc variant is mutated to the knob mutation, such as the sequence shown in SEQ ID NO: 26; and the second Fc variant is mutated to the hole mutation, such as the sequence shown in SEQ ID NO: 27.

The term "linker peptide (Linker)" in the present invention is a peptide used to connect IL-15 or IL-15Rα with an Fc variant, in order to ensure the correct protein folding and stability. "Linker peptide" of the present invention is preferably (GGGGS) n, where n can be 0, 1, 2, 3, 4, 5 or more, and preferably n is 2 to 4. If the sequence of the linker peptide is too short, the advanced structural folding of the two proteins may be affected, and thus interfere with each other. If the sequence of the linker peptide is too long, the problem of immunogenicity is a concern, since the linker peptide sequence itself is a new antigen.

As used herein, "heterodimeric protein" is preferably a product of co-expressed genes, for example, co-expressed in prokaryotic cells such as *E. coli*, or co-expressed in eukaryotic cells, such as 293 and CHO cells.

As used herein, "coexpression" refers to the expression of multiple genes together in a cell to simultaneously generate their products. These genes can exist simultaneously, and be separately or commonly controlled and expressed. In the present invention, two genes are preferably co-expressed in a eukaryotic cell. The product obtained by co-expression of genes is conducive to forming a complex efficiently and easily. In the present invention, it is conducive to forming a heterodimeric protein.

As used herein, "Immunoglobulin" refers to a four-peptide chain structure connected together by disulfide bond(s) between two identical heavy chains and two identical light chains. Different immunoglobulin heavy chain constant regions exhibit different amino acid compositions and rank orders, hence present different kinds of antigenicity. Accordingly, immunoglobulins can be divided into five categories, also called immunoglobulin isotypes, namely IgM, IgD, IgG, IgA and IgE. According to the amino acid composition of the hinge region and the number and location of heavy chain disulfide bonds, the same type of Ig can be divided into different subcategories, for example, IgG can be divided into IgG1, IgG2, IgG3, and IgG4. The light chain can be divided into κ or λ chain according to different constant regions.

"Targeting protein molecule" refers to a class of proteins, which contains a fragment or a region capable of interacting with other proteins and introducing targeting peptides, such as antibody fragments, ScFv fragments or binding peptides of some classes of cell surface molecules and the like on the basis of immune cytokines, such as IL5, IL2, etc., or unique molecular design containing such cytokines, such as the molecular design in this application. For example, the interaction between an antibody and antigen, or the interaction between a ligand and receptor, makes molecules preferentially enriched in a particular tissue, organ or body part after entering into the body through its targeting effect to exert their biological functions. A new molecule is formed by fusing a free terminus of a molecule according to the present application with some class of polypeptide. The method used herein can reasonably be derived and designed to generate a series of molecules in the art.

"Administration" or "treatment," as it applies to an animal, human, experimental subject, cell, tissue, organ, or biological fluid, refers to contact of an exogenous pharmaceutical, therapeutic agent, diagnostic agent, or composition with the animal, human, subject, cell, tissue, organ, or biological fluid. "Administration" or "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" or "treatment" also means in vitro and ex vivo treatments, e.g., of a cell, with a reagent, diagnostic, binding compound, or with another cell. "Treatment," as it applies to a human, animal, or research subject, refers to therapeutic treatment, prophylactic or preventative measures, for research and diagnostic applications. "Treatment," as it applies to a human, animal, or research subject, or cell, tissue, or organ, encompasses contacting an IL-15 agonist or IL-15 antagonist with a human or animal, subject, a cell, tissue, physiological compartment, or physiological fluid. "Treatment of a cell" also encompasses situations where the IL-15 agonist or IL-15 antagonist contacts an IL-15 receptor, e.g., in the fluid phase or colloidal phase, but also situations where the agonist or antagonist does not contact the cell or the receptor.

"Treat" means to internally or externally administer a therapeutic agent, such as a composition containing an IL-15 heterodimeric protein of the present invention to a patient suffering from one or more diseases or conditions, wherein the therapeutic agent is known to have a therapeutic effect on these diseases or conditions. Typically, the therapeutic agent is administered in an amount effective to alleviate one or more diseases or conditions in the patient or population to be treated, either by inducing the regression of these diseases or conditions, or by inhibiting the progression of such diseases or conditions to any clinically measurable degree. The amount of a therapeutic agent that is effective to alleviate any particular disease or condition (also referred to as the "therapeutically effective amount") can vary according to several factors, such as the disease status, age, and weight of the patient, and the ability of the drug to elicit a desired response in the patient.

"Immune disease" or "immune disorder" includes e.g., a pathological inflammation, inflammatory disorder, and autoimmune disease or disorder. "Immune disease" also refers to an infection, persistent infection, and proliferative disorder, such as cancer, tumor, and angiogenesis. "Cancerous disease" includes, e.g., cancer, cancer cells, tumor, angiogenesis, and precancerous lesions, e.g., dysplasia.

As used herein, "polymerase chain reaction" or "PCR" refers to an amplification procedure or technique described in, e.g., U.S. Pat. No. 4,683,195. Generally, sequence information from the ends of the region of interest and beyond the region of interest needs to be available, so that oligonucleotide primers can be designed. These primers will be identical or similar in sequence to the strand opposite to the template to be amplified.

"Optional" or "optionally" means that the event or situation that follows can, but does not necessarily occur, and the description includes the instances in which the event or circumstance does or does not occur. For example, "optionally contains 1-3 antibody heavy chain variable regions" means the antibody heavy chain variable region can be, but does not need to be, present. If any are present, there can be 1, 2 or 3.

"Pharmaceutical composition" refers to a mixture containing one or more compounds according to the present invention or a physiologically/pharmaceutically acceptable salt or prodrug thereof with other chemical components, as well as additional components such as physiologically/pharmaceutically acceptable carriers and excipients. The pharmaceutical composition aims to promote administration to an organism, facilitating the absorption of the active ingredient, thereby exerting a biological effect.

Transformation of the host cell with the recombinant DNA can be carried out by conventional techniques well known to those skilled in the art. The obtained transformants are cultured using conventional methods to express the polypeptide encoded by the gene of the invention. Culture medium can be selected from various conventional culture mediums based on the host cells used. The host cells are grown under proper conditions.

DETAILED DESCRIPTION OF THE INVENTION

Figure 1:
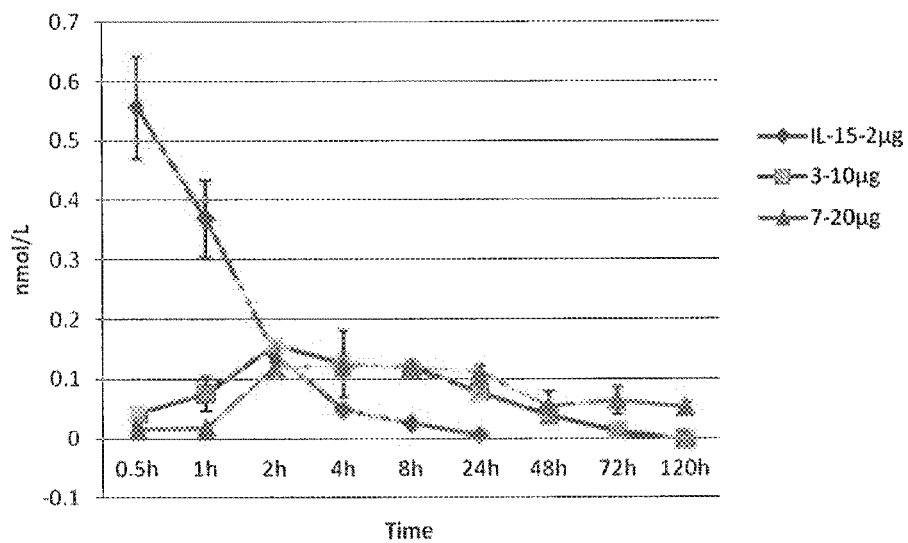
FIG. 1 shows the relationship between dosing time and molar concentration in serum samples.

Hereinafter, the present invention is further described with reference to the examples. However, the scope of the present invention is not limited thereto.

In the examples of the present invention, where specific conditions are not described, the experiments are generally conducted under conventional conditions, or under conditions proposed by the material or product manufacturers. See Sambrook et al., Molecular Cloning, A Laboratory Manual, Cold Spring Harbor Laboratory; and Current Protocols in Molecular Biology, Ausubel et al, Greene Publishing Associates, Wiley Interscience, NY. Where the source of the reagents is not specifically given, the reagents are commercially available conventional reagents.

Example 1. Obtainment of Heterodimeric IL-15 Protein

Heterodimeric protein provided herein is formed by binding protein (I) and protein (II), wherein the protein (I) is a fusion protein recombinantly produced by combining IL-15 or a variant thereof with the first Fc variant; the protein (II) can be the second Fc variant, or it can be a fusion protein recombinanly produced by combining IL-15Rα ECD or a variant thereof with the second Fc variant; and the binding is preferably binding the first Fc variant with the second Fc variant in a Knob/Hole form.

IL-15 used in the embodiments of the invention refers to the mature molecule of human interleukin-15 (SEQ ID NO: 1) or a variant thereof. IL-15Rα ECD used in the embodiments of the invention refers to the extracellular domain fragment of human interleukin-15 receptor α (SEQ ID NO: 2), and the variant thereof is preferably a truncated form, such as IL-15Rα-sushi (77) (SEQ ID NO: 3) or IL-15Rα-sushi (65) (SEQ ID NO: 4). The Fc fragment used in the embodiments of the invention can be an Fc fragment of human antibody IgG1, IgG2, IgG3, or IgG4, preferably an Fc fragment of human IgG1. In the present invention, the first Fc variant or the second Fc variant preferably underwent Knob form mutation (SEQ ID NO: 26), or Hole form mutation (SEQ ID NO: 27). In the heterodimeric protein of the present invention, the protein (I) and protein (II) form a dimer via a Knob/Hole structure between the first Fc variant and the second Fc variant, and preferably form a heterodimer via a "Knob-into-Hole" action mode between the first Fc variant and the second Fc variant. A dimer containing only a single IL-15 effector molecule can also be fused to the first Fc variant by IL-15, and a heterodimeric protein, such as heterodimeric protein 3 of the invention is formed via a Knob-into-Hole mode between the first Fc variant and the corresponding second Fc variant.

In the present invention, IL-15 or a variant thereof is fused to the first Fc fragment or the first Fc variant via a linker peptide to form a fusion protein, and in the present invention, IL-15Rα ECD or a variant thereof is fused to the second Fc fragment or the second Fc variant via a linker peptide to form a fusion protein, wherein the connection order of each protein component is not limited. The linker peptide can be a conventional flexible linker peptide known in the art, preferably (GGGGS)n, wherein n is selected from 1-10, preferably selected from 1-5, and is most preferably 2.

The corresponding protein sequences are as follows:
IL-15 (protein sequence 1): (amino acid sequence of human interleukin 15, also referred to as sequence of control IL-15)

```
                                          (SEQ ID NO: 1)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS.
```

IL-15Rα ECD (protein sequence 2): (amino acid sequence of extracellular domain of human interleukin 15 receptor alpha, also known as the indicated IL-15Rα segment in molecule H formed by fusing with Fc)

```
                                          (SEQ ID NO: 2)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

ASSPSSNNTAATTAAIVPGSQLMPSKSPSTGTTEISSHESSHGTPSQTTA

KNWELTASASHQPPGVYPQGHSDTT.
```

IL-15Rα-sushi (77) (protein sequence 3): (a domain maintaining more than 90% of the binding activity in the extracellular domain of human interleukin-15 receptor alpha, known as the sushi domain plus a short linker peptide, belongs to a truncated form of IL-15Rα)

```
                                          (SEQ ID NO: 3)
ITCPPPMSVEHADIWVKSYSLYSRERYICNSGFKRKAGTSSLTECVLNKA

TNVAHWTTPSLKCIRDPALVHQRPAPP.
```

IL-15Rα-sushi (65) (protein sequence 4): (a domain maintaining more than 90% of the binding activity in the extracellular domain of human interleukin-15 receptor alpha, known as the sushi domain, belongs to a truncated form of IL-15Rα)

```
                                          (SEQ ID NO: 4)
ITCPPPMSVEHADIWVKSYSLYSRERYICNSGFKRKAGTSSLTECVLNKA

TNVAHWTTPSLKCIR.
```

IL15Rα-sushi (73) (protein sequence 5):

```
                                          (SEQ ID NO: 5)
ITCPPPMSVEHADIWVKSYSLYSRERYICNSGFKRKAGTSSLTECVLNKA

TNVAHWTTPSLKCIRDPALVHQR.
```

IL15Rα-sushi (86) (protein sequence 6):

```
                                          (SEQ ID NO: 6)
ITCPPPMSVEHADIWVKSYSLYSRERYICNSGFKRKAGTSSLTECVLNKA

TNVAHWTTPSLKCIRDPALVHQRPAPPSTVTTAGVT.
```

IL15Rα-sushi (102) (protein sequence 7):

```
                                          (SEQ ID NO: 7)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

AS.
```

IL-15-Fc (protein sequence 8): (a fusion protein formed by linking human interleukin-15 molecule with human IgG1-Fc sequence via a linker peptide, expressed as a bivalent homodimer, wherein the IL-15 molecule is at the N-terminus of the protein)

(SEQ ID NO: 8)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSGGGGSGGGGSEPKSSDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSL

SLSPGK.

Fc-IL-15 (protein sequence 9): (a fusion protein formed by linking human interleukin-15 molecule with human IgG1-Fc sequence via a linker peptide, expressed as a bivalent homodimer, wherein the IL-15 molecule is at the C-terminus of the protein)

(SEQ ID NO: 9)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGKGGGGSGGGGSNWVNVISD

LKKIEDLIQSMHIDATLYTESDVHPSCKVTAMKCFLLELQVISLESGDAS

IHDTVENLIILANNSLSSNGNVTESGCKECEELEEKNIKEFLQSFVHIVQ

MFINTS.

IL-15Rα ECD-Fc (protein sequence 10): (a fusion protein formed by linking the extracellular domain of human interleukin 15 receptor alpha with human IgG1-Fc sequence via a linker peptide, expressed as a bivalent homodimer, wherein the IL-15Rα-ECD molecule is at the N-terminus of the protein)

(SEQ ID NO: 10)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

ASSPSSNNTAATTAAIVPGSQLMPSKSPSTGTTEISSHESSHGTPSQTTA

KNWELTASASHQPPGVYPQGHSDTTGGGGSGGGGSEPKSSDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK.

Fc-IL-15Rα ECD (protein sequence 11): (a fusion protein formed by linking the extracellular domain of human interleukin 15 receptor alpha with human IgG1-Fc sequence via a linker peptide, expressed as a bivalent homodimer, wherein the IL-15Rα-ECD molecule is at the C-terminus of the protein)

(SEQ ID NO: 11)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGKGGGGSGGGGSITCPPPMS

VEHADIWVKSYSLYSRERYICNSGFKRKAGTSSLTECVLNKATNVAHWTT

PSLKCIRDPALVHQRPAPPSTVTTAGVTPQPESLSPSGKEPAASSPSSNN

TAATTAAIVPGSQLMPSKSPSTGTTEISSHESSHGTPSQTTAKNWELTAS

ASHQPPGVYPQGHSDTT.

IL-15Rα-sushi (77)-Fc (protein sequence 12): (a fusion protein formed by linking sushi (77) fragment consisting of the sushi domain of human interleukin-15 receptor alpha extracellular domain and a linker peptide with human IgG1-Fc sequence via a linker peptide, wherein the sushi (77) fragment is at the N-terminus)

(SEQ ID NO: 12)
ITCPPPMSVEHADIWVKSYSLYSRERYICNSGFKRKAGTSSLTECVLNKA

TNVAHWTTPSLKCIRDPALVHQRPAPPSGGSGGGGSGGGSGGGGSLQEPK

SSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK.

Fc-IL-15Rα-sushi (77) (protein sequence 13): (a fusion protein formed by linking sushi+ fragment consisting of the sushi domain of human interleukin-15 receptor alpha extracellular domain and a linker peptide with human IgG1-Fc sequence via a linker peptide, wherein the sushi+ fragment is at the C-terminus)

(SEQ ID NO: 13)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGKSGGSGGGGSGGGSGGGGS

LQITCPPPMSVEHADIWVKSYSLYSRERYICNSGFKRKAGTSSLTECVLN

KATNVAHWTTPSLKCIRDPALVHQRPAPP.

IL-15-Fc-Knob (protein sequence 14): (Fc portion of the above sequence 8 is mutated in a Knob form, and paired with another fusion molecule in a Hole form)

(SEQ ID NO: 14)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSGGGGSGGGGSEPKSSDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSREEMTKNQVSLYCLVKGFYPSDIAVEWESNGQPENNY

KTTPPVLDSDGSFFLYSKLTVDKSRWQQGNVFSCSVMHEALHNHYTQKSL

SLSPGK.

IL-15-Fc-Hole (protein sequence 15): (Fc portion of the above sequence 8 is mutated in a Hole form, and paired with another fusion molecule in a Knob form)

(SEQ ID NO: 15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSGGGGSGGGGSEPKSSDKTHTCPPCPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPSREEMTKNQVSLTCLVKGFYPSDIAVEWESNGQPENNY

KTTPPVLDSDGSFFLTSKLTVDKSRWQQGNVFSCSVMHEALHNHYTQKSL

SLSPGK.

Fc-Knob-IL-15 (protein sequence 16): (Fc portion of the above sequence 9 is mutated in a Knob form, and paired with another fusion molecule in a Hole form)

(SEQ ID NO: 16)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

YCLVKGFYPSDIAVEWESNGQPENNYKTTPPVLDSDGSFFLYSKLTVDKS

RWQQGNVFSCSVMHEALHNHYTQKSLSLSPGKGGGGSGGGGSNWVNVISD

LKKIEDLIQSMHIDATLYTESDVHPSCKVTAMKCFLLELQVISLESGDAS

IHDTVENLIILANNSLSSNGNVTESGCKECEELEEKNIKEFLQSFVHIVQ

MFINTS.

Fc-Hole-IL-15 (protein sequence 17): (Fc portion of the above sequence 9 is mutated in a Hole form, and paired with another fusion molecule in a Knob form)

(SEQ ID NO: 17)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLTSKLTVDKS

RWQQGNVFSCSVMHEALHNHYTQKSLSLSPGKGGGGSGGGGSNWVNVISD

LKKIEDLIQSMHIDATLYTESDVHPSCKVTAMKCFLLELQVISLESGDAS

IHDTVENLIILANNSLSSNGNVTESGCKECEELEEKNIKEFLQSFVHIVQ

MFINTS.

IL-15Rα ECD-Fc-Knob (protein sequence 18): (Fc portion of the above sequence 10 is mutated in a Knob form, and paired with another fusion molecule in a Hole form)

(SEQ ID NO: 18)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

ASSPSSNNTAATTAAIVPGSQLMPSKSPSTGTTEISSHESSHGTPSQTTA

KNWELTASASHQPPGVYPQGHSDTTGGGGSGGGGSEPKSSDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLYCLVKGFYPSDIAVE

WESNGQPENNYKTTPPVLDSDGSFFLYSKLTVDKSRWQQGNVFSCSVMHE

ALHNHYTQKSLSLSPGK.

IL-15Rα ECD-Fc-Hole (protein sequence 19): (Fc portion of the above sequence 10 is mutated in a Hole form, and paired with another fusion molecule in a Knob form)

(SEQ ID NO: 19)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

ASSPSSNNTAATTAAIVPGSQLMPSKSPSTGTTEISSHESSHGTPSQTTA

KNWELTASASHQPPGVYPQGHSDTTGGGGSGGGGSEPKSSDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLTSKLTVDKSRWQQGNVFSCSVMHE

ALHNHYTQKSLSLSPGK.

Fc-Knob-IL-15Rα ECD (protein sequence 20): (Fc portion of the above sequence 11 is mutated in a Knob form, and paired with another fusion molecule in a Hole form)

(SEQ ID NO: 20)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

YCLVKGFYPSDIAVEWESNGQPENNYKTTPPVLDSDGSFFLYSKLTVDKS

RWQQGNVFSCSVMHEALHNHYTQKSLSLSPGKGGGGSGGGGSITCPPPMS

VEHADIWVKSYSLYSRERYICNSGFKRKAGTSSLTECVLNKATNVAHWTT

PSLKCIRDPALVHQRPAPPSTVTTAGVTPQPESLSPSGKEPAASSPSSNN

TAATTAAIVPGSQLMPSKSPSTGTTEISSHESSHGTPSQTTAKNWELTAS

ASHQPPGVYPQGHSDTT.

Fc-Hole-IL-15Rα ECD (protein sequence 21): (Fc portion of the above sequence 11 is mutated in a Hole form, and paired with another fusion molecule in a Knob form)

(SEQ ID NO: 21)
EPKSSDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

```
TCLVKGFYPSDIAVEWESNGQPENNYKTTPPVLDSDGSFFLTSKLTVDKS
RWQQGNVFSCSVMHEALHNHYTQKSLSLSPGKGGGGSGGGGSITCPPPMS
VEHADIWVKSYSLYSRERYICNSGFKRKAGTSSLTECVLNKATNVAHWTT
PSLKCIRDPALVHQRPAPPSTVTTAGVTPQPESLSPSGKEPAASSPSSNN
TAATTAAIVPGSQLMPSKSPSTGTTEISSHESSHGTPSQTTAKNWELTAS
ASHQPPGVYPQGHSDTT.
```

IL-15Rα-sushi (77)-Fc-Knob (protein sequence 22): (Fc portion of the above sequence 12 is mutated in a Knob form, and paired with another fusion molecule in a Hole form)

```
                                          (SEQ ID NO: 22)
ITCPPPMSVEHADIWVKSYSLYSRERYICNSGFKRKAGTSSLTECVLNKA
TNVAHWTTPSLKCIRDPALVHQRPAPPSGGSGGGGSGGGSGGGGSLQEPK
SSDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLYCL
VKGFYPSDIAVEWESNGQPENNYKTTPPVLDSDGSFFLYSKLTVDKSRWQ
QGNVFSCSVMHEALHNHYTQKSLSLSPGK.
```

IL-15Rα-sushi (77)-Fc-Hole (protein sequence 23): (Fc portion of the above sequence 12 is mutated in a Hole form, and paired with another fusion molecule in a Knob form)

```
                                          (SEQ ID NO: 23)
ITCPPPMSVEHADIWVKSYSLYSRERYICNSGFKRKAGTSSLTECVLNKA
TNVAHWTTPSLKCIRDPALVHQRPAPPSGGSGGGGSGGGSGGGGSLQEPK
SSDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCL
VKGFYPSDIAVEWESNGQPENNYKTTPPVLDSDGSFFLTSKLTVDKSRWQ
QGNVFSCSVMHEALHNHYTQKSLSLSPGK.
```

Fc-Knob-IL-15Rα-sushi (77) (protein sequence 24): (Fc portion of the above sequence 13 is mutated in a Knob form, and paired with another fusion molecule in a Hole form)

```
                                          (SEQ ID NO: 24)
EPKSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
YCLVKGFYPSDIAVEWESNGQPENNYKTTPPVLDSDGSFFLYSKLTVDKS
RWQQGNVFSCSVMHEALHNHYTQKSLSLSPGKSGGSGGGGSGGGSGGGGS
LQITCPPPMSVEHADIWVKSYSLYSRERYICNSGFKRKAGTSSLTECVLN
KATNVAHWTTPSLKCIRDPALVHQRPAPP.
```

Fc-Hole-IL-15Rα-sushi (77) (protein sequence 25): (Fc portion of the above sequence 13 is mutated in a Hole form, and paired with another fusion molecule in a Knob form)

```
                                          (SEQ ID NO: 25)
EPKSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
TCLVKGFYPSDIAVEWESNGQPENNYKTTPPVLDSDGSFFLTSKLTVDKS
RWQQGNVFSCSVMHEALHNHYTQKSLSLSPGKSGGSGGGGSGGGSGGGGS
LQITCPPPMSVEHADIWVKSYSLYSRERYICNSGFKRKAGTSSLTECVLN
KATNVAHWTTPSLKCIRDPALVHQRPAPP.
```

Fc-Knob (protein sequence 26): (Knob mutant form of human IgG1-Fc segment, which can be paired with IL-15-Fc-Hole/Fc-IL-15-Hole)

```
                                          (SEQ ID NO: 26)
EPKSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
YCLVKGFYPSDIAVEWESNGQPENNYKTTPPVLDSDGSFFLYSKLTVDKS
RWQQGNVFSCSVMHEALHNHYTQKSLSLSPGK.
```

Fc-Hole (protein sequence 27): (Hole mutant form of human IgG1-Fc segment, which can be paired with IL-15-Fc-Knob/Fc-IL-15-Knob)

```
                                          (SEQ ID NO: 27)
EPKSSDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSL
TCLVKGFYPSDIAVEWESNGQPENNYKTTPPVLDSDGSFFLTSKLTVDKS
RWQQGNVFSCSVMHEALHNHYTQKSLSLSPGK.
```

Fc-Knob (M) (protein sequence 28): Another form of Fc mutation, which can be paired with Fc-Hole (M) to form a heterodimer.

```
                                          (SEQ ID NO: 28)
EPKSSDKTHTSPPSPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVYTLPPCRDELTKNQVSL
WCLVKGFYPSDIAVEWESNGQPENNYKTTPPVLDSDGSFFLYSKLTVDKS
RWQQGNVFSCSVMHEALHNHYTQKSLSLSPGK.
```

Fc-Hole (M) (protein sequence 29): Another form of Fc mutation, which can be paired with Fc-Knob (M) to form a heterodimer.

```
                                          (SEQ ID NO: 29)
EPKSSDKTHTSPPSPAPELLGGPSVFLFPPKPKDTLMISRTPEVTCVVVD
VSHEDPEVKFNWYVDGVEVHNAKTKPREEQYNSTYRVVSVLTVLHQDWLN
GKEYKCKVSNKALPAPIEKTISKAKGQPREPQVCTLPPSRDELTKNQVSL
```

-continued

SCAVKGFYPSDIAVEWESNGQPENNYKTTPPVLDSDGSFFLVSKLTVDKS

RWQQGNVFSCSVMHEALHNHYTQKSLSLSPGK.

Fc-Knob (M)-IL-15 (protein sequence 30) (different mutation sites relative to Knob, another mutation manner of heterodimer)

(SEQ ID NO: 30)
EPKSSDKTHTSPPSPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPCRDELTKNQVSL

WCLVKGFYPSDIAVEWESNGQPENNYKTTPPVLDSDGSFFLYSKLTVDKS

RWQQGNVFSCSVMHEALHNHYTQKSLSLSPGKGGGGSGGGGSGGGGSGGG

GSNWVNVISDLKKIEDLIQSMHIDATLYTESDVHPSCKVTAMKCFLLELQ

VISLESGDASIHDTVENLIILANNSLSSNGNVTESGCKECEELEEKNIKE

FLQSFVHIVQMFINTS.

IL-15-Fc-Knob (M) (protein sequence 31) (different mutation site relative to Knob, another mutation manner of heterodimer)

(SEQ ID NO: 31)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSGGGGSGGGGSEPKSSDKTHTSPPSPAPELLGGPSVF

LFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKG

QPREPQVYTLPPCRDELTKNQVSLWCLVKGFYPSDIAVEWESNGQPENNY

KTTPPVLDSDGSFFLYSKLTVDKSRWQQGNVFSCSVMHEALHNHYTQKSL

SLSPGK.

Fc-Hole (M)-IL-15Rα-sushi (65) (protein sequence 32) (different mutation site relative to Hole, another mutation manner of heterodimer)

(SEQ ID NO: 32)
EPKSSDKTHTSPPSPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVCTLPPSRDELTKNQVSL

SCAVKGFYPSDIAVEWESNGQPENNYKTTPPVLDSDGSFFLVSKLTVDKS

RWQQGNVFSCSVMHEALHNHYTQKSLSLSPGKGGGGSGGGGSGGGGSGGG

GSITCPPPMSVEHADIWVKSYSLYSRERYICNSGFKRKAGTSSLTECVLN

KATNVAHWTTPSLKCIR.

IL-15Rα-sushi (65)-Fc-Hole (M) (protein sequence 33) (different mutation site relative to Hole, another mutation manner of heterodimer)

(SEQ ID NO: 33)
ITCPPPMSVEHADIWVKSYSLYSRERYICNSGFKRKAGTSSLTECVLNKA

TNVAHWTTPSLKCIRGGGGSGGGGSGGGGSGGGGSEPKSSDKTHTSPPSP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVCTLPPSRDELTKNQVSLSCAVKGFYPSDIAVE

WESNGQPENNYKTTPPVLDSDGSFFLVSKLTVDKSRWQQGNVFSCSVMHE

ALHNHYTQKSLSLSPGK.

IL-15Rα-sushi (73)-Fc-Hole (protein sequence 34): (sushi (73) refers to a truncated form of IL15Rα containing the sushi domain with 73 amino acids in length)

(SEQ ID NO: 34)
ITCPPPMSVEHADIWVKSYSLYSRERYICNSGFKRKAGTSSLTECVLNKA

TNVAHWTTPSLKCIRDPALVHQRSGGSGGGGSGGGSGGGGSLQEPKSSDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGF

YPSDIAVEWESNGQPENNYKTTPPVLDSDGSFFLTSKLTVDKSRWQQGNV

FSCSVMHEALHNHYTQKSLSLSPGK

IL-15Rα-sushi (65)-Fc-Hole (protein sequence 35): (sushi (65) refers to a sushi domain with 65 amino acids in length)

(SEQ ID NO: 35)
ITCPPPMSVEHADIWVKSYSLYSRERYICNSGFKRKAGTSSLTECVLNKA

TNVAHWTTPSLKCIRSGGSGGGGSGGGSGGGGSLQEPKSSDKTHTCPPCP

APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLTSKLTVDKSRWQQGNVFSCSVMHE

ALHNHYTQKSLSLSPGK.

IL-15Rα-sushi (86)-Fc-Hole (protein sequence 36): (sushi (86) refers to a truncated form of IL15Rα containing the sushi domain with 86 amino acids in length)

(SEQ ID NO: 36)
ITCPPPMSVEHADIWVKSYSLYSRERYICNSGFKRKAGTSSLTECVLNKA

TNVAHWTTPSLKCIRDPALVHQRPAPPSTVTTAGVTSGGSGGGGSGGGSG

GGGSLQEPKSSDKTHTCPPCPAPELLGGPSVFLFPPKPKDTLMISRTPEV

TCVVVDVSHEDPEVKFNWYVDGVEVHNAKTKPREEQYNSTYRVVSVLTVL

HQDWLNGKEYKCKVSNKALPAPIEKTISKAKGQPREPQVYTLPPSREEMT

KNQVSLTCLVKGFYPSDIAVEWESNGQPENNYKTTPPVLDSDGSFFLTSK

LTVDKSRWQQGNVFSCSVMHEALHNHYTQKSLSLSPGK.

IL-15Rα-sushi (102)-Fc-Hole (protein sequence 37): (sushi (102) refers to a truncated form of IL15Rα containing the sushi domain with 102 amino acids in length)

(SEQ ID NO: 37)
ITCPPPMSVEHADIWVKSYSLYSRERYICNSGFKRKAGTSSLTECVLNKA

TNVAHWTTPSLKCIRDPALVHQRPAPPSTVTTAGVTPQPESLSPSGKEPA

ASSGGSGGGGSGGGSGGGGSLQEPKSSDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKT

TPPVLDSDGSFFLTSKLTVDKSRWQQGNVFSCSVMHEALHNHYTQKSLSL

SPGK.

Example 2. Construction of Related Vectors

Materials:
Eukaryotic expression vector pcDNA3.1 (+) (Life technologies, Cat. No. V790-20);
IL-15 (DNA sequence 1), IL-15Rα ECD (DNA sequence 2) and IgG1Fc (DNA sequence 3) DNA fragments were synthesized by a gene synthesis company (GENEWIZ, Inc., Suzhou);
Primers DNA fragments were synthesized by a gene synthesis company (GENEWIZ, Inc., Suzhou).
Procedure:
Fragments were spliced by the conventional PCR method.
1. Fragment Ligation
IL-15-Fc fragment: By using overlapping PCR, an IL-15-Fc fragment (DNA sequence 4, SEQ ID NO: 42) was formed by joining three DNA fragments in the order of IL-15, linker peptide, and Fc.
IL-15Rα ECD-Fc fragment: By using overlapping PCR, an IL-15Rα ECD-Fc fragment (DNA sequence 5, SEQ ID NO: 43) was formed by joining three DNA fragments in the order of IL-15Rα ECD, linker peptide, and Fc.
Fc-IL-15 fragment: By using overlapping PCR, a Fc-IL-15 fragment (DNA Sequence 6, SEQ ID NO: 44) was formed by joining three DNA fragments in the order of Fc, linker peptide, and IL-15.
Fc-IL-15Rα ECD fragment: By using overlapping PCR, a Fc-IL-15Rα ECD fragment (DNA Sequence 7, SEQ ID NO: 45) was formed by joining three DNA fragments in the order of Fc, linker peptide, and IL-15Rα ECD.
IL-15-Fc-Knob fragment: By using overlapping PCR, an IL-15-Fc-Knob fragment (DNA Sequence 8, SEQ ID NO: 46) was formed by joining three DNA fragments in the order of IL-15, linker peptide, and Fc-Knob.
IL-15-Fc-Hole fragment: By using overlapping PCR, an IL-15-Fc-Hole fragment (DNA Sequence 9, SEQ ID NO: 47) was formed by joining three DNA fragments in the order of IL-15, linker peptide, and Fc-Hole.
Fc-Knob-IL-15 fragment: By using overlapping PCR, a Fc-Knob-IL-15 fragment (DNA sequence 10, SEQ ID NO: 48) was formed by joining three DNA fragments in the order of Fc-Knob, linker peptide, and IL-15.
Fc-Hole-IL-15 fragment: By using overlapping PCR, a Fc-Hole-IL-15 fragment (DNA Sequence 11, SEQ ID NO: 49) was formed by joining three DNA fragments in the order of Fc-Hole, linker peptide, and IL-15.
IL-15Rα ECD-Fc-Knob fragment: By using overlapping PCR, an IL-15RαECD-Fc-Knob fragment (DNA Sequence 12, SEQ ID NO: 50) was formed by joining three DNA fragments in the order of IL-15Rα ECD, linker peptide, and Fc-Knob.

IL-15Rα ECD-Fc-Hole fragment: By using overlapping PCR, an IL-15RαECD-Fc-Hole fragment (DNA Sequence 13, SEQ ID NO: 51) was formed by joining three DNA fragments in the order of IL-15Rα ECD, linker peptide, and Fc-Hole.
Fc-Knob-IL-15Rα ECD fragment: By using overlapping PCR, a Fc-Knob-IL-15RαECD fragment (DNA Sequence 14, SEQ ID NO: 52) was formed by joining three DNA fragments in the order of Fc-Knob, linker peptide, and IL-15Rα ECD.
Fc-Hole-IL-15Rα ECD fragment: By using overlapping PCR, a Fc-Hole-IL-15RαECD fragment (DNA Sequence 15, SEQ ID NO: 53) was formed by joining three DNA fragments in the order of Fc-Hole, linker peptide, and IL-15Rα ECD.
Fc-Knob fragment, DNA sequence 16, SEQ ID NO: 54.
Fc-Hole fragment, DNA sequence 17, SEQ ID NO: 55.
Fc-Knob (M)-IL-15, DNA sequence 18, nucleotide sequence encoding the precursor of protein sequence 30, SEQ ID NO: 56.
IL-15-Fc-Knob (M), DNA sequence 19, nucleotide sequence encoding the precursor of protein sequence 31, SEQ ID NO: 57.
Fc-Hole (M)-IL-15Rα-sushi (65), DNA sequence 20, nucleotide sequence encoding the precursor of protein sequence 32, SEQ ID NO: 58.
IL15Rα-sushi (65)-Fc-Hole (M), DNA sequence 21, nucleotide sequence encoding the precursor of protein sequence 33, SEQ ID NO: 59.
IL-15Rα-sushi (73)-Fc-Hole, DNA sequence 22, nucleotide sequence encoding the precursor of protein sequence 34, SEQ ID NO: 60.
IL-15Rα-sushi (65)-Fc-Hole, DNA sequence 23, nucleotide sequence encoding the precursor of protein sequence 35, SEQ ID NO: 61.
IL-15Rα-sushi (86)-Fc-Hole, DNA sequence 24, nucleotide sequence encoding the precursor of protein sequence 36, SEQ ID NO: 62.
IL-15Rα-sushi (102)-Fc-Hole, DNA sequence 25, nucleotide sequence encoding the precursor of protein sequence 37, SEQ ID NO: 63.
2. Inserting Restriction Sites and Signal Peptide Sequence:
Restriction endonuclease KpnI site, Kozak sequence, and the signal peptide sequence were inserted at the 5'-terminus of the gene fragment by PCR method. The sequence between the KpnI site and the gene fragment is shown in SEQ ID NO: 38:

ggtaccttgtgcccgggcgccaccatggagtttgggctgagctggctttt tcttgtcgcgattcttaagggtgtccagtgc The underline represents a KpnI restriction site, the italic represents the signal peptide sequence. The termination codon TGA and a NotI restriction enzyme site were inserted into the 3'-terminus of the three fragments, respectively.
3. Construction of Expression Vectors
The aforementioned gene fragments were inserted into the vector pcDNA3.1 (+) respectively using restriction enzyme KpnI and NotI sites to construct expression vectors, such as pcDNA3.1-IL-15-Fc, pcDNA3.1-IL-15Rα ECD-Fc, pcDNA3.1-Fc, pcDNA3.1-Fc-IL-15, pcDNA3.1-Fc-IL-15Rα ECD and the like, to obtain the corresponding expression plasmids.

4. Site-Directed Mutagenesis in Gene

Site-directed mutagenesis was carried out using a KOD kit (TOYOBO Cat.KOD-201) 25 μL system: 2.5 μL 10×KOD buffer, 2.5 μL 2 mM dNTPs, 1 μL primer 1 (10 μM), 1 μL primer 2 (10 μM), 0.5 μL KOD plus, 1 μL 25 mM MgSO4, and 16 μL ddH2O. Synthesis procedure: 94° C. for 2 min, 94° C. for 30 sec, 55° C. for 30 sec, 68° C. for 11 minutes, and after 25 amplification cycles, the PCR amplification process was terminated by another 11 minutes at 68° C. The PCR product was digested for 5 hours with direct addition of 14 of DpnI (NEB Cat. R0176L), transformed into DH5α competent cells, and clones were picked for sequencing to obtain the desired plasmids. Protein 3 involved in the example of the present invention was obtained by expressing the expression vector containing DNA sequence 8 (SEQ ID NO: 46) and DNA sequence 17 (SEQ ID NO: 55); and Protein 7 was obtained by expressing the expression vector containing DNA sequence 8 (SEQ ID NO: 46) and DNA sequence 13 (SEQ ID NO: 51). Proteins in other examples were coexpressed by the expression vector containing the DNA sequences.

Constructing Nucleotide Sequence for Expression Plasmid

The following DNA sequences were used for vector construction, wherein a single underline represents the DNA sequence of the signal peptide, a dotted underline represents the DNA sequence for the peptide linker, and the double underline represents the DNA sequence for Fc undergoing Knob/Hole mutation(s).

DNA Sequence 1: (IL-15, nucleotide sequence of human interleukin-15)

(SEQ ID NO: 39)
ATGGACATGCGGGTGCCAGCCCAGCTGCTGGGCCTGTTGCTGCTGTGGTT

CCCCGGCTCTCGGTGCAACTGGGTGAATGTAATTAGTGATTTGAAAAAAA

TTGAAGATCTTATTCAATCTATGCATATTGATGCTACTTTATATACGGAA

AGTGATGTTCACCCGAGTTGCAAAGTAACAGCAATGAAGTGCTTTCTCTT

GGAGTTACAAGTTATTTCACTTGAGTCCGGCGATGCAAGTATTCATGATA

CAGTAGAAAATCTGATCATCTTAGCAAACAACAGTTTGTCTTCTAATGGG

AATGTAACAGAATCTGGATGCAAAGAATGTGAGGAACTGGAGGAAAAAAA

TATTAAAGAATTTTTGCAGAGTTTTGTACATATTGTCCAAATGTTCATCA

ACACTTCT.

DNA Sequence 2: (IL-15Rα ECD, nucleotide sequence of the extracellular domain of human interleukin-15 receptor alpha)

(SEQ ID NO: 40)
ATGGACATGCGGGTGCCAGCCCAGCTGCTGGGCCTGTTGCTGCTGTGGTT

CCCCGGCTCTCGGTGCATCACCTGCCCTCCACCTATGTCCGTGGAACACG

CAGACATCTGGGTCAAGAGCTACAGCTTGTACTCCCGCGAGCGCTACATT

TGTAACTCTGGTTTCAAGCGTAAAGCCGGCACCTCCAGCCTGACCGAGTG

CGTGTTGAACAAGGCCACCAATGTCGCCCACTGGACAACCCCAAGTCTCA

AATGCATTCGCGACCCTGCCCTGGTTCACCAACGCCCAGCGCCACCATCC

ACAGTAACCACTGCAGGCGTGACCCCACAGCCAGAGAGCCTCTCCCCTTC

TGGCAAAGAGCCAGCAGCTTCATCTCCAAGCTCAAACAACACAGCGGCCA

CAACAGCAGCTATTGTCCCGGGCTCCCAGCTGATGCCTTCAAAATCACCT

TCCACAGGCACCACAGAGATCAGCAGTCATGAGTCCTCCCACGGCACCCC

ATCTCAGACAACAGCCAAGAACTGGGAACTCACAGCATCCGCCTCCCACC

AGCCGCCAGGTGTGTATCCACAGGGCCACAGCGACACCACT.

DNA Sequence 3: (Fc, nucleotide sequence of human IgG Fc)

(SEQ ID NO: 41)
ATGGACATGCGGGTGCCAGCCCAGCTGCTGGGCCTGTTGCTGCTGTGGTT

CCCCGGCTCTCGGTGCGAACCTAAGTCCTCTGATAAGACCCACACATGTC

CCCCCTGCCCAGCTCCTGAGCTCTTGGGCGGACCTTCCGTGTTTCTGTTC

CCCCCAAAGCCCAAGGATACCCTTATGATCAGCAGAACACCCGAAGTTAC

TTGCGTGGTCGTGGACGTTTCTCACGAAGATCCTGAAGTGAAATTCAACT

GGTACGTGGATGGCGTGGAGGTGCACAATGCTAAGACTAAGCCCCGTGAA

GAGCAGTACAACTCTACCTACCGGGTCGTTTCAGTGCTGACTGTTCTCCA

TCAGGACTGGCTCAACGGGAAGGAGTATAAGTGCAAGGTGTCTAACAAGG

CACTGCCCGCACCCATCGAGAAGACCATTTCTAAGGCCAAGGGTCAACCA

CGGGAGCCACAGGTTTACACATTGCCTCCCAGTCGGGAGGAGATGACAAA

GAATCAAGTGTCACTTACATGTCTTGTGAAGGGCTTCTACCCCTCAGACA

TCGCCGTGGAGTGGGAGAGCAACGGACAACCAGAAAACAACTACAAGACC

ACACCTCCTGTGCTCGATTCAGATGGTTCCTTTTTCTTGTACAGCAAACT

CACCGTTGACAAGAGTCGGTGGCAGCAAGGAAATGTGTTCAGCTGTTCTG

TGATGCACGAGGCCCTGCACAACCATTATACCCAAAAATCTCTCAGCCTT

TCTCCCGGCAAG.

DNA Sequence 4: (IL-15-Fc, nucleotide sequence encoding the precursor of protein sequence 5)

(SEQ ID NO: 42)
ATGGACATGCGGGTGCCAGCCCAGCTGCTGGGCCTGTTGCTGCTGTGGTT

CCCCGGCTCTCGGTGCaactgggtgaatgtaattagtgatttgaaaaaaa ttgaagatcttattcaatctatgcatattgatgctactttatatacggaa agtgatgttcacccgagttgcaaagtaacagcaatgaagtgctttctctt ggagttacaagttatttcacttgagtccggcgatgcaagtattcatgata cagtagaaaatctgatcatcttagcaaacaacagtttgtcttctaatggg aatgtaacagaatctggatgcaaagaatgtgaggaactggaggaaaaaaa tattaaagaattttttgcagagttttgtacatattgtccaaatgttcatca acacttctGGCGGAGGAGGCTCTGGGGGCGGAGGAAGCGAACCTAAGTCC

TCTGATAAGACCCACACATGTCCCCCCTGCCCAGCTCCTGAGCTCTTGGG

CGGACCTTCCGTGTTTCTGTTCCCCCCAAAGCCCAAGGATACCCTTATGA

TCAGCAGAACACCCGAAGTTACTTGCGTGGTCGTGGACGTTTCTCACGAA

GATCCTGAAGTGAAATTCAACTGGTACGTGGATGGCGTGGAGGTGCACAA

TGCTAAGACTAAGCCCCGTGAAGAGCAGTACAACTCTACCTACCGGGTCG

TTTCAGTGCTGACTGTTCTCCATCAGGACTGGCTCAACGGGAAGGAGTAT

AAGTGCAAGGTGTCTAACAAGGCACTGCCCGCACCCATCGAGAAGACCAT

TTCTAAGGCCAAGGGTCAACCACGGGAGCCACAGGTTTACACATTGCCTC

CCAGTCGGGAGGAGATGACAAAGAATCAAGTGTCACTTACATGTCTTGTG

AAGGGCTTCTACCCCTCAGACATCGCCGTGGAGTGGGAGAGCAACGGACA

ACCAGAAAACAACTACAAGACCACACCTCCTGTGCTCGATTCAGATGGTT

CCTTTTTCTTGTACAGCAAACTCACCGTTGACAAGAGTCGGTGGCAGCAA

GGAAATGTGTTCAGCTGTTCTGTGATGCACGAGGCCCTGCACAACCATTA

TACCCAAAAATCTCTCAGCCTTTCTCCCGGCAAG.

DNA Sequence 5: (IL-15Rα ECD-Fc, nucleotide sequence encoding the precursor of protein sequence 7)

(SEQ ID NO: 43)

<u>ATGGACATGCGGGTGCCAGCCCAGCTGCTGGGCCTGTTGCTGCTGTGGTTCCCCGGC</u>

<u>TCTCGGTGC</u>atcACCtgccctCCACCTatgtccgtggaacacgcagacatctgggtcaagagctacagcttgtactccCG CgagcgCtacatttgtaactctggtttcaagcgtaaagccggcACCtccagcctgACCgagtgcgtgttgaacAAGGCCAC CaatgtcgccactggacaaccccAagtctcaaatgcattCGCgaccctgccctggttcaccaaCGCccagcgccaccAtccaca gtaACCACTgcaggCgtgaccccacagccagagagcctctccccttctggCaaagagccAgcagcttcatctccAagctcaaac aacacagcggccacaacagcagctattgtcccgggctcccagctgatgccttcaaaatcaccttccacaggCaccacagagatCagcag tcatgagtcctcccacggcaccccAtctcagacaacagccaagaactgggaactcacagcatccgcctcccaccagccgccaggtgtgt atccacagggccacagcgacaccact<u>GGCGGAGGAGGCTCTGGGGGCGGAGGAAGCGAACCTAA</u>

GTCCTCTGATAAGACCCACACATGTCCCCCCTGCCCAGCTCCTGAGCTCTTGGGCGG

ACCTTCCGTGTTTCTGTTCCCCCCAAAGCCCAAGGATACCCTTATGATCAGCAGAAC

ACCCGAAGTTACTTGCGTGGTCGTGGACGTTTCTCACGAAGATCCTGAAGTGAAATT

CAACTGGTACGTGGATGGCGTGGAGGTGCACAATGCTAAGACTAAGCCCCGTGAAG

AGCAGTACAACTCTACCTACCGGGTCGTTTCAGTGCTGACTGTTCTCCATCAGGACT

GGCTCAACGGGAAGGAGTATAAGTGCAAGGTGTCTAACAAGGCACTGCCCGCACCC

ATCGAGAAGACCATTTCTAAGGCCAAGGGTCAACCACGGGAGCCACAGGTTTACAC

ATTGCCTCCCAGTCGGGAGGAGATGACAAAGAATCAAGTGTCACTTACATGTCTTG

TGAAGGGCTTCTACCCCTCAGACATCGCCGTGGAGTGGGAGAGCAACGGACAACCA

GAAAACAACTACAAGACCACACCTCCTGTGCTCGATTCAGATGGTTCCTTTTTCTTG

TACAGCAAACTCACCGTTGACAAGAGTCGGTGGCAGCAAGGAAATGTGTTCAGCTG

TTCTGTGATGCACGAGGCCCTGCACAACCATTATACCCAAAAATCTCTCAGCCTTTC

TCCCGGCAAG.

DNA Sequence 6: (Fc-IL-15, nucleotide sequence encoding the precursor of protein sequence 6)

(SEQ ID NO: 44)

<u>ATGGACATGCGGGTGCCAGCCCAGCTGCTGGGCCTGTTGCTGCTGTGGTTCCCCGGC</u>

<u>TCTCGGTGC</u>GAACCTAAGTCCTCTGATAAGACCCACACATGTCCCCCCTGCCCAGCT

CCTGAGCTCTTGGGCGGACCTTCCGTGTTTCTGTTCCCCCCAAAGCCCAAGGATACC

CTTATGATCAGCAGAACACCCGAAGTTACTTGCGTGGTCGTGGACGTTTCTCACGAA

GATCCTGAAGTGAAATTCAACTGGTACGTGGATGGCGTGGAGGTGCACAATGCTAA

GACTAAGCCCCGTGAAGAGCAGTACAACTCTACCTACCGGGTCGTTTCAGTGCTGA

CTGTTCTCCATCAGGACTGGCTCAACGGGAAGGAGTATAAGTGCAAGGTGTCTAAC

AAGGCACTGCCCGCACCCATCGAGAAGACCATTTCTAAGGCCAAGGGTCAACCACG

GGAGCCACAGGTTTACACATTGCCTCCCAGTCGGGAGGAGATGACAAAGAATCAAG

```
TGTCACTTACATGTCTTGTGAAGGGCTTCTACCCCTCAGACATCGCCGTGGAGTGGG

AGAGCAACGGACAACCAGAAAACAACTACAAGACCACACCTCCTGTGCTCGATTCA

GATGGTTCCTTTTTCTTGTACAGCAAACTCACCGTTGACAAGAGTCGGTGGCAGCAA

GGAAATGTGTTCAGCTGTTCTGTGATGCACGAGGCCCTGCACAACCATTATACCCAA

AAATCTCTCAGCCTTTCTCCCGGCAAGGGCGGAGGAGGCTCTGGGGCGGAGGAAG

Caactgggtgaatgtaattagtgatttgaaaaaaattgaagatcttattcaatctatgcatattgatgctactttatatacggaaagtgatgttc acCCGagttgcaaagtaacagcaatgaagtgcttttctcttggagttacaagttatttcacttgagtccggcgatgcaagtattcatgatacag tagaaaatctgatcatcTTAgcaaacaacagtttgtcttctaatgggaatgtaacagaatctggatgcaaagaatgtgaggaactggagga aaaaaatattaaagaattttttgcagagttttgtacatattgtccaaatgttcatcaacacttct.
```

DNA Sequence 7: (Fc-IL-15Rα ECD, nucleotide sequence encoding the precursor of protein sequence 8)

(SEQ ID NO: 45)

```
ATGGACATGCGGGTGCCAGCCCAGCTGCTGGGCCTGTTGCTGCTGTGGTTCCCCGGC

TCTCGGTGCGAACCTAAGTCCTCTGATAAGACCCACACATGTCCCCCCTGCCCAGCT

CCTGAGCTCTTGGGCGGACCTTCCGTGTTTCTGTTCCCCCCAAAGCCCAAGGATACC

CTTATGATCAGCAGAACACCCGAAGTTACTTGCGTGGTCGTGGACGTTTCTCACGAA

GATCCTGAAGTGAAATTCAACTGGTACGTGGATGGCGTGGAGGTGCACAATGCTAA

GACTAAGCCCCGTGAAGAGCAGTACAACTCTACCTACCGGGTCGTTTCAGTGCTGA

CTGTTCTCCATCAGGACTGGCTCAACGGGAAGGAGTATAAGTGCAAGGTGTCTAAC

AAGGCACTGCCCGCACCCATCGAGAAGACCATTTCTAAGGCCAAGGGTCAACCACG

GGAGCCACAGGTTTACACATTGCCTCCCAGTCGGGAGGAGATGACAAAGAATCAAG

TGTCACTTACATGTCTTGTGAAGGGCTTCTACCCCTCAGACATCGCCGTGGAGTGGG

AGAGCAACGGACAACCAGAAAACAACTACAAGACCACACCTCCTGTGCTCGATTCA

GATGGTTCCTTTTTCTTGTACAGCAAACTCACCGTTGACAAGAGTCGGTGGCAGCAA

GGAAATGTGTTCAGCTGTTCTGTGATGCACGAGGCCCTGCACAACCATTATACCCAA

AAATCTCTCAGCCTTTCTCCCGGCAAGGGCGGAGGAGGCTCTGGGGCGGAGGAAG

CatcACCtgccctCCACCTatgtccgtggaacacgcagacatctgggtcaagagctacagcttgtactccCGCgagcgCtaca tttgtaactctggtttcaagcgtaaagccggcACCtccagcctgACCgagtgcgtgttgaacAAGGCCACCaatgtcgccac tggacaaccccAagtctcaaatgcattCGCgaccctgccctggttcaccaaCGCccagcgccaccAtccacagtaACCACTg caggCgtgaccccacagccagagagcctctccccttctggCaaagagccAgcagcttcatctccAagctcaaacaacacagcggcca caacagcagctattgtcccgggctcccagctgatgccttcaaaatcaccttccacaggCaccacagagatCagcagtcatgagtcctccc acggcaccccAtctcagacaacagccaagaactgggaactcacagcatccgcctccaccagccgccaggtgtgtatccacagggcca cagcgacaccact.
```

DNA Sequence 8: (IL-15-Fc-Knob, nucleotide sequence encoding the precursor of protein sequence 11)

(SEQ ID NO: 46)

```
ATGGACATGCGGGTGCCAGCCCAGCTGCTGGGCCTGTTGCTGCTGTGGTTCCCCGGC

TCTCGGTGCaactgggtgaatgtaATTagtgatttgaaaaaaattgaagatcttattcaatctatgcatattgatgctactttatatacg gaaagtgatgttcacCCGagttgcaaagtaacagcaatgaagtgatttctcttggagttacaagttatttcacttgagtccggcgatgcaagt attcatgatacagtagaaaatctgatcatcTTAgcaaacaacagtttgtcttctaatgggaatgtaacagaatctggatgcaaagaatgtga
``` ggaactggaggaaaaaaatattaaagaattttttgcagagttttgtacatattgtccaaatgttcatcaacacttct<u>GGCGGAGGAGG</u>

<u>CTCTGGGGGCGGAGGAAGC</u>GAACCTAAGTCCTCTGATAAGACCCACACATGTCCCC

CCTGCCCAGCTCCTGAGCTCTTGGGCGGACCTTCCGTGTTTCTGTTCCCCCCAAAGC

CCAAGGATACCCTTATGATCAGCAGAACACCCGAAGTTACTTGCGTGGTCGTGGAC

GTTTCTCACGAAGATCCTGAAGTGAAATTCAACTGGTACGTGGATGGCGTGGAGGT

GCACAATGCTAAGACTAAGCCCCGTGAAGAGCAGTACAACTCTACCTACCGGGTCG

TTTCAGTGCTGACTGTTCTCCATCAGGACTGGCTCAACGGGAAGGAGTATAAGTGC

AAGGTGTCTAACAAGGCACTGCCCGCACCCATCGAGAAGACCATTTCTAAGGCCAA

GGGTCAACCACGGGAGCCACAGGTTTACACATTGCCTCCCAGTCGGGAGGAGATGA

CAAAGAATCAAGTGTCA<u>CTTTAC</u>TGTCTTGTGAAGGGCTTCTACCCCTCAGACATCG

CCGTGGAGTGGGAGAGCAACGGACAACCAGAAAACAACTACAAGACCACACCTCC

TGTGCTCGATTCAGATGGTTCCTTTTTCTTGTACAGCAAACTCACCGTTGACAAGAG

TCGGTGGCAGCAAGGAAATGTGTTCAGCTGTTCTGTGATGCACGAGGCCCTGCACA

ACCATTATACCCAAAAATCTCTCAGCCTTTCTCCCGGCAAG.

DNA Sequence 9: (IL-15-Fc-Hole, nucleotide sequence encoding the precursor of protein sequence 12)

(SEQ ID NO: 47)

<u>ATGGACATGCGGGTGCCAGCCCAGCTGCTGGGCCTGTTGCTGCTGTGGTTCCCCGGC</u>

<u>TCTCGGTGC</u>aactgggtgaatgtaATTagtgatttgaaaaaaattgaagatcttattcaatctatgcatattgatgctactttatatacg gaaagtgatgttcacCCGagttgcaaagtaacagcaatgaagtgctttctcttggagttacaagttatttcacttgagtccggcgatgcaagt attcatgatacagtagaaaatctgatcatcTTAgcaaacaacagtttgtcttctaatgggaatgtaacagaatctggatgcaaagaatgtga ggaactggaggaaaaaaatattaaagaattttttgcagagttttgtacatattgtccaaatgttcatcaacacttct<u>GGCGGAGGAGG</u>

<u>CTCTGGGGGCGGAGGAAGC</u>GAACCTAAGTCCTCTGATAAGACCCACACATGTCCCC

CCTGCCCAGCTCCTGAGCTCTTGGGCGGACCTTCCGTGTTTCTGTTCCCCCCAAAGC

CCAAGGATACCCTTATGATCAGCAGAACACCCGAAGTTACTTGCGTGGTCGTGGAC

GTTTCTCACGAAGATCCTGAAGTGAAATTCAACTGGTACGTGGATGGCGTGGAGGT

GCACAATGCTAAGACTAAGCCCCGTGAAGAGCAGTACAACTCTACCTACCGGGTCG

TTTCAGTGCTGACTGTTCTCCATCAGGACTGGCTCAACGGGAAGGAGTATAAGTGC

AAGGTGTCTAACAAGGCACTGCCCGCACCCATCGAGAAGACCATTTCTAAGGCCAA

GGGTCAACCACGGGAGCCACAGGTTTACACATTGCCTCCCAGTCGGGAGGAGATGA

CAAAGAATCAAGTGTCACTTACATGTCTTGTGAAGGGCTTCTACCCCTCAGACATCG

CCGTGGAGTGGGAGAGCAACGGACAACCAGAAAACAACTACAAGACCACACCTCC

TGTGCTCGATTCAGATGGTTCCTTTTTC<u>TTGACC</u>AGCAAACTCACCGTTGACAAGAG

TCGGTGGCAGCAAGGAAATGTGTTCAGCTGTTCTGTGATGCACGAGGCCCTGCACA

ACCATTATACCCAAAAATCTCTCAGCCTTTCTCCCGGCAAG.

DNA Sequence 10: (Fc-Knob-IL-15, nucleotide sequence encoding the precursor of protein sequence 13)

(SEQ ID NO: 48)

<u>ATGGACATGCGGGTGCCAGCCCAGCTGCTGGGCCTGTTGCTGCTGTGGTT</u>

<u>CCCCGGCTCTCGGTGC</u>GAACCTAAGTCCTCTGATAAGACCCACACATGTC

CCCCCTGCCCAGCTCCTGAGCTCTTGGGCGGACCTTCCGTGTTTCTGTTC

CCCCCAAAGCCCAAGGATACCCTTATGATCAGCAGAACACCCGAAGTTAC

TTGCGTGGTCGTGGACGTTTCTCACGAAGATCCTGAAGTGAAATTCAACT

GGTACGTGGATGGCGTGGAGGTGCACAATGCTAAGACTAAGCCCCGTGAA

GAGCAGTACAACTCTACCTACCGGGTCGTTTCAGTGCTGACTGTTCTCCA

TCAGGACTGGCTCAACGGGAAGGAGTATAAGTGCAAGGTGTCTAACAAGG

CACTGCCCGCACCCATCGAGAAGACCATTTCTAAGGCCAAGGGTCAACCA

CGGGAGCCACAGGTTTACACATTGCCTCCCAGTCGGGAGGAGATGACAAA

GAATCAAGTGTCA<u>CTTTAC</u>TGTCTTGTGAAGGGCTTCTACCCCTCAGACA

TCGCCGTGGAGTGGGAGAGCAACGGACAACCAGAAAACAACTACAAGACC

ACACCTCCTGTGCTCGATTCAGATGGTTCCTTTTTCTTGTACAGCAAACT

CACCGTTGACAAGAGTCGGTGGCAGCAAGGAAATGTGTTCAGCTGTTCTG

TGATGCACGAGGCCCTGCACAACCATTATACCCAAAAATCTCTCAGCCTT

TCTCCCGGCAAGaactgggtgaatgtaATTagtgatttgaaaaaaattga agatcttattcaatctatgcatattgatgctactttatatacggaaagtg atgttcacCCGagttgcaaagtaacagcaatgaagtgctttctcttggag ttacaagttatttcacttgagtccggcgatgcaagtattcatgatacagt agaaaatctgatcatcTTAgcaaacaacagtttgtcttctaatgggaatg taacagaatctggatgcaaagaatgtgaggaactggaggaaaaaaatatt aaagaattttttgcagagttttgtacatattgtccaaatgttcatcaacac ttct.

DNA Sequence 11: (Fc-Hole-IL-15, nucleotide sequence encoding the precursor of protein sequence 14)

(SEQ ID NO: 49)

<u>ATGGACATGCGGGTGCCAGCCCAGCTGCTGGGCCTGTTGCTGCTGTGGTT</u>

<u>CCCCGGCTCTCGGTGC</u>GAACCTAAGTCCTCTGATAAGACCCACACATGTC

CCCCCTGCCCAGCTCCTGAGCTCTTGGGCGGACCTTCCGTGTTTCTGTTC

CCCCCAAAGCCCAAGGATACCCTTATGATCAGCAGAACACCCGAAGTTAC

TTGCGTGGTCGTGGACGTTTCTCACGAAGATCCTGAAGTGAAATTCAACT

GGTACGTGGATGGCGTGGAGGTGCACAATGCTAAGACTAAGCCCCGTGAA

GAGCAGTACAACTCTACCTACCGGGTCGTTTCAGTGCTGACTGTTCTCCA

TCAGGACTGGCTCAACGGGAAGGAGTATAAGTGCAAGGTGTCTAACAAGG

CACTGCCCGCACCCATCGAGAAGACCATTTCTAAGGCCAAGGGTCAACCA

CGGGAGCCACAGGTTTACACATTGCCTCCCAGTCGGGAGGAGATGACAAA

GAATCAAGTGTCACTTACATGTCTTGTGAAGGGCTTCTACCCCTCAGACA

TCGCCGTGGAGTGGGAGAGCAACGGACAACCAGAAAACAACTACAAGACC

ACACCTCCTGTGCTCGATTCAGATGGTTCCTTTTTC<u>TTGACC</u>AGCAAACT

CACCGTTGACAAGAGTCGGTGGCAGCAAGGAAATGTGTTCAGCTGTTCTG

TGATGCACGAGGCCCTGCACAACCATTATACCCAAAAATCTCTCAGCCTT

TCTCCCGGCAAGaactgggtgaatgtaATTagtgatttgaaaaaaattga agatcttattcaatctatgcatattgatgctactttatatacggaaagtg atgttcacCCGagttgcaaagtaacagcaatgaagtgctttctcttggag ttacaagttatttcacttgagtccggcgatgcaagtattcatgatacagt agaaaatctgatcatcTTAgcaaacaacagtttgtcttctaatgggaatg taacagaatctggatgcaaagaatgtgaggaactggaggaaaaaaatatt aaagaattttttgcagagttttgtacatattgtccaaatgttcatcaacac ttct.

DNA Sequence 12: (IL-15Rα ECD-Fc-Knob, nucleotide sequence encoding the precursor of protein sequence 15)

(SEQ ID NO: 50)

<u>ATGGACATGCGGGTGCCAGCCCAGCTGCTGGGCCTGTTGCTGCTGTGGTTCCCCGGC</u>

<u>TCTCGGTGC</u>atcACCtgccctCCACCTatgtccgtggaacacgcagacatctgggtcaagagctacagcttgtactccCG CgagcgCtacatttgtaactctggtttcaagcgtaaagccggcACCtccagcctgACCgagtgcgtgttgaacAAGGCCAC CaatgtcgcccactggacaaccccAagtctcaaatgcattCGCgaccctgccctggttcaccaaCGCccagcgccaccAtccaca gtaACCACTgcaggCgtgaccccacagccagagagcctctcccttctggCaaagagccAgcagcttcatctccAagctcaaac aacacagcggccacaacagcagctattgtcccgggctcccagctgatgccttcaaaatcaccttccacaggCaccacagagatCagcag tcatgagtcctcccacggcaccccAtctcagacaacagccaagaactgggaactcacagcatccgcctccaccagccgccaggtgtgt atccacagggccacagcgacaccact<u>GGCGGAGGAGGCTCTGGGGGCGGAGGAAGCGAACCTAA</u>

GTCCTCTGATAAGACCCACACATGTCCCCCCTGCCCAGCTCCTGAGCTCTTGGGCGG

ACCTTCCGTGTTTCTGTTCCCCCAAAGCCCAAGGATACCCTTATGATCAGCAGAAC

ACCCGAAGTTACTTGCGTGGTCGTGGACGTTTCTCACGAAGATCCTGAAGTGAAATT

CAACTGGTACGTGGATGGCGTGGAGGTGCACAATGCTAAGACTAAGCCCCGTGAAG

AGCAGTACAACTCTACCTACCGGGTCGTTTCAGTGCTGACTGTTCTCCATCAGGACT

GGCTCAACGGGAAGGAGTATAAGTGCAAGGTGTCTAACAAGGCACTGCCCGCACCC

ATCGAGAAGACCATTTCTAAGGCCAAGGGTCAACCACGGGAGCCACAGGTTTACAC

ATTGCCTCCCAGTCGGGAGGAGATGACAAAGAATCAAGTGTCA<u>CTTTAC</u>TGTCTTGT

GAAGGGCTTCTACCCCTCAGACATCGCCGTGGAGTGGGAGAGCAACGGACAACCAG

AAAACAACTACAAGACCACACCTCCTGTGCTCGATTCAGATGGTTCCTTTTTCTTGT

ACAGCAAACTCACCGTTGACAAGAGTCGGTGGCAGCAAGGAAATGTGTTCAGCTGT

TCTGTGATGCACGAGGCCCTGCACAACCATTATACCCAAAAATCTCTCAGCCTTTCT

CCCCGGCAAG.

DNA Sequence 13: (IL-15Rα ECD-Fc-Hole, nucleotide sequence encoding the precursor of protein sequence 16)

(SEQ ID NO: 51)

<u>ATGGACATGCGGGTGCCAGCCCAGCTGCTGGGCCTGTTGCTGCTGTGGTTCCCCGGC</u>

<u>TCTCGGTGC</u>atcACCtgccctCCACCTatgtccgtggaacacgcagacatctgggtcaagagctacagcttgtactccCG CgagcgCtacatttgtaactctggtttcaagcgtaaagccggcACCtccagcctgACCgagtgcgtgttgaacAAGGCCAC CaatgtcgcccactggacaaccccAagtctcaaatgcattCGCgaccctgccctggttcaccaaCGCccagcgccaccAtccaca gtaACCACTgcaggCgtgaccccacagccagagagcctctcccttctggCaaagagccAgcagcttcatctccAagctcaaac aacacagcggccacaacagcagctattgtcccgggctcccagctgatgccttcaaaatcaccttccacaggCaccacagagatCagcag tcatgagtcctcccacggcaccccAtctcagacaacagccaagaactgggaactcacagcatccgcctcccaccagccgccaggtgtgt atccacagggccacagcgacaccact<u>GGCGGAGGAGGCTCTGGGGGCGGAGGAAGC</u>GAACCTAA

GTCCTCTGATAAGACCCACACATGTCCCCCCTGCCCAGCTCCTGAGCTCTTGGGCGG

ACCTTCCGTGTTTCTGTTCCCCCCAAAGCCCAAGGATACCCTTATGATCAGCAGAAC

ACCCGAAGTTACTTGCGTGGTCGTGGACGTTTCTCACGAAGATCCTGAAGTGAAATT

CAACTGGTACGTGGATGGCGTGGAGGTGCACAATGCTAAGACTAAGCCCCGTGAAG

AGCAGTACAACTCTACCTACCGGGTCGTTTCAGTGCTGACTGTTCTCCATCAGGACT

GGCTCAACGGGAAGGAGTATAAGTGCAAGGTGTCTAACAAGGCACTGCCCGCACCC

ATCGAGAAGACCATTTCTAAGGCCAAGGGTCAACCACGGGAGCCACAGGTTTACAC

ATTGCCTCCCAGTCGGGAGGAGATGACAAAGAATCAAGTGTCACTTACATGTCTTG

TGAAGGGCTTCTACCCCTCAGACATCGCCGTGGAGTGGGAGAGCAACGGACAACCA

GAAAACAACTACAAGACCACACCTCCTGTGCTCGATTCAGATGGTTCCTTTTT<u>CTTG</u>

<u>ACC</u>AGCAAACTCACCGTTGACAAGAGTCGGTGGCAGCAAGGAAATGTGTTCAGCTG

TTCTGTGATGCACGAGGCCCTGCACAACCATTATACCCAAAAATCTCTCAGCCTTTC

TCCCGGCAAG.

DNA Sequence 14: (Fc-Knob-IL-15Rα ECD, nucleotide sequence encoding the precursor of protein sequence 17)

(SEQ ID NO: 52)

<u>ATGGACATGCGGGTGCCAGCCCAGCTGCTGGGCCTGTTGCTGCTGTGGTT</u>

<u>CCCCGGCTCTCGGTGC</u>GAACCTAAGTCCTCTGATAAGACCCACACATGTC

CCCCCTGCCCAGCTCCTGAGCTCTTGGGCGGACCTTCCGTGTTTCTGTTC

CCCCCAAAGCCCAAGGATACCCTTATGATCAGCAGAACACCCGAAGTTAC

TTGCGTGGTCGTGGACGTTTCTCACGAAGATCCTGAAGTGAAATTCAACT

GGTACGTGGATGGCGTGGAGGTGCACAATGCTAAGACTAAGCCCCGTGAA

GAGCAGTACAACTCTACCTACCGGGTCGTTTCAGTGCTGACTGTTCTCCA

TCAGGACTGGCTCAACGGGAAGGAGTATAAGTGCAAGGTGTCTAACAAGG

CACTGCCCGCACCCATCGAGAAGACCATTTCTAAGGCCAAGGGTCAACCA

CGGGAGCCACAGGTTTACACATTGCCTCCCAGTCGGGAGGAGATGACAAA

-continued
GAATCAAGTGTCA<u>CTTTAC</u>TGTCTTGTGAAGGGCTTCTACCCCTCAGACA

TCGCCGTGGAGTGGGAGAGCAACGGACAACCAGAAAACAACTACAAGACC

ACACCTCCTGTGCTCGATTCAGATGGTTCCTTTTTCTTGTACAGCAAACT

CACCGTTGACAAGAGTCGGTGGCAGCAAGGAAATGTGTTCAGCTGTTCTG

TGATGCACGAGGCCCTGCACAACCATTATACCCAAAAATCTCTCAGCCTT

TCTCCCGGCAAGatcACCtgccctCCACCTatgtccgtggaacacgcaga catctgggtcaagagctacagcttgtactccCGCgagcgCtacatttgta actctggtttcaagcgtaaagccggcACCtccagcctgACCgagtgcgtg ttgaacAAGGCCACCaatgtcgcccactggacaaccccAagtctcaaatg cattCGCgaccctgccctggttcaccaaCGCccagcgccaccAtccacag taACCACTgcaggCgtgaccccacagccagagagcctctcccttctggC aaagagccAgcagcttcatctccAagctcaaacaacacagcggccacaac agcagctattgtcccgggctcccagctgatgccttcaaaatcaccttcca caggCaccacagagatCagcagtcatgagtcctcccacggcaccccAtct cagacaacagccaagaactgggaactcacagcatccgcctcccaccagcc gccaggtgtgtatccacagggccacagcgacaccact.

DNA Sequence 15: (Fc-Hole-IL-15Rα ECD, nucleotide sequence encoding the precursor of protein sequence 18)

(SEQ ID NO: 53)
<u>ATGGACATGCGGGTGCCAGCCCAGCTGCTGGGCCTGTTGCTGCTGTGGTT</u>

<u>CCCCGGCTCTCGGTGC</u>GAACCTAAGTCCTCTGATAAGACCCACACATGTC

CCCCCTGCCCAGCTCCTGAGCTCTTGGGCGGACCTTCCGTGTTTCTGTTC

CCCCCAAAGCCCAAGGATACCCTTATGATCAGCAGAACACCCGAAGTTAC

TTGCGTGGTCGTGGACGTTTCTCACGAAGATCCTGAAGTGAAATTCAACT

GGTACGTGGATGGCGTGGAGGTGCACAATGCTAAGACTAAGCCCCGTGAA

GAGCAGTACAACTCTACCTACCGGGTCGTTTCAGTGCTGACTGTTCTCCA

TCAGGACTGGCTCAACGGGAAGGAGTATAAGTGCAAGGTGTCTAACAAGG

CACTGCCCGCACCCATCGAGAAGACCATTTCTAAGGCCAAGGGTCAACCA

CGGGAGCCACAGGTTTACACATTGCCTCCCAGTCGGGAGGAGATGACAAA

GAATCAAGTGTCACTTACATGTCTTGTGAAGGGCTTCTACCCCTCAGACA

TCGCCGTGGAGTGGGAGAGCAACGGACAACCAGAAAACAACTACAAGACC

ACACCTCCTGTGCTCGATTCAGATGGTTCCTTTTTC<u>TTGACC</u>AGCAAACT

CACCGTTGACAAGAGTCGGTGGCAGCAAGGAAATGTGTTCAGCTGTTCTG

TGATGCACGAGGCCCTGCACAACCATTATACCCAAAAATCTCTCAGCCTT

TCTCCCGGCAAGatcACCtgccctCCACCTatgtccgtggaacacgcaga catctgggtcaagagctacagcttgtactccCGCgagcgCtacatttgta actctggtttcaagcgtaaagccggcACCtccagcctgACCgagtgcgtg ttgaacAAGGCCACCaatgtcgcccactggacaaccccAagtctcaaatg cattCGCgaccctgccctggttcaccaaCGCccagcgccaccAtccacag taACCACTgcaggCgtgaccccacagccagagagcctctcccttctggC aaagagccAgcagcttcatctccAagctcaaacaacacagcggccacaac agcagctattgtcccgggctcccagctgatgccttcaaaatcaccttcca caggCaccacagagatCagcagtcatgagtcctcccacggcaccccAtct cagacaacagccaagaactgggaactcacagcatccgcctcccaccagcc gccaggtgtgtatccacagggccacagcgacaccact.

DNA Sequence 16: (Fc-Knob, nucleotide sequence encoding the precursor of protein sequence 23)

(SEQ ID NO: 54)
<u>ATGGACATGCGGGTGCCAGCCCAGCTGCTGGGCCTGTTGCTGCTGTGGTT</u>

<u>CCCCGGCTCTCGGTGC</u>GAACCTAAGTCCTCTGATAAGACCCACACATGTC

CCCCCTGCCCAGCTCCTGAGCTCTTGGGCGGACCTTCCGTGTTTCTGTTC

CCCCCAAAGCCCAAGGATACCCTTATGATCAGCAGAACACCCGAAGTTAC

TTGCGTGGTCGTGGACGTTTCTCACGAAGATCCTGAAGTGAAATTCAACT

GGTACGTGGATGGCGTGGAGGTGCACAATGCTAAGACTAAGCCCCGTGAA

GAGCAGTACAACTCTACCTACCGGGTCGTTTCAGTGCTGACTGTTCTCCA

TCAGGACTGGCTCAACGGGAAGGAGTATAAGTGCAAGGTGTCTAACAAGG

CACTGCCCGCACCCATCGAGAAGACCATTTCTAAGGCCAAGGGTCAACCA

CGGGAGCCACAGGTTTACACATTGCCTCCCAGTCGGGAGGAGATGACAAA

GAATCAAGTGTCA<u>CTTTAC</u>TGTCTTGTGAAGGGCTTCTACCCCTCAGACA

TCGCCGTGGAGTGGGAGAGCAACGGACAACCAGAAAACAACTACAAGACC

ACACCTCCTGTGCTCGATTCAGATGGTTCCTTTTTCTTGTACAGCAAACT

CACCGTTGACAAGAGTCGGTGGCAGCAAGGAAATGTGTTCAGCTGTTCTG

TGATGCACGAGGCCCTGCACAACCATTATACCCAAAAATCTCTCAGCCTT

TCTCCCGGCAAG.

DNA Sequence 17: (Fc-Hole, nucleotide sequence encoding the precursor of protein sequence 24)

(SEQ ID NO: 55)
<u>ATGGACATGCGGGTGCCAGCCCAGCTGCTGGGCCTGTTGCTGCTGTGGTT</u>

<u>CCCCGGCTCTCGGTGC</u>GAACCTAAGTCCTCTGATAAGACCCACACATGTC

CCCCCTGCCCAGCTCCTGAGCTCTTGGGCGGACCTTCCGTGTTTCTGTTC

CCCCCAAAGCCCAAGGATACCCTTATGATCAGCAGAACACCCGAAGTTAC

TTGCGTGGTCGTGGACGTTTCTCACGAAGATCCTGAAGTGAAATTCAACT

GGTACGTGGATGGCGTGGAGGTGCACAATGCTAAGACTAAGCCCCGTGAA

GAGCAGTACAACTCTACCTACCGGGTCGTTTCAGTGCTGACTGTTCTCCA

TCAGGACTGGCTCAACGGGAAGGAGTATAAGTGCAAGGTGTCTAACAAGG

CACTGCCCGCACCCATCGAGAAGACCATTTCTAAGGCCAAGGGTCAACCA

CGGGAGCCACAGGTTTACACATTGCCTCCCAGTCGGGAGGAGATGACAAA

GAATCAAGTGTCACTTACATGTCTTGTGAAGGGCTTCTACCCCTCAGACA

TCGCCGTGGAGTGGGAGAGCAACGGACAACCAGAAAACAACTACAAGACC

ACACCTCCTGTGCTCGATTCAGATGGTTCCTTTTTC<u>TTGACC</u>AGCAAACT

CACCGTTGACAAGAGTCGGTGGCAGCAAGGAAATGTGTTCAGCTGTTCTG

TGATGCACGAGGCCCTGCACAACCATTATACCCAAAAATCTCTCAGCCTT

TCTCCCGGCAAG.

DNA Sequence 18: (Fc-Knob (M)-IL-15, nucleotide sequence encoding the precursor of protein sequence 30)

(SEQ ID NO: 56)
<u>ATGGAGTTTGGGCTGAGCTGGCTTTTTCTTGTCGCGATTCTTAAGGGTGT</u>

<u>CCAGTGC</u>GAGCCCAAATCTAGTGACAAAACTCACACGTCCCCACCGTCCC

CAGCACCTGAACTCCTGGGGGACCGTCAGTCTTCCTCTTCCCCCCAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAAGAGCAGTAC

AACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTACACCCTGCCCCCATGCCGGGATGAGCTGACCAAGAACCAGGT

CAGCCTGTGGTGCCTGGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCTACAGCAAGCTCACCGTGGA

CAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGT

<u>AAAGGCGGAGGAGGCTCTGGCGGTGGTGGCAGTGGTGGCGGAGGGTCAGG</u>

<u>AGGTGGTGGAAGC</u>AACTGGGTGAATGTAATTAGTGATTTGAAAAAAATTG

AAGATCTTATTCAATCTATGCATATTGATGCTACTTTATATACGGAAAGT

GATGTTCACCCGAGTTGCAAAGTAACAGCAATGAAGTGCTTTCTCTTGGA

GTTACAAGTTATTTCACTTGAGTCCGGCGATGCAAGTATTCATGATACAG

TAGAAAATCTGATCATCTTAGCAAACAACAGTTTGTCTTCTAATGGGAAT

GTAACAGAATCTGGATGCAAAGAATGTGAGGAACTGGAGGAAAAAAATAT

TAAAGAATTTTTGCAGAGTTTTGTACATATTGTCCAAATGTTCATCAACA

CTTCT.

DNA Sequence 19: (IL-15-Fc-Knob (M), nucleotide sequence encoding the precursor of protein sequence 31)

(SEQ ID NO: 57)
<u>ATGGACATGCGGGTGCCAGCCCAGCTGCTGGGCCTGTTGCTGCTGTGGTT</u>

<u>CCCCGGCTCTCGGTGC</u>AACTGGGTGAATGTAATTAGTGATTTGAAAAAA

TTGAAGATCTTATTCAATCTATGCATATTGATGCTACTTTATATACGGAA

AGTGATGTTCACCCGAGTTGCAAAGTAACAGCAATGAAGTGCTTTCTCTT

GGAGTTACAAGTTATTTCACTTGAGTCCGGCGATGCAAGTATTCATGATA

CAGTAGAAAATCTGATCATCTTAGCAAACAACAGTTTGTCTTCTAATGGG

AATGTAACAGAATCTGGATGCAAAGAATGTGAGGAACTGGAGGAAAAAA

TATTAAAGAATTTTTGCAGAGTTTTGTACATATTGTCCAAATGTTCATCA

ACACTTCTGGCGGAGGAGGCTCTGGGGGCGGAGGATCCGAGCCCAAATCT

AGTGACAAAACTCACACGAGCCCACCGAGCCCAGCACCTGAACTCCTGGG

GGGACCGTCAGTCTTCCTCTTCCCCCCAAAACCCAAGGACACCCTCATGA

TCTCCCGGACCCCTGAGGTCACATGCGTGGTGGTGGACGTGAGCCACGAA

GACCCTGAGGTCAAGTTCAACTGGTACGTGGACGGCGTGGAGGTGCATAA

TGCCAAGACAAAGCCGCGGGAAGAGCAGTACAACAGCAGTACCGTGTGGT

CAGCGTCCTCACCGTCCTGCACCAGGACTGGCTGAATGGCAAGGAGTACA

AGTGCAAGGTCTCCAACAAAGCCCTCCCAGCCCCCATCGAGAAAACCATC

TCCAAAGCCAAAGGGCAGCCCCGAGAACCACAGGTGTACACCCTGCCCCC

ATGCCGGGATGAGCTGACCAAGAACCAGGTCAGCCTGTGGTGCCTGGTCA

AAGGCTTCTATCCCAGCGACATCGCCGTGGAGTGGGAGAGCAATGGGCAG

CCGGAGAACAACTACAAGACCACGCCTCCCGTGCTGGACTCCGACGGCTC

CTTCTTCCTCTACAGCAAGCTCACCGTGGACAAGAGCAGGTGGCAGCAGG

GGAACGTCTTCTCATGCTCCGTGATGCATGAGGCTCTGCACAACCACTAC

ACGCAGAAGAGCCTCTCCCTGTCTCCGGGTAAA.

DNA Sequence 20: (Fc-Hole (M)-IL-15Rα-sushi (65), nucleotide sequence encoding the precursor of protein sequence 32)

(SEQ ID NO: 58)
<u>ATGGAGTTTGGGCTGAGCTGGCTTTTTCTTGTCGCGATTCTTAAGGGTGT</u>

<u>CCAGTGC</u>GAGCCCAAATCTAGTGACAAAACTCACACGTCCCCACCGTCCC

CAGCACCTGAACTCCTGGGGGACCGTCAGTCTTCCTCTTCCCCCCAAAA

CCCAAGGACACCCTCATGATCTCCCGGACCCCTGAGGTCACATGCGTGGT

GGTGGACGTGAGCCACGAAGACCCTGAGGTCAAGTTCAACTGGTACGTGG

ACGGCGTGGAGGTGCATAATGCCAAGACAAAGCCGCGGGAAGAGCAGTAC

AACAGCACGTACCGTGTGGTCAGCGTCCTCACCGTCCTGCACCAGGACTG

GCTGAATGGCAAGGAGTACAAGTGCAAGGTCTCCAACAAAGCCCTCCCAG

CCCCCATCGAGAAAACCATCTCCAAAGCCAAAGGGCAGCCCCGAGAACCA

CAGGTGTGCACCCTGCCCCCAtccGGGATGAGCTGACCAAGAACCAGGT

CAGCCTGAGCTGCGCCGTCAAAGGCTTCTATCCCAGCGACATCGCCGTGG

AGTGGGAGAGCAATGGGCAGCCGGAGAACAACTACAAGACCACGCCTCCC

GTGCTGGACTCCGACGGCTCCTTCTTCCTCGTGAGCAAGCTCACCGTGGA

CAAGAGCAGGTGGCAGCAGGGGAACGTCTTCTCATGCTCCGTGATGCATG

AGGCTCTGCACAACCACTACACGCAGAAGAGCCTCTCCCTGTCTCCGGGT

<u>AAAGGCGGAGGAGGCTCTGGCGGTGGTGGCAGTGGTGGCGGAGGGTCAGG</u>

<u>AGGTGGTGGAAGC</u>ATCACCTGCCCTCCACCTATGTCCGTGGAACACGCAG

ACATCTGGGTCAAGAGCTACAGCTTGTACTCCCGCGAGCGCTACATTTGT

AACTCTGGTTTCAAGCGTAAAGCCGGCACCTCCAGCCTGACCGAGTGCGT

GTTGAACAAGGCCACCAATGTCGCCCACTGGACAACCCCAAGTCTCAAAT

GCATTCGC.

DNA Sequence 21: (IL-15Rα-sushi (65)-Fc-Hole (M), nucleotide sequence encoding the precursor of protein sequence 33)

(SEQ ID NO: 59)
<u>ATGGACATGCGGGTGCCAGCCCAGCTGCTGGGCCTGTTGCTGCTGTGGTT</u>

<u>CCCCGGCTCTCGGTGC</u>ATCACCTGCCCTCCACCTATGTCCGTGGAACACG

CAGACATCTGGGTCAAGAGCTACAGCTTGTACTCCCGCGAGCGCTACATT

TGTAACTCTGGTTTCAAGCGTAAAGCCGGCACCTCCAGCCTGACCGAGTG

CGTGTTGAACAAGGCCACCAATGTCGCCCACTGGACAACCCCAAGTCTCA

AATGCATTCGC<u>GGAGGGGGTGGCAGCGGCGGGGGAGGTTCAGGCGGAGGT</u>

<u>GGGTCTGGAGGCGGTGGATCC</u>GAGCCCAAATCTAGTGACAAAACTCACAC

GTCCCCACCGTCCCCAGCACCTGAACTCCTGGGGGGACCGTCAGTCTTCC

TCTTCCCCCCAAAACCCAAGGACACCCTCATGATCTCCCGGACCCCTGAG

GTCACATGCGTGGTGGTGGACGTGAGCCACGAAGACCCTGAGGTCAAGTT

CAACTGGTACGTGGACGGCGTGGAGGTGCATAATGCCAAGACAAAGCCGC

GGGAAGAGCAGTACAACAGCACGTACCGTGTGGTCAGCGTCCTCACCGTC

CTGCACCAGGACTGGCTGAATGGCAAGGAGTACAAGTGCAAGGTCTCCAA

CAAAGCCCTCCCAGCCCCCATCGAGAAAACCATCTCCAAAGCCAAAGGGC

AGCCCCGAGAACCACAGGTGTGCACCCTGCCCCCATCCCGGGATGAGCTG

ACCAAGAACCAGGTCAGCCTGAGCTGCGCCGTCAAAGGCTTCTATCCCAG

CGACATCGCCGTGGAGTGGGAGAGCAATGGGCAGCCGGAGAACAACTACA

AGACCACGCCTCCCGTGCTGGACTCCGACGGCTCCTTCTTCCTCGTGAGC

AAGCTCACCGTGGACAAGAGCAGGTGGCAGCAGGGGAACGTCTTCTCATG

CTCCGTGATGCATGAGGCTCTGCACAACCACTACACGCAGAAGAGCCTCT

CCCTGTCTCCGGGTAAA.

DNA Sequence 22: (IL-15Rα-sushi (73)-Fc-Hole, nucleotide sequence encoding the precursor of protein sequence 34)

(SEQ ID NO: 60)
<u>ATGGACATGCGGGTGCCAGCCCAGCTGCTGGGCCTGTTGCTGCTGTGGTT</u>

<u>CCCCGGCTCTCGGTGC</u>ATCACCTGCCCTCCACCTATGTCCGTGGAACACG

CAGACATCTGGGTCAAGAGCTACAGCTTGTACTCCCGCGAGCGCTACATT

TGTAACTCTGGTTTCAAGCGTAAAGCCGGCACCTCCAGCCTGACCGAGTG

CGTGTTGAACAAGGCCACCAATGTCGCCCACTGGACAACCCCAAGTCTCA

AATGCATTCGCGACCCTGCCCTGGTTCACCAACGCT<u>CCGGCGGATCAGGA</u>

<u>GGTGGTGGCAGCGGGGGTGGTTCCGGTGGAGGGGGCTCCTTGCAGGAACC</u>

TAAGTCCTCTGATAAGACCCACACATGTCCCCCTGCCCAGCTCCTGAGC

TCTTGGGCGGACCTTCCGTGTTTCTGTTCCCCCCAAAGCCCAAGGATACC

CTTATGATCAGCAGAACACCCGAAGTTACTTGCGTGGTCGTGGACGTTTC

TCACGAAGATCCTGAAGTGAAATTCAACTGGTACGTGGATGGCGTGGAGG

TGCACAATGCTAAGACTAAGCCCCGTGAAGAGCAGTACAACTCTACCTAC

CGGGTCGTTTCAGTGCTGACTGTTCTCCATCAGGACTGGCTCAACGGGAA

GGAGTATAAGTGCAAGGTGTCTAACAAGGCACTGCCCGCACCCATCGAGA

AGACCATTTCTAAGGCCAAGGGTCAACCACGGGAGCCACAGGTTTACACA

TTGCCTCCCAGTCGGGAGGAGATGACAAAGAATCAAGTGTCACTTACATG

TCTTGTGAAGGGCTTCTACCCCTCAGACATCGCCGTGGAGTGGGAGAGCA

ACGGACAACCAGAAAACAACTACAAGACCACACCTCCTGTGCTCGATTCA

GATGGTTCCTTTTTCTTGACCAGCAAACTCACCGTTGACAAGAGTCGGTG

GCAGCAAGGAAATGTGTTCAGCTGTTCTGTGATGCACGAGGCCCTGCACA

ACCATTATACCCAAAAATCTCTCAGCCTTTCTCCCGGCAAG.

DNA Sequence 23: (IL-15Rα-sushi (65)-Fc-Hole, nucleotide sequence encoding the precursor of protein sequence 35)

(SEQ ID NO: 61)
<u>ATGGACATGCGGGTGCCAGCCCAGCTGCTGGGCCTGTTGCTGCTGTGGTT</u>

<u>CCCCGGCTCTCGGTGC</u>ATCACCTGCCCTCCACCTATGTCCGTGGAACACG

CAGACATCTGGGTCAAGAGCTACAGCTTGTACTCCCGCGAGCGCTACATT

TGTAACTCTGGTTTCAAGCGTAAAGCCGGCACCTCCAGCCTGACCGAGTG

CGTGTTGAACAAGGCCACCAATGTCGCCCACTGGACAACCCCAAGTCTCA

AATGCATTCGC<u>TCCGGCGGATCAGGAGGTGGTGGCAGCGGGGGTGGTTCC</u>

<u>GGTGGAGGGGGCTCCTTGCAG</u>GAACCTAAGTCCTCTGATAAGACCCACAC

ATGTCCCCCCTGCCCAGCTCCTGAGCTCTTGGGCGGACCTTCCGTGTTTC

TGTTCCCCCCAAAGCCCAAGGATACCCTTATGATCAGCAGAACACCCGAA

GTTACTTGCGTGGTCGTGGACGTTTCTCACGAAGATCCTGAAGTGAAATT

CAACTGGTACGTGGATGGCGTGGAGGTGCACAATGCTAAGACTAAGCCCC

GTGAAGAGCAGTACAACTCTACCTACCGGGTCGTTTCAGTGCTGACTGTT

CTCCATCAGGACTGGCTCAACGGGAAGGAGTATAAGTGCAAGGTGTCTAA

CAAGGCACTGCCCGCACCCATCGAGAAGACCATTTCTAAGGCCAAGGGTC

AACCACGGGAGCCACAGGTTTACACATTGCCTCCCAGTCGGGAGGAGATG

ACAAAGAATCAAGTGTCACTTACATGTCTTGTGAAGGGCTTCTACCCCTC

AGACATCGCCGTGGAGTGGGAGAGCAACGGACAACCAGAAAACAACTACA

AGACCACACCTCCTGTGCTCGATTCAGATGGTTCCTTTTTCTTGACCAGC

AAACTCACCGTTGACAAGAGTCGGTGGCAGCAAGGAAATGTGTTCAGCTG

TTCTGTGATGCACGAGGCCCTGCACAACCATTATACCCAAAAATCTCTCA

GCCTTTCTCCCGGCAAG.

DNA Sequence 24: (IL-15Rα-sushi (86)-Fc-Hole, nucleotide sequence encoding the precursor of protein sequence 36)

(SEQ ID NO: 62)
<u>ATGGACATGCGGGTGCCAGCCCAGCTGCTGGGCCTGTTGCTGCTGTGGTT</u>

<u>CCCCGGCTCTCGGTGC</u>ATCACCTGCCCTCCACCTATGTCCGTGGAACACG

CAGACATCTGGGTCAAGAGCTACAGCTTGTACTCCCGCGAGCGCTACATT

TGTAACTCTGGTTTCAAGCGTAAAGCCGGCACCTCCAGCCTGACCGAGTG

41

```
CGTGTTGAACAAGGCCACCAATGTCGCCCACTGGACAACCCCAAGTCTCA

AATGCATTCGCGACCCTGCCCTGGTTCACCAACGCCCAGCGCCACCATCC

ACAGTAACCACTGCAGGCGTGACCTCCGGCGGATCAGGAGGTGGTGGCAG

CGGGGGTGGTTCCGGTGGAGGGGGCTCCTTGCAGGAACCTAAGTCCTCTG

ATAAGACCCACACATGTCCCCCCTGCCCAGCTCCTGAGCTCTTGGGCGGA

CCTTCCGTGTTTCTGTTCCCCCCAAAGCCCAAGGATACCCTTATGATCAG

CAGAACACCCGAAGTTACTTGCGTGGTCGTGGACGTTTCTCACGAAGATC

CTGAAGTGAAATTCAACTGGTACGTGGATGGCGTGGAGGTGCACAATGCT

AAGACTAAGCCCCGTGAAGAGCAGTACAACTCTACCTACCGGGTCGTTTC

AGTGCTGACTGTTCTCCATCAGGACTGGCTCAACGGGAAGGAGTATAAGT

GCAAGGTGTCTAACAAGGCACTGCCCGCACCCATCGAGAAGACCATTTCT

AAGGCCAAGGGTCAACCACGGGAGCCACAGGTTTACACATTGCCTCCCAG

TCGGGAGGAGATGACAAAGAATCAAGTGTCACTTACATGTCTTGTGAAGG

GCTTCTACCCCTCAGACATCGCCGTGGAGTGGGAGAGCAACGGACAACCA

GAAAACAACTACAAGACCACACCTCCTGTGCTCGATTCAGATGGTTCCTT

TTTCTTGACCAGCAAACTCACCGTTGACAAGAGTCGGTGGCAGCAAGGAA

ATGTGTTCAGCTGTTCTGTGATGCACGAGGCCCTGCACAACCATTATACC

CAAAAATCTCTCAGCCTTTCTCCCGGCAAG.
```

DNA Sequence 25: (IL-15Rα-sushi (102)-Fc-Hole, nucleotide sequence encoding the precursor of protein sequence 37)

(SEQ ID NO: 63)
```
ATGGACATGCGGGTGCCAGCCCAGCTGCTGGGCCTGTTGCTGCTGTGGTT

CCCCGGCTCTCGGTGCATCACCTGCCCTCCACCTATGTCCGTGGAACACG

CAGACATCTGGGTCAAGAGCTACAGCTTGTACTCCCGCGAGCGCTACATT

TGTAACTCTGGTTTCAAGCGTAAAGCCGGCACCTCCAGCCTGACCGAGTG

CGTGTTGAACAAGGCCACCAATGTCGCCCACTGGACAACCCCAAGTCTCA

AATGCATTCGCGACCCTGCCCTGGTTCACCAACGCCCAGCGCCACCATCC

ACAGTAACCACTGCAGGCGTGACCCCACAGCCAGAGAGCCTCTCCCCTTC

TGGCAAAGAGCCAGCAGCTTCAGGCGGAGGAGGCTCTGGGGCGGAGGAA

GCGAACCTAAGTCCTCTGATAAGACCCACACATGTCCCCCTGCCCAGCT

CCTGAGCTCTTGGGCGGACCTTCCGTGTTTCTGTTCCCCCCAAAGCCCAA

GGATACCCTTATGATCAGCAGAACACCCGAAGTTACTTGCGTGGTCGTGG

ACGTTTCTCACGAAGATCCTGAAGTGAAATTCAACTGGTACGTGGATGGC

GTGGAGGTGCACAATGCTAAGACTAAGCCCCGTGAAGAGCAGTACAACTC

TACCTACCGGGTCGTTTCAGTGCTGACTGTTCTCCATCAGGACTGGCTCA

ACGGGAAGGAGTATAAGTGCAAGGTGTCTAACAAGGCACTGCCCGCACCC

ATCGAGAAGACCATTTCTAAGGCCAAGGGTCAACCACGGGAGCCACAGGT

TTACACATTGCCTCCCAGTCGGGAGGAGATGACAAAGAATCAAGTGTCAC

TTACATGTCTTGTGAAGGGCTTCTACCCCTCAGACATCGCCGTGGAGTGG

GAGAGCAACGGACAACCAGAAAACAACTACAAGACCACACCTCCTGTGCT

CGATTCAGATGGTTCCTTTTTTCTTGACCAGCAAACTCACCGTTGACAAGA

GTCGGTGGCAGCAAGGAAATGTGTTCAGCTGTTCTGTGATGCACGAGGCC

CTGCACAACCATTATACCCAAAAATCTCTCAGCCTTTCTCCCGGCAAG.
```

Example 3. Protein Expression

IL-15 protein was transiently transfected and expressed using FreeStyle 293 cells (GIBCO, Cat#R79007). FreeStyle 293 cells were suspension cultured in Freestyle 293 expression medium (GIBCO, Cat#12338018), followed by addition of Ultra Low IgG Fetal Bovine Serum (ultra low immunoglobulins FBS, GIBCO, Cat #16250078) to a final concentration of 1%. The corresponding expression plasmids described in Example 1 and transfection reagent PEI (Polysciences, Cat#239662) were prepared, and the plasmid amount was 100 ug/100 mL cells, and the ratio of plasmid to PEI was 1:2 by mass. Cell density on the day of transfection was $1\times10^6$/mL. 1 L of FreeStyle 293 cells was prepared for transfection. 50 mL of Opti-MEM (GIBCO, Cat #11058021) medium was mixed with the plasmid, kept still for 5 minutes, and filtered; and another 50 mL of Opti-MEM medium was mixed with PEI, kept still for 5 minutes and filtered. The plasmid was mixed with PEI and kept still for 15 minutes. The mixture of plasmid and PEI was slowly added to the cells and cultured in a shaking incubator at 130 rpm at 37° C., 8% $CO_2$. Five days later, the supernatant was collected by centrifugation for protein purification.

Example 4. Protein Purification (1) Affinity Chromatography for IL-15 Heterodimeric Protein:

Supernatant was collected from cell culture after high speed centrifugation and subjected to affinity chromatography using a Protein A column from GE. The equilibration buffer used for chromatography was 1×PBS (pH 7.4). After cell supernatant was loaded and bound, the column was washed with PBS until UV returned to baseline, and then the target protein was eluted with elution buffer 0.1 M glycine (pH3.0). The pH was adjusted to neutral with Tris, and the target protein was stored.

(2) Ion Exchange Chromatography for IL-15 Heterodimeric Protein:

The pH of the product obtained during the affinity chromatography was adjusted to be 1-2 pH units lower or higher than the pI, and appropriately diluted to control the conductivity of the sample to less than 5 ms/cm. Utilizing a suitable buffer corresponding to the pH, such as phosphate buffer, acetate buffer, and others, the product was NaCl-gradient eluted under the corresponding pH condition utilizing conventional ion-exchange column chromatography methods known in the art such as cation exchange or anion exchange, and the tube containing the target protein was selected according to SDS-PAGE and stored.

(3) Size Exclusion Chromatography for IL-15 Heterodimeric Protein:

The product obtained during the ion exchange chromatography was concentrated by ultrafiltration and loaded for size exclusion chromatography using, e.g., GE Superdex200 gel to remove possible polymers and other components in order to obtain the desired product with high purity. Purity of the obtained protein can be detected by SDS-PAGE and SEC-HPLC. Protein concentration was determined by UV spectrophotometry.

The obtained protein sequences are described in Example 1. Each specific heterodimeric protein was composed of one or two protein sequence(s) selected from the above sequences, preferably a heterodimeric protein formed with Knob/Hole pairing, which was co-expressed in cells, and obtained by purification. Alternatively, a bivalent protein can be composed of an Fc chain region without mutations. In a preferred embodiment, for example, molecule 3 was formed by pairing fusion protein IL-15-Fc-Knob with Fc-Hole (obtained by purification after co-expression), and molecule 7 in the examples was formed by pairing fusion proteins IL-15-Fc-Knob and IL-15RαECD-Fc-Hole (obtained by purification after co-expression). Non-limiting examples of a dimeric protein according to the present invention are shown in Table 1 below:

TABLE 1

Design for each dimeric protein

| No | Protein (I) | Protein (II) |
|---|---|---|
| 1 | IL-15-Fc (SEQ ID No: 8) | IL-15-Fc (SEQ ID No: 8) |
| 2 | Fc-IL-15 (SEQ ID No: 9) | Fc-IL-15 (SEQ ID No: 9) |
| 3 | IL-15-Fc-Knob (SEQ ID No: 14) | Fc-Hole (SEQ ID No: 27) |
| 4 | IL-15-Fc-Hole (SEQ ID No: 15) | Fc-Knob (SEQ ID No: 26) |
| 5 | Fc-Knob-IL-15 (SEQ ID No: 16) | Fc-Hole (SEQ ID No: 27) |
| 6 | Fc-Hole-IL-15 (SEQ ID No: 17) | Fc-Knob (SEQ ID No: 26) |
| 7 | IL-15-Fc-Knob (SEQ ID No: 14) | IL-15Rα ECD-Fc-Hole (SEQ ID No: 19) |
| 8 | IL-15-Fc-Hole (SEQ ID No: 15) | IL-15Rα ECD-Fc-Knob (SEQ ID No: 18) |
| 9 | Fc-Knob-IL-15 (SEQ ID No: 16) | Fc-Hole-IL-15Rα ECD (SEQ ID No: 21) |
| 10 | Fc-Hole-IL-15 (SEQ ID No: 17) | Fc-Knob-IL-15Rα ECD (SEQ ID No: 20) |
| 11 | IL-15-Fc-Knob (SEQ ID No: 14) | IL-15Rα-sushi (77)-Fc-Hole (SEQ ID No: 23) |
| 12 | Fc-Knob (M)-IL-15 (SEQ ID No: 30) | Fc-Hole(M)-IL-15Rα-sushi(65) (SEQ ID No: 32) |
| 13 | IL-15-Fc-Knob (M) (SEQ ID No: 31) | IL-15Rα-sushi (65)-Fc-Hole (M) (SEQ ID No: 33) |
| 14 | IL-15-Fc-Knob (SEQ ID No: 14) | IL-15Rα-sushi (73)-Fc-Hole (SEQ ID No: 34) |
| 15 | IL-15-Fc-Knob (SEQ ID No: 14) | IL-15Rα-sushi (65)-Fc-Hole (SEQ ID No: 35) |
| 16 | IL-15-Fc-Knob (SEQ ID No: 14) | IL-15Rα-sushi (86)-Fc-Hole (SEQ ID No: 36) |
| 17 | IL-15-Fc-Knob (SEQ ID No: 14) | IL-15Rα-sushi (102)-Fc-Hole (SEQ ID No: 37) |

Table 1 specifically shows 17 dimeric proteins involved in the present invention, named as dimeric proteins 1 to 17, respectively. Each was recombinantly produced by the corresponding protein (I) and protein (II) shown in the table.

Test Examples

Test Example 1. Proliferation Assay In Vitro

Testing the Proliferation of Fresh Human Peripheral Blood Mononuclear Cells (PBMCs) Affected by IL-15, and Dimeric Proteins 1 to 17 of the Present Invention.

Fresh PBMCs were cultured in RPMI1640 medium containing 10% FBS, and centrifuged and resuspended to a cell density of $5 \times 10^5$ cells/mL. Then, 90 uL was added into each well of a 96-well plate, samples were diluted at certain multiples to different concentrations with PBS, 10 uL was added into each well of a 96-well plate, and cultured in an incubator at 37° C., 5% $CO_2$ for 48 hours. Thereafter, 50 μL was taken for detection of cell proliferation with CellTiter-Glo® Luminescent Cell Viability Assay kit. The results are shown in Table 2:

TABLE 2

Results of the in vitro proliferation test

| Sample | PBMC relative activity |
|---|---|
| IL-15 (Control) | 100 |
| 1 | 79 |
| 2 | 46 |
| 3 | 367 |
| 5 | 138 |
| 7 | 1100 |
| 8 | 183 |
| 9 | 26 |
| 10 | 11 |
| 11 | 1392 |
| 12 | 210 |
| 13 | 206 |

TABLE 2-continued

Results of the in vitro proliferation test

| Sample | PBMC relative activity |
|---|---|
| 14 | 1243 |
| 15 | 1338 |
| 16 | 1024 |
| 17 | 2677 |

Experimental results in the test example: human PBMC proliferation assay showed that the effects of heterodimeric proteins 3, 7, 11 and 14-17 of the present invention on promoting proliferation are obviously superior to that of control IL-15, and are obviously superior to that of the homodimers 1 and 2. In addition, the fusion protein with the Fc variant located at the C-terminus has a better effect than the one with the Fc variant located at the N-terminus. The heterodimeric proteins 12 and 13 of other variant molecules also have a better effect on promoting proliferation than control IL-15.

Test Example 2. Detecting In Vivo PK of IL-15 Heterologous Dimer

Purpose

Evaluate the pharmacokinetics (PK) of IL-15 heterodimeric proteins 3 and 7 in mice.

Material and Methods

1. Test Compounds, that is Samples

IL-15, IL-15 heterodimeric proteins 3 and 7.

2. Animals

C57BL/6 mice, SPF, 15-16 g, ♂ (male), available from Shanghai Super B&K Laboratory Animal Corp. Ltd.

3. Animal Test Procedure

Twenty seven (27) of C57BL/6 mice were divided into 3 groups, 9 in each group, and 3 per cage. Blood samples of 3 mice were collected at each time point, and the blood was sampled from circulation. 2 μg of IL-15, 10 μg of dimeric protein 3 and 20 μg of dimeric protein 7 (IL-15, dimeric protein 3 and dimeric protein 7 have the same molar amount of 0.15 nmol) were intraperitoneally injected. Blood was sampled at 30 minutes, and 1, 2, 4, 8, 24, 48, 72, and 120 hours after administration, and 50-100 μl of orbital blood sample was taken at each time point. Serum was used for human IL-15 ELISA.

3. Results and Discussion

After administration of equimolar IL-15, dimeric protein 3 and dimeric protein 7, IL-15 reached a maximal concentration within 30 minutes, and then was rapidly metabolized over time and completely metabolized 24 hours after administration. The dimeric protein 3 reached a maximal concentration at 2 hours after administration, and then was slowly metabolized over time and completely metabolized 120 hours after administration. The dimeric protein 7 reached a maximal amount at 2 hours after administration, and then was slowly metabolized over time. 120 hours later, a high concentration of protein was still detected.

PK detection (FIG. 1) showed that after administration, the maximal molar concentrations of both dimeric protein 3 and dimeric protein 7 in the serum were less than that of IL-15, but their retention times in the serum were superior to that of IL-15, thus exhibiting a significant long-term effect.

Detecting the In Vivo Efficacy of IL-15

This example is to test the efficacy of IL-15, dimeric protein 3 and dimeric protein 7 in three models of lung metastasis, nude mice tumor-bearing model and severe combined immunodeficient NOD-SCID mice model. The results are shown in the following test examples.

Test Example 3. Lung Metastasis Model

Purpose

Establish mouse lung metastasis model using B16F10 cells to assess the impact on tumor metastasis and growth after administration of IL-15 drug.

Material and Protocol

1. Test Protein

IL-15, dimeric protein 3 and dimeric protein 7.

2. Test Animals

C57BL/6 mice, SPF, 10-16 g, ♂ (male), available from Shanghai Super B&K Laboratory Animal Corp. Ltd.

3. Animal Test Procedure

Dosage regimen: thirty two (32) C57BL/6 mice were divided into 4 groups, with 8 in each group. $1.5 \times 10^5$ of B16F10 cells were intravenously injected via the tail-vein. PBS, 2 μg of IL-15, 11 μg of dimeric protein 3 and 14 μg of dimeric protein 7 (IL-15, dimeric protein 3 and dimeric protein 7 have the same molar amount of 0.16 nmol) were intraperitoneally injected on days 1, 2, and 10.

Mice were sacrificed on day 21. Lungs were removed, weighed, observed for black lumps in the lung, photographed, fixed in neutral formalin, and the number of black lumps was counted.

3. Results

Figure 2:
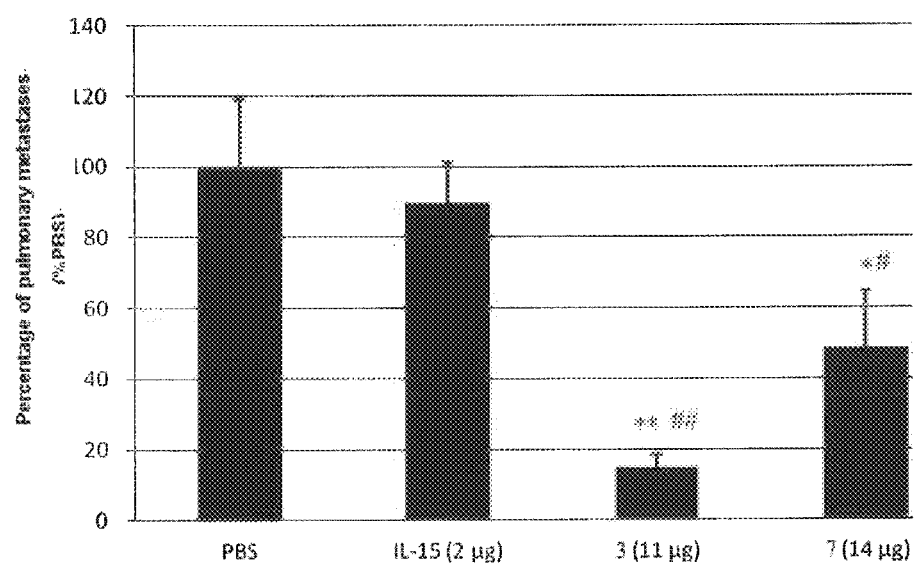
FIG. 2 shows the number of metastatic lumps in lung in dosing mice in the lung metastasis model of Test Example 3; * in the figure represents p<0.05, vs PBS; ** represents p<0.01, vs PBS; and ## represents p<0.01, vs IL-15.
Figure 3:
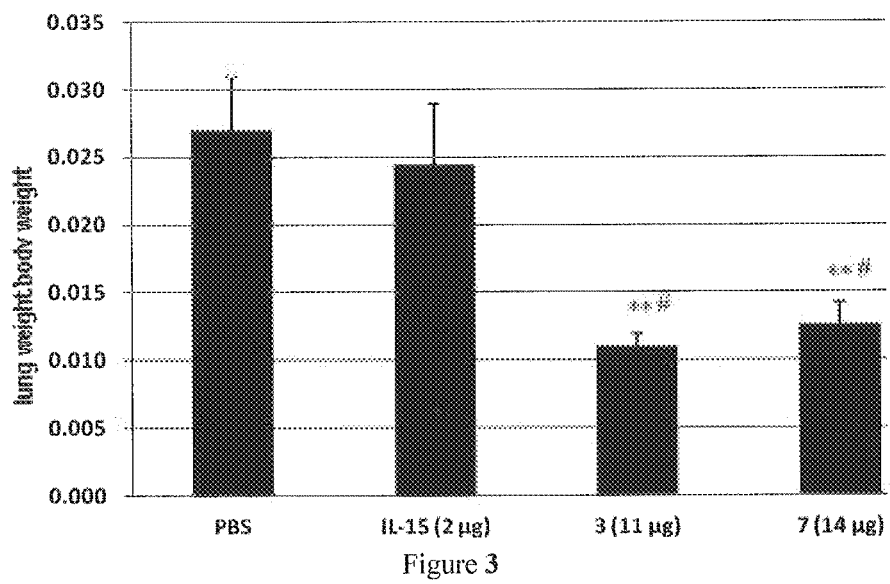
FIG. 3 shows the relative lung weight (lung weight/body weight) in dosing mice in the lung metastasis model of Test Example 3; ** in the figure represents p<0.01, vs PBS; and # represents p<0.05, vs IL-15.

In the dosage regimen, lungs of mice in the PBS group showed growth of a large number of metastatic melanoma (175±23); lungs of the IL-15 group showed a large number of melanoma lumps (157±20), about 90% of that in the PBS group; lungs of the dimeric protein 3 group exhibited a few metastatic melanoma lumps (26±6), about 15% of that in the PBS group; and lungs of dimeric protein 7 group showed more visible lung metastatic melanoma lumps (83±28), about 49% of that in the PBS group. The number of lung lumps in the PBS group was significantly higher than that in dimeric protein 3 group and dimeric protein 7 group, but showed no significant difference from that in the IL-15 group. The number of lung lumps in the IL-15 group was significantly higher than that in the dimeric protein 3 group. The number of lung lumps in the dimeric protein 7 group was significantly higher than that in the dimeric protein 3 group, as shown in FIG. 2. The relative lung weight in the PBS group was significantly higher than that in the dimeric protein 3 group and the dimeric protein 7 group, but showed no significant difference from that in the IL-15 group. The relative lung weight in the IL-15 group was significantly higher than that in the dimeric protein 3 group and the dimeric protein 7 group, as shown in FIG. 3.

In summary, in B16F10 mouse model, the efficacies of the three kinds of proteins were as follows: dimeric protein 3>dimeric protein 7>IL-15.

Test Example 4. Nude Mouse Tumor-Bearing Model

Purpose

Establish nude mouse tumor-bearing model using HCT-116 (human colon carcinoma) cells to assess the impact on tumor growth after administration of IL-15 drugs.

Material and Protocol

1. Test Protein

IL-15, dimeric protein 3 and dimeric protein 7.

2. Test Animal

BALB/cA-nude mice, SPF, 16-20 g, ♀ (female), available from Shanghai Super B&K Laboratory Animal Corp. Ltd.

3. Animal Test Procedure (1) Nude mice were adapted to the laboratory environment for 10 days.

(2) Tumor cell transplantation

Nude mice were inoculated subcutaneously in the right rib with HCT-116 cells ($5 \times 10^6$/mouse). Tumors grew for 20 days. When the tumor volume grew to $100 \pm 15$ mm$^3$, animals were randomly grouped (d0), n=6.

(3) Administration dosage and method

Each group was intraperitoneally injected once every two days (three times a week) with test drug IL-15 (2 μg/mouse), dimeric protein 3 (10 μg/mouse), or dimeric protein 7 (20 μg/mouse) (IL-15, dimeric protein 3 and dimeric protein 7 have the same molar amount of 0.15 nmol).

(4) Determination of tumor volume and weight of nude mice

Mice were measured for tumor volume 2-3 times per week (FIG. 4), weighed, and recorded. On day 27, mice were sacrificed to collect the tumor.

(5) Statistics

Excel statistical software: means were calculated as avg; SD was calculated as STDEV; SEM was calculated as STDEV/SQRT; and P value between different groups was calculated as TTEST.

Tumor volume (V) was calculated as: $V = \frac{1}{2} \times L_{length} \times L_{short}^2$ Relative volume (RTV)=$V_T/V_0$ Inhibition rate (%)=$(C_{RTV}-T_{RTV})/C_{RTV}$(%)

$V_0$ and $V_T$ represent the tumor volume at the beginning of the experiment and at the end of the experiment, respectively. $C_{RTV}$ and $T_{RTV}$ represent blank control group (Blank) and relative tumor volume at the end of the experiment, respectively.

3. Results

Figure 4:
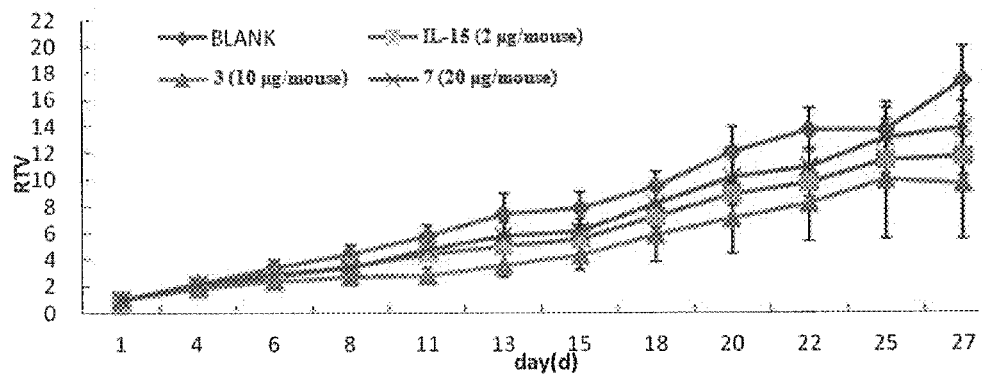
FIG. 4 shows the curative effect of different administered proteins on HCT-116 xenograft nude mice.

The effect of IL-15 protein in inhibiting growth of HCT-116 tumor is shown in Table 3 and FIG. 4. Equimolar IL-15, dimeric protein 3 and dimeric protein 7 were continuously administered for 27 days, once every two days. IL-15, dimeric protein 3 and dimeric protein 7 inhibited the growth of transplanted HCT-16 tumor, and the inhibition rates were 32%, 45%, and 20%, respectively. No significant difference was seen compared to the control group, because of significant individual differences. No deaths occurred during the administration, and no significant decrease in body weight was seen in each group during the administration, suggesting that the administration dosage at present does not have any significant toxicity.

Figure 5:
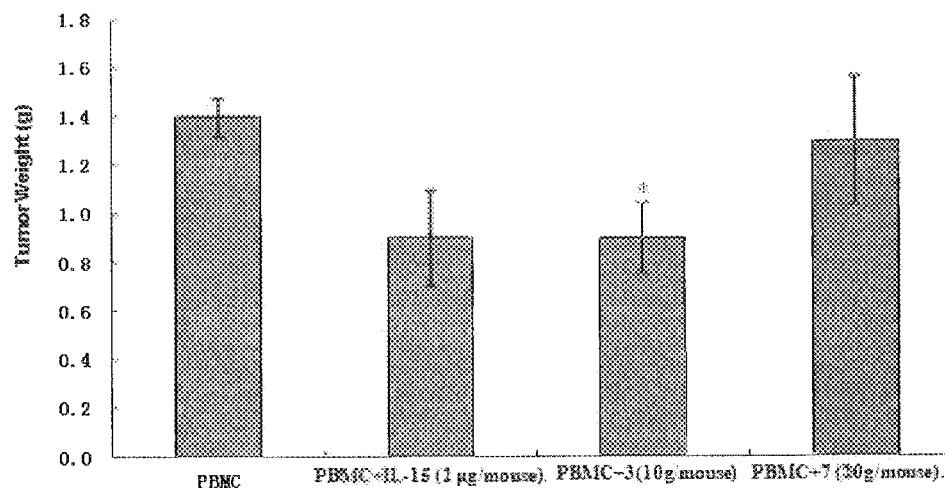
FIG. 5 shows the curative effect of different administered proteins on HCT-116 xenografts nude mice, tumor weight on day 27; * in the figure represents p<0.05, vs blank.

On day 27, tumors in each group were stripped and weighed, as shown in FIG. 5, and * in the figure represents p<0.05 compared to Blank, which indicated that the tumor weight in dimeric protein 3 group was significantly decreased compared to that in Blank, and the tumor weights in groups IL-15 and dimeric protein 7 were comparable with that in the Blank group.

In summary, in the HCT-116 nude model, the inhibitory efficacies of the 3 kinds of protein was: dimeric protein 3>IL-15>dimeric protein 7.

human PBMC cells (including T and NK cells) can be activated to kill cancer cells and inhibit tumor cell growth. NOD-SCID mouse model is a much closer mimic of the human immune system for killing tumor cells.

Material and Protocol

1. Test Protein

IL-15 protein purchased from Novoprotein Scientific Inc; IL-15, dimeric protein 3 and dimeric protein 7.

2. Test Animal

NOD-SCID female mice were purchased from Beijing Vital River Laboratory Animal Technology Co., Ltd (Lot number: 11400700006527), 6-8 weeks old, about 20 g, 5 in each drug group.

3. Animal Test Procedure (1) NOD-SCID mice were to adapt to the laboratory environment for 10 days.

(2) PBMC Cells Isolation 6 mL of lymphocyte separation medium (Lymphocyte Separation Medium, LSM) was aseptically transferred to a 15 mL-centrifuge tube (before, LSM was gently mixed by inverting the bottle);

4 mL of venous blood anti-coagulation treated with heparin was mixed with saline, and 8 mL of the diluted blood was carefully added into the LSM in the centrifuge tube (at room temperature, slowly added to form a clear stratification between blood and the LSM, rather than mixed into the LSM);

After centrifugation at room temperature at 400 g for 15-30 minutes, red blood cells and polymorphonuclear leukocytes were precipitated, and meanwhile, a layer of mononuclear cells was formed above the LSM;

Plasma was aspirated from 4-6 cm above the lymphocytes;

The lymphocyte layer and half of the LSM below it were aspirated and transferred to another centrifuge tube, followed by addition of an equal volume of balanced salt buffer PBS, and centrifuged for 10 minutes at room temperature at 1000 rpm;

Cells were washed with PBS buffer or RPMI-1640 medium, and resuspended with RPMI-1640 medium;

TABLE 3

Therapeutic effects of administered proteins on HCT-116 xenograft nude mice

| Group | Mean tumor volume (mm³) D0 | SEM | Mean tumor volume (mm³) D27 | SEM | Relative tumor volume D27 | SEM | % tumor inhibition D28 | p vs blank |
|---|---|---|---|---|---|---|---|---|
| BLANK | 89.82 | 8.84 | 1493.16 | 182.76 | 17.37 | 2.60 | | |
| IL-15 | 96.05 | 11.65 | 1098.37 | 177.68 | 11.73 | 1.47 | 32 | 0.09 |
| Dimeric protein 3 | 86.79 | 12.56 | 777.77 | 279.39 | 9.63 | 4.06 | 45 | 0.14 |
| Dimeric protein 7 | 96.30 | 16.22 | 1260.47 | 219.72 | 13.87 | 2.01 | 20 | 0.31 |

Test Example 5. Severe Combined Immunodeficient NOD-SCID Mice

Purpose

HCT-116 cells were mixed with human peripheral blood mononuclear cells (PBMC) in vitro, and inoculated into severe combined immunodeficient NOD-SCID mice. The impact on tumor growth after the administration of IL-15 was evaluated. NOD-SCID mice theoretically lack T cells and NK cells, and as a result, after administration of IL-15, After 3-4 hours of incubation at 37° C., suspended cells were collected and counted.

(3) Tumor cell transplantation

HCT-116 cells were mixed uniformly with PBMC cells at a ratio of 4:1, and inoculated subcutaneously on the right rib of NOD-SCID mice (HCT-116 cells: 5×10⁶/mouse, PBMC: 1.25×10⁶/mouse). Tumors were grown for 28 days.

(4) Administration dosage and method

Drugs were intraperitoneally injected from the next day after inoculation of HCT-116+PBMC cells, once every two days, for 10 consecutive doses. The dosage of IL-15 was 2 µg/mouse, the dosage of dimeric protein 3 was 10 µg/mouse, and the dosage of dimeric protein 7 was 20 µg/mouse (IL-15, dimeric protein 3 and dimeric protein 7 have the same molar amount of 0.15 nmol).

(5) Measurement of tumor volume and body weight of NOD-SCID mice

From day 12, mice were measured for tumor volume, weighed, and recorded every 2 to 3 days. On day 28, mice were sacrificed to obtain the tumor.

(6) Statistics

Excel statistical software: means were calculated as avg; SD value was calculated as STDEV; SEM value was calculated as STDEV/SQRT; and P value between different groups was calculated as TTEST.

Tumor volume ($V$) was calculated as: $V = \frac{1}{2} \times L_{length} \times L_{short}^2$ Inhibition rate (%) = $(V_T - V_0)/V_T$ (%)

$V_0$ and $V_T$ represent the tumor volume at the beginning of the experiment and at the end of the experiment, respectively.

3. Results

Figure 6:
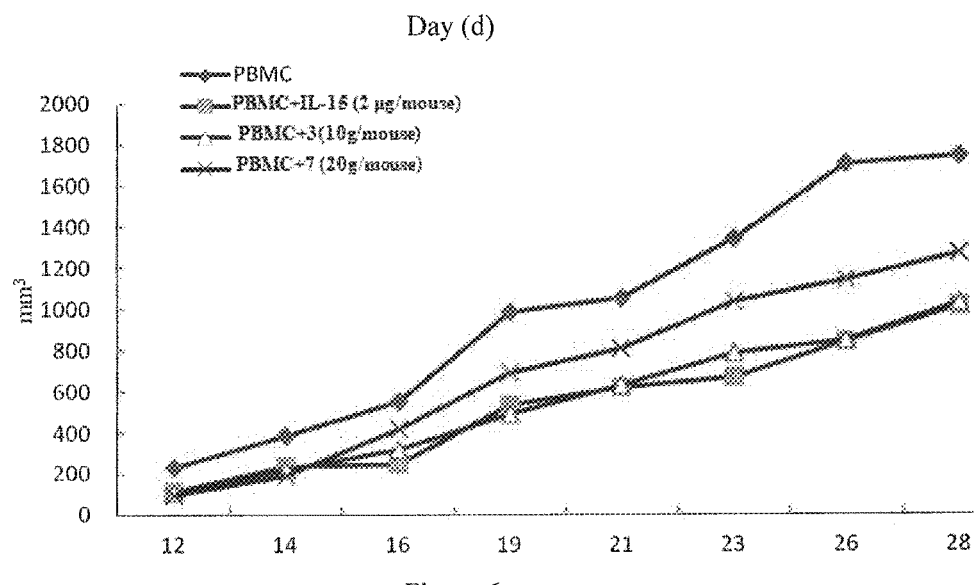
FIG. 6 shows the curative effect of different administered proteins on HCT-116+PBMC xenograft SCID mice.

From the next day after the inoculation of cells, equimolar IL-15, dimeric protein 3 and the dimeric protein 7 were administered continuously for 20 days, once every two days. The effect of IL-15 protein on inhibiting HCT-116+PBMC tumor growth was shown in Table 4 and FIG. 6: no tumor was found in each group in the first week. From day 12 (D12), tumors in each group were found, and the tumor volumes in the IL-15 group, the dimeric protein 3 group, and the dimeric protein 7 group were less than that in the PBMC group. On day 28 (D28), IL-15 and dimeric protein 3 significantly inhibited the growth of transplanted HCT-16 tumor cells, with inhibition rates of 42% and 41% respectively; the inhibition rate of the dimeric protein 7 group was 27%, exhibiting no significant difference compared to the PBMC group. No deaths occurred during the administration, and no significant decrease in body weight was seen in each group during the administration, suggesting that the administration dosage at present does not have significant toxicity.

Figure 7:
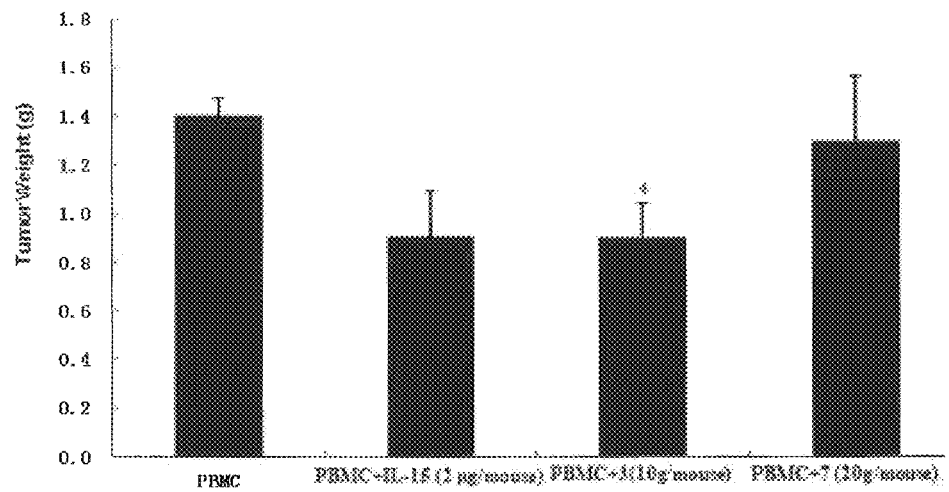
FIG. 7 shows the curative effect of different administered proteins on HCT-116+PBMC xenograft SCID mice, tumor weight on day 28; * in the figure represents p<0.05, vs PBMC.

On day 28, tumors in each group were stripped and weighed, and as shown in FIG. 7, the tumor weight in the dimeric protein 3 group was significantly decreased compared to that in the PBMC group; the tumor weight in the IL-15 group was decreased compared to that in the PBMC group, without a significant difference; and the tumor weight in the dimeric protein 7 group was comparable to that in PBMC group.

In summary, in the HCT-116+PBMC NOD-SCID mouse model, the inhibitory effect of the 3 kinds of protein was: dimeric protein 3≥IL-15>dimeric protein 7.

TABLE 4

Efficacy of administered proteins on HCT-116 + PBMC SCID xenografts

| Group | Mean tumor volume (mm³) D12 | SEM | Mean tumor volume (mm³) D28 | SEM | % inhibition ratio D28 (vs PBMC) | p (vs PBMC) |
|---|---|---|---|---|---|---|
| PBMC | 230.33 | 32.16 | 1746.91 | 173.76 | 0 | |
| PBMC + IL-15 (2 µg/mouse) | 115.09 | 35.82 | 1015.25 | 180.70 | 42 | 0.0193* |
| PBMC + Dimeric protein 3 (10 µg/mouse) | 107.27 | 18.32 | 1030.68 | 131.82 | 41 | 0.0111* |
| PBMC + Dimeric protein 7 (20 µg/mouse) | 94.68 | 13.98 | 1271.80 | 172.97 | 27 | 0.0886 |

*in the figure represents p < 0.05, vs PBMC.

Test Example 6. Proliferation Assay of Mo7e Cells In Vitro

1. Main materials

Mo7e (human megakaryocyte leukemia cell line) purchased from Peking Union Medical College;

IL-15 purchased from Novoprotein, Item No. C016, IL-15 analogs (dimeric proteins 11-17) from internal preparation;

Cell Counting Kit-8 (CCK-8) purchased from WST, Cat No. EX660;

GM-CSF purchased from NOVOProtein, Cat No. CC79.

2. Procedure

1) Mo7e was cultured in the incubator with modified RPMI-1640 medium at 37° C. (5% $CO_2$) (containing 2.05 mM L-glutamine, 10% FBS and 15 ng/ml GM-CSF);

2) Mo7e cells in good condition were centrifuged at room temperature, 150×g for 5 minutes. The supernatant was discarded;

3) The cell pellet was washed with GM-CSF-free medium twice and then counted;

4) Cell concentration was adjusted and plated in a 96-well plate with a cell number of 2×10⁴/well and a volume of 90 µl (GM-CSF-free), and kept in the cell incubator for culturing;

5) IL-15 and its analogs (dimeric proteins 11 to 17) were proportionally diluted four times with PBS, and 10 µl/well was added to the cell culture system after 2 hours of incubating the cells in 96-well plates. Each concentration was titrated in triplicate wells as well as blank wells (titrated with only PBS);

6) Cell plates were cultured in the incubator for 3 days;

7) All test wells were added with 10 µL of CCK-8, and incubated in the incubator for 3 hours;

8) Absorbance at 450 nm (OD450) was detected.

| Sample | EC50 (nM) relative activity |
|---|---|
| IL-15 (Control) | 100.00 |
| 11 | 951.57 |
| 12 | 186.96 |

-continued

| Sample | EC50 (nM) relative activity |
|---|---|
| 13 | 400.38 |
| 14 | 2526.19 |
| 15 | 2496.47 |
| 16 | 2988.73 |
| 17 | 2060.19 |

The Mo7e proliferation assay showed that test dimeric proteins 11-17 were significantly superior to the control IL-15.

Test Example 7. Mouse Lung Metastasis Model

1. Procedure

Thirty two (32) C57BL/6 mice (SPF, available from Shanghai Super B&K Laboratory Animal Corp. Ltd) were intravenously injected with $1.5 \times 10^5$ of B16F10 cells (Shanghai Life Sciences Research Institute of Cell Resource Center, lot No TCM36), and divided into 4 groups, with 8 in each group. Each group were intraperitoneally injected with PBS, 2 μg of IL-15, or 4.2 μg or 12.5 μg of dimeric protein 17 on Day 1, weighed once every 2-3 days, and one mouse from each group was sacrificed on day 14 for observation of lung metastasis. All C57BL/6 mice were sacrificed on day 16. Lungs were collected, weighed, observed for black lumps in the lungs, photographed, fixed in methanol, and the number of black lumps was counted.

2. Results

Lungs of mice in the PBS group showed a large number of metastatic melanoma lumps (73±43). Lungs in the IL-15 administration group showed a large number of metastatic melanoma lumps (65±29), which was 90% of that in the PBS group. Lungs in the 4.2 μg of dimeric protein 17 administration group exhibited several metastatic melanoma lumps (32±24), which was 44% of that in the PBS group; and lungs in the 12.5 μg of dimeric protein 17 administration group exhibited fewer metastatic melanoma lumps (14±14), which was 19% of that in the PBS group.

Figure 8:
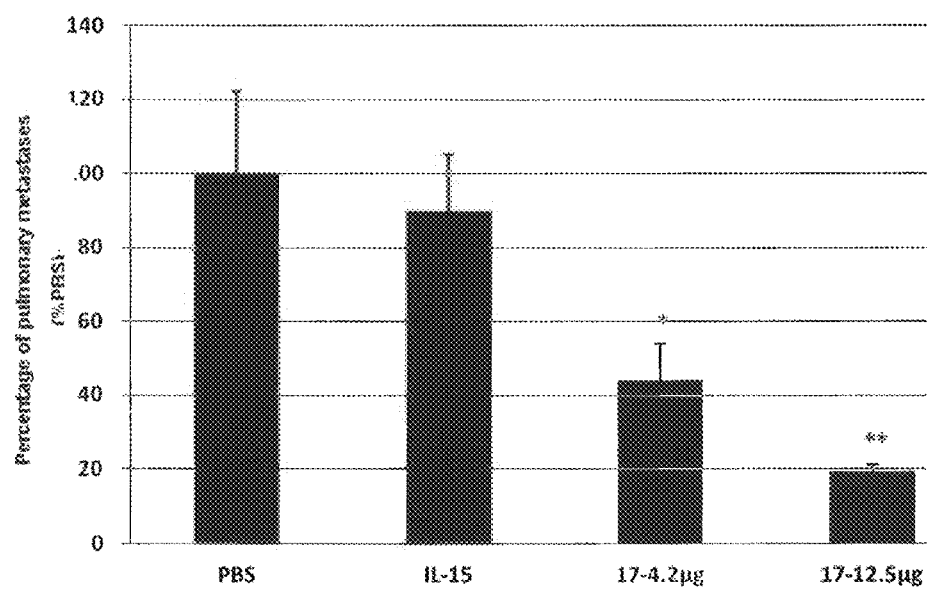
FIG. 8 shows a quantitative comparison of mice lung metastatic lumps after administration with dimeric protein 17, positive control (IL-15) and negative control (PBS); in the figure * represents P<0.05; and ** represents p<0.01, vs PBS.

In the present B16F10 model, the efficacy of dimeric protein 17 was significantly superior to that of IL-15, as shown in FIG. 8, which represents the number of lung metastatic lumps in each group, compared to the PBS group, where * represents p<0.05, and ** represents p<0.01.

Figure 9:
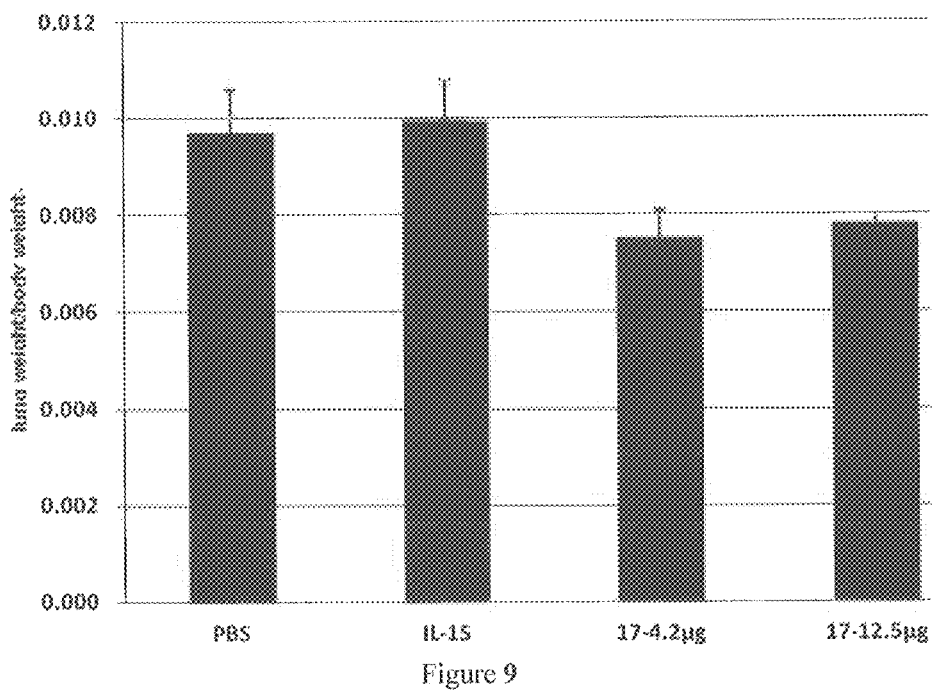
FIG. 9 shows A comparison of relative lung weight (lung weight/body weight) in mice after administration with dimeric protein 17, positive control (IL-15) and negative control (PBS)

The relative lung weight in the PBS group was higher than that in the dimeric protein 17 administration group, as shown in FIG. 9.

Figure 10:
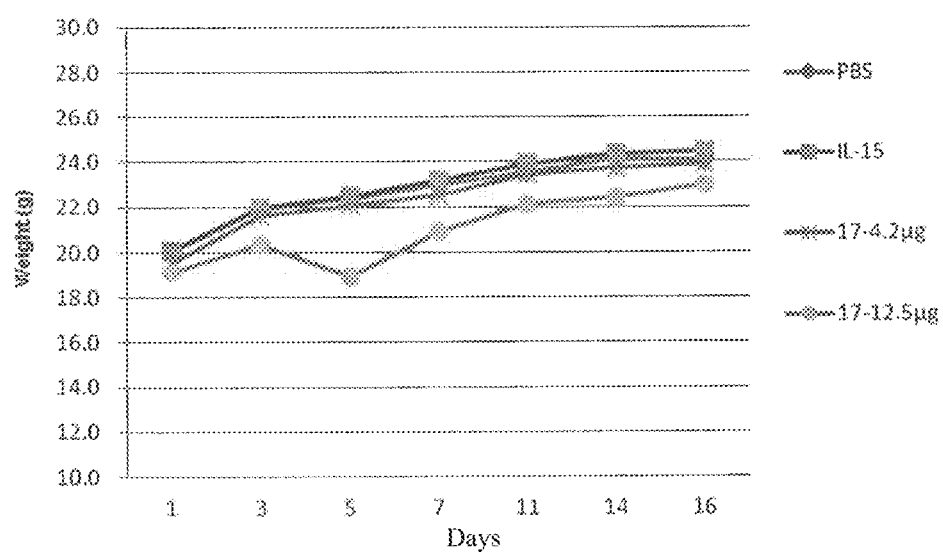
FIG. 10 shows a comparison of body weight in mice after administration with dimeric protein 17, positive control (IL-15) and negative control (PBS).

The body weight of mice in the 12.5 ug of dimeric protein 17 group was slightly decreased on day 5 after administration, and then gradually recovered, as shown in FIG. 10.

In summary, dimeric protein 17 can inhibit lung metastatic B16F10 cells in mice and exhibits dose effects.

The invention claimed is:

1. An IL-15 heterodimeric protein, comprising:
   protein (I) and protein (II);
   wherein protein (I) is recombinantly produced and comprises the sequence of IL-15 and the sequence of a first Fc variant;
   protein (II) is a second Fc variant, or is recombinantly produced and comprises the sequence of IL-15Rα or a variant thereof and the sequence of a second Fc variant, wherein the IL-15Rα variant is an extracellular domain of IL-15Rα or a functional fragment thereof, the functional fragment being a C-terminal truncated form of the extracellular domain of IL-15Rα having the activity of IL-15Rα; and
   protein (I) and protein (II) form a stable heterodimeric protein by an interaction between the first Fc variant and the second Fc variant.

2. The IL-15 heterodimeric protein according to claim 1, wherein the sequence of IL-15 comprises SEQ ID NO: 1.

3. The IL-15 heterodimeric protein according to claim 1, wherein protein (II) is a second Fc variant.

4. The IL-15 heterodimeric protein according to claim 1, wherein protein (II) is recombinantly produced by combining IL-15Rα or a variant thereof with a second Fc variant.

5. The IL-15 heterodimeric protein according to claim 1, wherein the sequence of the IL-15Rα variant is selected from the group consisting of SEQ ID NOs: 2-7.

6. The IL-15 heterodimeric protein according to claim 1, wherein:
   the first Fc variant is selected from the group consisting of a Knob modified Fc and a Hole modified Fc; and the second Fc variant is selected from the group consisting of a Hole modified Fc and a Knob modified Fc;
   when the first Fc variant is a Knob modified Fc, the second Fc variant is a Hole modified Fc; and when the second Fc variant is a Knob modified Fc, the first Fc variant is a Hole modified Fc.

7. The IL-15 heterodimeric protein according to claim 1, wherein the sequence of the first Fc variant is selected from the group consisting of SEQ ID NO: 26, SEQ ID NO: 27, SEQ ID NO: 28 and SEQ ID NO: 29; and the sequence of the second Fc variant is selected from the group consisting of SEQ ID NO: 26, SEQ ID NO: 27, SEQ ID NO: 28 and SEQ ID NO: 29.

8. The IL-15 heterodimeric protein according to claim 1, wherein the sequence of protein (I) is selected from the group consisting of SEQ ID NOs: 14-17; and the sequence of protein (H) is selected from the group consisting of SEQ ID NOs: 18-25 and 34-37.

9. The IL-15 heterodimeric protein according to claim 1, wherein the sequence of protein (I) is selected from the group consisting of SEQ ID NOs: 30-31; and the sequence of protein (H) is selected from the group consisting of SEQ ID NOs: 32-33.

10. A nucleic acid encoding the IL-15 heterodimeric protein according to claim 1.

11. A DNA vector comprising the nucleic acid according to claim 10.

12. A host cell comprising the DNA vector according to claim 11.

13. A method for preparing the IL-15 heterodimeric protein according to claim 1, comprising:
culturing a host cell comprising a DNA vector comprising a nucleic acid encoding the IL-15 heterodimeric protein according to claim 1 under a condition sufficient for expression of the IL-15 heterodimeric protein; and expressing and purifying the IL-15 heterodimeric protein.

14. A pharmaceutical composition comprising the IL-15 heterodimeric protein according to claim 1, and a pharmaceutically acceptable excipient, diluent or carrier.

15. A method of treating an IL-15 mediated disease or disorder comprising administering to a subject in need of the treatment the pharmaceutical composition of claim 14, wherein the IL-15 mediated disease or disorder is selected from the group consisting of cancer, infectious disease, and blood disease; wherein the cancer is selected from the group consisting of melanoma, colorectal cancer, lymphoma, renal cell carcinoma, and lung cancer; the infectious disease is selected from the group consisting of variola virus infection, HIV infection, and HBV infection; and the blood disease is acute myeloid leukemia.

16. The method according to claim 15, further comprising administering a small molecule inhibitor or an antibody to the subject, wherein the small molecule inhibitor is selected from the group consisting of alkylating agents, and the antibody is a monoclonal antibody.

17. A targeting protein molecule comprising the IL-15 heterodimeric protein according to claim 1.

18. An IL-15 heterodimeric protein selected from the group consisting of the following dimeric proteins c-q, wherein the dimeric proteins c-q each comprise respective protein (I) and protein (II):

| Dimeric Protein | Protein (I) | Protein (II) |
|---|---|---|
| c | IL-15-Fc-Knob (SEQ ID NO: 14) | Fc-Hole (SEQ ID NO: 27) |
| d | IL-15-Fc-Hole (SEQ ID NO: 15) | Fc-Knob (SEQ ID NO: 26) |
| e | Fc-Knob-IL-15 (SEQ ID NO: 16) | Fc-Hole (SEQ ID NO: 27) |
| f | Fc-Hole-IL-15 (SEQ ID NO: 17) | Fc-Knob (SEQ ID NO: 26) |
| g | IL-15-Fc-Knob (SEQ ID NO: 14) | IL-15Rα ECD-Fc-Hole (SEQ ID NO: 19) |
| h | IL-15-Fc-Hole (SEQ ID NO: 15) | IL-15Rα ECD-Fc-Knob (SEQ ID NO: 18) |
| i | Fc-Knob-IL-15 (SEQ ID NO: 16) | Fc-Hole-IL-15Rα ECD (SEQ ID NO: 21) |
| j | Fc-Hole-IL-15 (SEQ ID NO: 17) | Fc-Knob-IL-15Rα ECD (SEQ ID NO: 20) |
| k | IL-15-Fc-Knob (SEQ ID NO: 14) | IL-15Rα-sushi(77)-Fc-Hole (SEQ ID NO: 23) |
| l | Fc-Knob(M)-IL-15 (SEQ ID NO: 30) | Fc-Hole(M)-IL-15Rα-sushi(65) (SEQ ID NO: 32) |
| m | IL-15-Fc-Knob(M) (SEQ ID NO: 31) | IL-15Rα-sushi (65)-Fc-Hole(M) (SEQ ID NO: 33) |
| n | IL-15-Fc-Knob (SEQ ID NO: 14) | IL-15Rα-sushi(73)-Fc-Hole (SEQ ID NO: 34) |
| o | IL-15-Fc-Knob (SEQ ID NO: 14) | IL-15Rα-sushi(65)-Fc-Hole (SEQ ID NO: 35) |
| p | IL-15-Fc-Knob (SEQ ID NO: 14) | IL-15Rα-sushi(86)-Fc-Hole (SEQ ID NO: 36) |
| q | IL-15-Fc-Knob (SEQ ID NO: 14) | IL-15Rα-sushi(102)-Fc-Hole (SEQ ID NO: 37). |

19. A pharmaceutical composition comprising the IL-15 heterodimeric protein according to claim 18, and a pharmaceutically acceptable excipient, diluent or carrier.

* * * * *